(12) United States Patent
Schirmer et al.

(10) Patent No.: US 12,221,644 B2
(45) Date of Patent: Feb. 11, 2025

(54) PRODUCTION OF NON-NATIVE MONOUNSATURATED FATTY ACIDS IN BACTERIA

(71) Applicant: Genomatica, Inc., San Diego, CA (US)

(72) Inventors: Andreas W. Schirmer, South San Francisco, CA (US); Katherine Ann Murphy, South San Francisco, CA (US); Erin Frances Perry, South San Francisco, CA (US)

(73) Assignee: Genomatica, Inc., San Diego, CA (US)

( * ) Notice: Subject to any disclaimer, the term of this patent is extended or adjusted under 35 U.S.C. 154(b) by 262 days.

(21) Appl. No.: 17/271,439

(22) PCT Filed: Aug. 28, 2019

(86) PCT No.: PCT/US2019/048561
§ 371 (c)(1),
(2) Date: Feb. 25, 2021

(87) PCT Pub. No.: WO2020/047088
PCT Pub. Date: Mar. 5, 2020

(65) Prior Publication Data
US 2021/0189373 A1 Jun. 24, 2021

Related U.S. Application Data

(60) Provisional application No. 62/725,946, filed on Aug. 31, 2018.

(51) Int. Cl.
| | | |
|---|---|---|
| *C12N 9/02* | (2006.01) | |
| *C12N 9/04* | (2006.01) | |
| *C12N 9/10* | (2006.01) | |
| *C12N 9/16* | (2006.01) | |
| *C12N 9/88* | (2006.01) | |
| *C12P 7/6418* | (2022.01) | |
| *C12P 7/6481* | (2022.01) | |

(52) U.S. Cl.
CPC .......... *C12P 7/6481* (2013.01); *C12N 9/0006* (2013.01); *C12N 9/0008* (2013.01); *C12N 9/001* (2013.01); *C12N 9/1029* (2013.01); *C12N 9/16* (2013.01); *C12N 9/88* (2013.01); *C12P 7/6418* (2013.01); *C12Y 101/03013* (2013.01); *C12Y 102/01003* (2013.01); *C12Y 103/01038* (2013.01); *C12Y 203/01041* (2013.01); *C12Y 402/01059* (2013.01)

(58) Field of Classification Search
None
See application file for complete search history.

(56) References Cited

U.S. PATENT DOCUMENTS

| | | | |
|---|---|---|---|
| 9,447,436 B2 * | 9/2016 | Valle | C12N 9/0008 |
| 9,481,899 B2 | 11/2016 | Schirmer et al. | |
| 9,587,231 B2 | 3/2017 | Hom et al. | |
| 9,598,706 B2 | 3/2017 | Keasling et al. | |
| 9,670,512 B2 | 6/2017 | Schirmer et al. | |
| 9,683,219 B2 | 6/2017 | Rude et al. | |
| 9,683,247 B2 | 6/2017 | Lutes et al. | |
| 9,758,769 B2 | 9/2017 | Greenfield et al. | |
| 9,873,865 B2 | 1/2018 | Rude et al. | |
| 9,879,239 B2 | 1/2018 | Shumaker et al. | |
| 9,890,401 B2 | 2/2018 | Hu et al. | |
| 9,951,322 B2 | 4/2018 | Hom et al. | |
| 2017/0029854 A1 | 2/2017 | Del Cardayre et al. | |

FOREIGN PATENT DOCUMENTS

| | | |
|---|---|---|
| WO | 2014113571 A2 | 7/2014 |
| WO | 2016/157719 A1 | 10/2016 |

OTHER PUBLICATIONS

Bi, H., et. Al., "Unsaturated fatty acid synthesis in the gastric pathogen Helicobacter pylori proceeds via a backtracking mechanism," Cell Chem Biol., 23(12): 1480-1489 (2016).
Extended European Search Report from corresponding EP 19855367.9 dated Jun. 29, 2022.
International Search Report from corresponding PCT Application No. PCT/US2019/048561 dated Nov. 13, 2019.
Written Opinion from corresponding PCT Application No. PCT/US2019/048561 dated Nov. 13, 2019.
Wenning, L., et al., "Establishing Very Long-Chain Fatty Alcohol and Wax Ester Biosynthesis in *Saccharomyces cerevisiae*," Biotechnology and Bioengineering, 114(5): 1025-1035 (2017).
Bi, H., et al., "FabQ, a Dual-Function Dehydratase/Isomerase, Circumvents the Last Step of the Classical Fatty Acid Synthesis Cycle," Chem Biol., 20(9): 1157-1167 (2013).
International Preliminary Report on Patentability from corresponding PCT Application No. PCT/US2019/048561 dated Mar. 2, 2021.
Dodge, G. et al. (2019). Structural and dynamical rationale for fatty acid unsaturation in *Escherichia coli*. PNAS, 116(14): 6775-6783.
ExPASy Enzyme Entry: EC 1.3.8.7.
UniProtKB Entry: Q47146-FADE_ECOLI.
ExPASy Enzyme Entry: EC 1.3.3.6.
ExPASy Enzyme Entry: EC 5.3.3.14.

(Continued)

*Primary Examiner* — Richard G Hutson
(74) *Attorney, Agent, or Firm* — Harness Dickey & Pierce P.L.C.

(57) ABSTRACT

The disclosure relates to the field of specialty chemicals and methods for their synthesis. In embodiments, the disclosure provides viable bacterial cells which comprise heterologous dual 3-hydroxy-acyl-ACP dehydratase/isomerases, etc. The disclosure further provides monounsaturated fatty acid derivative molecules produced by the viable bacterial cells which are non-native to the bacterial cells. The disclosure further provides methods for the preparation and production of non-native monounsaturated fatty acid derivative molecules such as e.g., an ω3-monounsaturated fatty acid derivative, an ω5-monounsaturated fatty acid derivative, an ω9-monounsaturated fatty acid derivative, an ω11-monounsaturated fatty acid fatty acid derivative, etc.

20 Claims, 11 Drawing Sheets

(56) References Cited

OTHER PUBLICATIONS

Nettleton, J.A. et al. (2016). Dietary Fatty Acids: Is it Time to Change the Recommendations? Annals of Nutrition Metabolism, 68(4): 249-257.
Cao, Y. et al. (2014). Production of free monounsaturated fatty acids by metabolically engineered *Escherichia coli*. Biotechnology for Biofuels, 7(59): 1-11.
Rosano, G. et al. (2014). Recombinant protein expression in *Escherichia coli*: advances and challenges. Frontiers in Microbiology, 5(172): 1-17.
Magnuson, K. et al. (1993). Regulation of Fatty Acid Biosynthesis in *Escherichia coli*. Microbiological Reviews, 57(3): 522-542.

\* cited by examiner

MS Fragmentation of DMDS adduct of 16-hydroxyl-ω9-hexadecenoic acid (TMS derivatized sample)

PRODUCTION OF NON-NATIVE MONOUNSATURATED FATTY ACIDS IN BACTERIA

This application claims priority to and the benefit of U.S. Provisional Application No. 62/725,946, filed Aug. 31, 2018, which is incorporated herein by reference in its entirety.

FIELD

The disclosure relates to the field of specialty chemicals and methods for their synthesis. The disclosure provides bacteria engineered to produce non-native monounsaturated fatty acids and derivatives thereof. The disclosure further provides biochemical pathways, recombinant microorganisms and methods for the biological production of various monounsaturated fatty acid derivatives.

BACKGROUND

Monounsaturated fatty acids and fatty acid derivatives are attractive as the basis for many different products. For example, monounsaturated fatty acids are a component of good nutrition (see e.g., Nettleton J. A (2016) Ann Nutr Metab. 68:249-257); they serve as the basis for production of numerous useful molecules such as e.g., flavors and fragrances (see e.g., International Patent Application Publication WO 2016/157719) and they are ideal components for biodiesel since monounsaturated fatty acids improve fluidity at low temperatures and contribute to oxidative stability of the biodiesel product (see e.g., Yujin Cao et al. (2014) Biotechnol Biofuels.; 7: 59).

Unfortunately, most sources of monounsaturated fatty acids for nutrition, biodiesel, and for flavor and/or fragrance chemicals are dependent on plant and animal origins and thus can be limited in both quantity and quality.

In recent years, technology for the production of fatty acids and fatty acid derivatives has been successfully developed see e.g., U.S. Pat. Nos. 9,951,322; 9,890,401; 9,879,239; 9,873,865; 9,758,769; 9,683,247; 9,683,219; 9,670,512; 9,598,706; 9,587,231; 9,481,899. It would be greatly beneficial to be able to use such technology for the industrial scale production of monounsaturated fatty acids and fatty acid derivatives. In particular, it would be greatly beneficial to use *Escherichia coli* (*E. coli*) to prepare monounsaturated fatty acids and fatty acid derivatives.

*E. coli* possesses many advantages over other microorganisms for the industrial production of fatty acid derivatives and other chemicals (see e.g., Front Microbiol. 2014; 5: 172). Unfortunately, despite the advantages, there are some drawbacks when it comes to the production of monounsaturated fatty acid derivatives. As is well known in the art, *E. coli* and many other bacteria incorporate double bonds into monounsaturated fatty acids (mUFA) between the seventh and eighth carbon counting from the reduced end of the carbon chain (i.e. at the omega-7 ($\omega$-7) position). Thus, the production of monounsaturated fatty acids having double bonds in e.g. the $\omega$-3, $\omega$-5, $\omega$-6, $\omega$-8, $\omega$-9, $\omega$-11, $\omega$-12, etc. position are non-native to *E. coli*.

*E. coli* and other bacteria incorporate double bonds into monounsaturated fatty acids (mUFA) at the $\omega$-7 position due to the molecular mechanism utilized by *E. coli* and many other bacteria for the incorporation of double bonds into monounsaturated fatty acids (mUFA). The molecular mechanism for the incorporation of double bonds has been established for many years and is the paradigm for the "oxygen-independent" (anaerobic) mUFA biosynthesis (see e.g., Magnuson et al. (1993) Appl. Microbial Rev. 57(3): 522-542).

*E. coli* has two 3-hydroxy-acyl-ACP dehydratases, FabZ and FabA. The key enzyme for mUFA synthesis is one of these enzymes, FabA, which is a dual function dehydratase/isomerase. FabA isomerizes trans-2-decenoyl-ACP to cis-3-decenoyl-ACP. The latter cannot be reduced by trans-2-enoyl-ACP reductase (FabI), but can be elongated by $\beta$-keto-acyl-ACP synthase I (FabB) thereby fixing the double bond position in the co-7 position (see e.g. FIG. 1). It is generally accepted that FabA from most bacteria is very specific for isomerizing trans-2-decenoyl-ACP and that this is the reason for predominantly $\omega$-7 mUFAs in these bacteria.

Therefore, with regard to the synthesis of diverse mUFA, manufacturers who desire to produce mUFAs having a double bond in a position other than the $\omega$-7 position and who desire to harness the advantages and power of a bacterial platform are faced with a conundrum.

Clearly then, what is needed in the art are methods for the production of mUFA molecules that allow for the production of a full spectrum of mUFA molecules, including, but not limited to fatty acid derivative molecules having a double bond in the native $\omega$-7 position as well as fatty acid derivative molecules having a double bond in non-native positions such as e.g. $\omega$-9, $\omega$-3, $\omega$-5, $\omega$-6, $\omega$-8, $\omega$-11, $\omega$12, etc.

Fortunately, as will be clear from the detailed description that follows, the present disclosure provides for this and other needs.

SUMMARY

In one aspect the disclosure provides a viable recombinant bacterium comprising a heterologous dual 3-hydroxy-acyl-ACP dehydratase/isomerase. In an embodiment, the viable recombinant bacterium comprising a heterologous dual 3-hydroxy-acyl-ACP dehydratase/isomerase is a bacterium of taxonomic classification: Class gamma-proteobacteria, and the heterologous dual 3-hydroxy-acyl-ACP dehydratase/isomerase is derived from a bacterium of taxonomic classification: Class gamma-proteobacteria.

In one aspect the disclosure provides a viable recombinant bacterium comprising a heterologous dual 3-hydroxy-acyl-ACP dehydratase/isomerase, wherein the viable recombinant bacterium produces a non-native monounsaturated fatty acid derivative when cultured, and wherein the non-native monounsaturated fatty acid has a double bond in a position characteristic of the heterologous dual 3-hydroxy-acyl-ACP dehydratase/isomerase. In an embodiment, the viable recombinant bacterium is a bacterium of taxonomic classification: Class gamma-proteobacteria, and the heterologous dual 3-hydroxy-acyl-ACP dehydratase/isomerase is derived from a bacterium of taxonomic classification: Class gamma-proteobacteria. In another embodiment, the viable recombinant bacterium further comprises a heterologous thioesterase. In another embodiment, in the viable recombinant bacterium that further comprises a heterologous thioesterase, the non-native monounsaturated fatty acids comprise at least 30% of the total monounsaturated fatty acids. In another embodiment, the viable recombinant bacterium comprises non-native monounsaturated acyl-thioesters. In another embodiment, the viable recombinant bacterium comprises membrane phospholipids and the membrane phospholipids comprise the non-native monounsaturated fatty acid derivative. In an embodiment, the non-native monounsaturated fatty acid derivative comprises at least 10% of the membrane phospholipids.

In another embodiment, the viable recombinant bacterium further comprises a heterologous 3-hydroxyacyl-ACP dehydratase (fabZ). In an embodiment, the viable recombinant bacterium further comprising a heterologous 3-hydroxyacyl-ACP dehydratase (fabZ) further comprises a heterologous β-ketoacyl-ACP synthase I (fabB).

In an embodiment, the viable recombinant bacterium further comprising a heterologous 3-hydroxyacyl-ACP dehydratase (fabZ) further comprises a heterologous trans-2-enoyl-ACP reductase. In another embodiment, the viable recombinant bacterium further comprising a heterologous 3-hydroxyacyl-ACP dehydratase (fabZ) further comprises a heterologous thioesterase and a heterologous omega-hydroxylase. In an embodiment, the viable recombinant bacterium further comprising a heterologous 3-hydroxyacyl-ACP dehydratase (fabZ) a heterologous thioesterase and a heterologous omega-hydroxylase produces omega-hydroxy (ω-hydroxy) fatty acid derivatives when cultured and the ω-hydroxy fatty acid derivatives comprise non-native monounsaturated ω-hydroxy fatty acid derivatives. In an embodiment, the viable recombinant bacterium further comprising a heterologous 3-hydroxyacyl-ACP dehydratase (fabZ) a heterologous thioesterase and a heterologous omega-hydroxylase further comprises an alcohol dehydrogenase, an alcohol oxidase or an aldehyde dehydrogenase and the viable recombinant bacterium produces non-native diacids when cultured.

In another aspect, the viable recombinant bacterium comprising a heterologous dual 3-hydroxy-acyl-ACP dehydratase/isomerase, wherein the viable recombinant bacterium produces a non-native monounsaturated fatty acid derivative when cultured, and wherein the non-native monounsaturated fatty acid has a double bond in a position characteristic of the heterologous dual 3-hydroxy-acyl-ACP dehydratase/isomerase is a viable recombinant E. coli. In an embodiment, the heterologous dual 3-hydroxy-acyl-ACP dehydratase/isomerase is homologous to the FabA protein of E. coli. In another embodiment, the heterologous dual 3-hydroxy-acyl-ACP dehydratase/isomerase that is homologous to the FabA protein of E. coli is a FabA protein from a Marinobacter species. In an embodiment, the non-native monounsaturated fatty acid has the double bond in the position characteristic of the heterologous dual 3-hydroxy-acyl-ACP dehydratase/isomerase of Marinobacter which is an omega-9 (ω-9) position. In an embodiment, the viable recombinant E. coli comprising a heterologous dual 3-hydroxy-acyl-ACP dehydratase/isomerase, which produces a non-native monounsaturated fatty acid derivative when cultured, wherein the non-native monounsaturated fatty acid has a double bond in a position characteristic of the heterologous dual 3-hydroxy-acyl-ACP dehydratase/isomerase further comprises a heterologous 3-hydroxyacyl-ACP dehydratase (fabZ) from a Marinobacter species and a heterologous thioesterase, and the non-native monounsaturated fatty acid with the double bond in the ω-9 position comprises greater than 50% of the total monounsaturated fatty acids. In an embodiment, the non-native monounsaturated fatty acid with the double bond in the ω-9 position comprises greater than 75% of the total monounsaturated fatty acids produced when the viable recombinant bacterium is cultured. In an embodiment, the non-native monounsaturated fatty acid with the double bond in the ω-9 position comprises greater than 95% of the total monounsaturated fatty acids produced when the viable recombinant bacterium is cultured.

In an embodiment, the viable recombinant E. coli comprising a heterologous dual 3-hydroxy-acyl-ACP dehydratase/isomerase, wherein the viable recombinant bacterium produces a non-native monounsaturated fatty acid derivative when cultured, and wherein the non-native monounsaturated fatty acid has a double bond in a position characteristic of the heterologous dual 3-hydroxy-acyl-ACP dehydratase/isomerase further comprises a heterologous thioesterase.

In an embodiment, the viable recombinant E. coli comprising a heterologous dual 3-hydroxy-acyl-ACP dehydratase/isomerase, wherein the viable recombinant bacterium produces a non-native monounsaturated fatty acid derivative when cultured, and wherein the non-native monounsaturated fatty acid has a double bond in a position characteristic of the heterologous dual 3-hydroxy-acyl-ACP dehydratase/isomerase further comprises a heterologous 3-hydroxyacyl-ACP dehydratase (fabZ) from a Marinobacter species. In an embodiment, the viable recombinant E. coli further comprises a heterologous β-ketoacyl-ACP synthase I (fabB).

In an embodiment, the viable recombinant E. coli comprising a heterologous dual 3-hydroxy-acyl-ACP dehydratase/isomerase, wherein the viable recombinant bacterium produces a non-native monounsaturated fatty acid derivative when cultured, and wherein the non-native monounsaturated fatty acid has a double bond in a position characteristic of the heterologous dual 3-hydroxy-acyl-ACP dehydratase/isomerase further comprises a heterologous 3-hydroxyacyl-ACP dehydratase (fabZ) from a Marinobacter species further comprising a heterologous trans-2-enoyl-ACP reductase. In an embodiment, the viable recombinant E. coli further comprises a heterologous thioesterase and a heterologous omega-hydroxylase.

In an embodiment, In an embodiment, the viable recombinant E. coli comprising a heterologous dual 3-hydroxy-acyl-ACP dehydratase/isomerase, wherein the viable recombinant bacterium produces a non-native monounsaturated fatty acid derivative when cultured, and wherein the non-native monounsaturated fatty acid has a double bond in a position characteristic of the heterologous dual 3-hydroxy-acyl-ACP dehydratase/isomerase further comprises a heterologous 3-hydroxyacyl-ACP dehydratase (fabZ) from Marinobacter aquaeolei.

In another embodiment, the viable recombinant E. coli comprising a heterologous dual 3-hydroxy-acyl-ACP dehydratase/isomerase, that produces a non-native monounsaturated fatty acid derivative when cultured, wherein the non-native monounsaturated fatty acid has a double bond in a position characteristic of the heterologous dual 3-hydroxy-acyl-ACP dehydratase/isomerase wherein the heterologous dual 3-hydroxy-acyl-ACP dehydratase/isomerase is a FabA protein from a Marinobacter aquaeolei further comprises a heterologous thioesterase.

In another embodiment, the viable recombinant E. coli comprising a heterologous dual 3-hydroxy-acyl-ACP dehydratase/isomerase, that produces a non-native monounsaturated fatty acid derivative when cultured, wherein the non-native monounsaturated fatty acid has a double bond in a position characteristic of the heterologous dual 3-hydroxy-acyl-ACP dehydratase/isomerase wherein the heterologous dual 3-hydroxy-acyl-ACP dehydratase/isomerase is a FabA protein from a Marinobacter aquaeolei further comprises a heterologous 3-hydroxyacyl-ACP dehydratase (fabZ) from Marinobacter aquaeolei. In an embodiment, the viable recombinant E. coli further comprises a heterologous β-ketoacyl-ACP synthase I (fabB) from Marinobacter aquaeolei.

In another embodiment, the viable recombinant *E. coli* comprising a heterologous dual 3-hydroxy-acyl-ACP dehydratase/isomerase, that produces a non-native monounsaturated fatty acid derivative when cultured, wherein the non-native monounsaturated fatty acid has a double bond in a position characteristic of the heterologous dual 3-hydroxy-acyl-ACP dehydratase/isomerase wherein the heterologous dual 3-hydroxy-acyl-ACP dehydratase/isomerase is a FabA protein from a *Marinobacter aquaeolei* further comprises a heterologous 3-hydroxyacyl-ACP dehydratase (fabZ) from *Marinobacter aquaeolei*.

In another embodiment, the viable recombinant *E. coli* comprising a heterologous dual 3-hydroxy-acyl-ACP dehydratase/isomerase, that produces a non-native monounsaturated fatty acid derivative when cultured, wherein the non-native monounsaturated fatty acid has a double bond in a position characteristic of the heterologous dual 3-hydroxy-acyl-ACP dehydratase/isomerase wherein the heterologous dual 3-hydroxy-acyl-ACP dehydratase/isomerase is a FabA protein from a *Marinobacter aquaeolei* further comprises a heterologous 3-hydroxyacyl-ACP dehydratase (fabZ) from *Marinobacter aquaeolei*. In an embodiment, the viable recombinant *E. coli* further comprises a heterologous trans-2-enoyl-ACP reductase. In an embodiment, the viable recombinant *E. coli* further comprises a heterologous thioesterase and a heterologous omega-hydroxylase.

In another aspect the disclosure provides a method for producing a non-native monounsaturated fatty acid derivative in a recombinant microbial cell, the method comprising: culturing a viable recombinant bacterium that comprises a heterologous dual 3-hydroxy-acyl-ACP dehydratase/isomerase, wherein the viable recombinant bacterium produces the non-native monounsaturated fatty acid derivative when cultured, and wherein the non-native monounsaturated fatty acid has a double bond in a position characteristic of the heterologous dual 3-hydroxy-acyl-ACP dehydratase/isomerase. In an embodiment, the non-native monounsaturated fatty acid has a double bond in a position corresponding to $\omega$-9 in the carbon chain. In an embodiment, the dual 3-hydroxy-acyl-ACP dehydratase/isomerase is a fabA from a *Marinobacter* species. In an embodiment, the non-native monounsaturated fatty acid is selected from the group consisting of $\omega$9-tetradecenoic acid, $\omega$9-hexadecenoic acid and $\omega$9-octadecenoic acid. In an embodiment, the non-native monounsaturated fatty acid has a double bond in a position corresponding to $\omega$-5 in the carbon chain. In an embodiment, the dual 3-hydroxy-acyl-ACP dehydratase/isomerase is a fabA from a *Marinobacter* species. In an embodiment, the non-native monounsaturated fatty acid is $\omega$5-hexadecenoic acid.

In an aspect the disclosure provides a method for producing a non-native monounsaturated fatty acid derivative in a recombinant microbial cell, the method comprising: culturing a viable recombinant bacterium that comprises a heterologous dual 3-hydroxy-acyl-ACP dehydratase/isomerase, wherein the viable recombinant bacterium produces the non-native monounsaturated fatty acid derivative when cultured, and wherein the non-native monounsaturated fatty acid has a double bond in a position characteristic of the heterologous dual 3-hydroxy-acyl-ACP dehydratase/isomerase. The viable recombinant bacterium further comprises a heterologous 3-hydroxyacyl-ACP dehydratase (fabZ), a heterologous thioesterase and a heterologous omega-hydroxylase. In an embodiment, the non-native monounsaturated fatty acid derivative produced by this method is an omega hydroxylated non-native monounsaturated fatty acid. In an embodiment, the dual 3-hydroxy-acyl-ACP dehydratase/isomerase is a fabA from a *Marinobacter* species, the heterologous 3-hydroxyacyl-ACP dehydratase (fabZ) is from a *Marinobacter* species, and the heterologous thioesterase is from *Arabidopsis thaliana*. In an embodiment, the non-native monounsaturated fatty acid is omega-hydroxylated and has a double bond in a position position corresponding to $\omega$-9 in the carbon chain.

In an aspect the disclosure provides a method for producing a non-native monounsaturated fatty acid derivative in a recombinant microbial cell, the method comprising: culturing a viable recombinant bacterium that comprises a heterologous dual 3-hydroxy-acyl-ACP dehydratase/isomerase, wherein the viable recombinant bacterium produces the non-native monounsaturated fatty acid derivative when cultured, and wherein the non-native monounsaturated fatty acid has a double bond in a position characteristic of the heterologous dual 3-hydroxy-acyl-ACP dehydratase/isomerase. The viable recombinant bacterium further comprises a heterologous 3-hydroxyacyl-ACP dehydratase (fabZ), a heterologous thioesterase, a heterologous omega-hydroxylase and further comprises a heterologous alcohol oxidase/dehydrogenase and a heterologous aldehyde dehydrogenase. In an embodiment, the non-native monounsaturated fatty acid derivative produced by this method is a non-native monounsaturated fatty diacid.

In another aspect the disclosure provides a method for producing $\omega$9-(z7)-16-hydroxyhexadecenoic acid the method comprising: culturing a recombinant *Escherichia coli* (*E. coli*) cell wherein the recombinant *E. coli* heterologously expresses fabA and fabZ genes from *Marinobacter aquaeolei*, a FatA thioesterase from *Arabidopsis thaliana*, and a heterologous $\omega$-hydroxylase. In an embodiment, the method further comprises collecting the $\omega$9 (z7)-16-hydroxyhexadecenoic acid.

In another aspect, the disclosure provides a method for producing (z9) 18-hydroxyoctadecenoic acid, the method comprises: culturing a viable recombinant *Escherichia coli* (*E. coli*) cell wherein the recombinant *E. coli* heterologously expresses fabA and fabZ genes from *Marinobacter aquaeolei*, a FatA thioesterase from *Arabidopsis thaliana*, a $\beta$-ketoacyl-ACP synthase from *Marinobacter aquaeolei* and a heterologous $\omega$-hydroxylase. In an embodiment, the method further comprises collecting the (z9) 18-hydroxyoctadecenoic acid.

In another aspect, the disclosure provides a method for producing (z9)-1,18-octadecenedioic acid, the method comprises: culturing a viable recombinant *Escherichia coli* (*E. coli*) cell wherein the recombinant *E. coli* heterologously expresses fabA and fabZ genes from *Marinobacter aquaeolei*, a FatA thioesterase from *Arabidopsis thaliana*, a $\beta$-ketoacyl-ACP synthase from *Marinobacter aquaeolei*, a heterologous $\omega$-hydroxylase, an alcohol oxidase/dehydrogenase from *Pseudomonas oleovorans* and an aldehyde dehydrogenase from *Acinetobacter baylyi*. In an embodiment, the method further comprises collecting the (z9)-1,18-octadecenedioic acid.

Other features, objects and advantages of the invention will be apparent from the detailed description which follows.

DETAILED DESCRIPTION

Definitions

Figure 1:
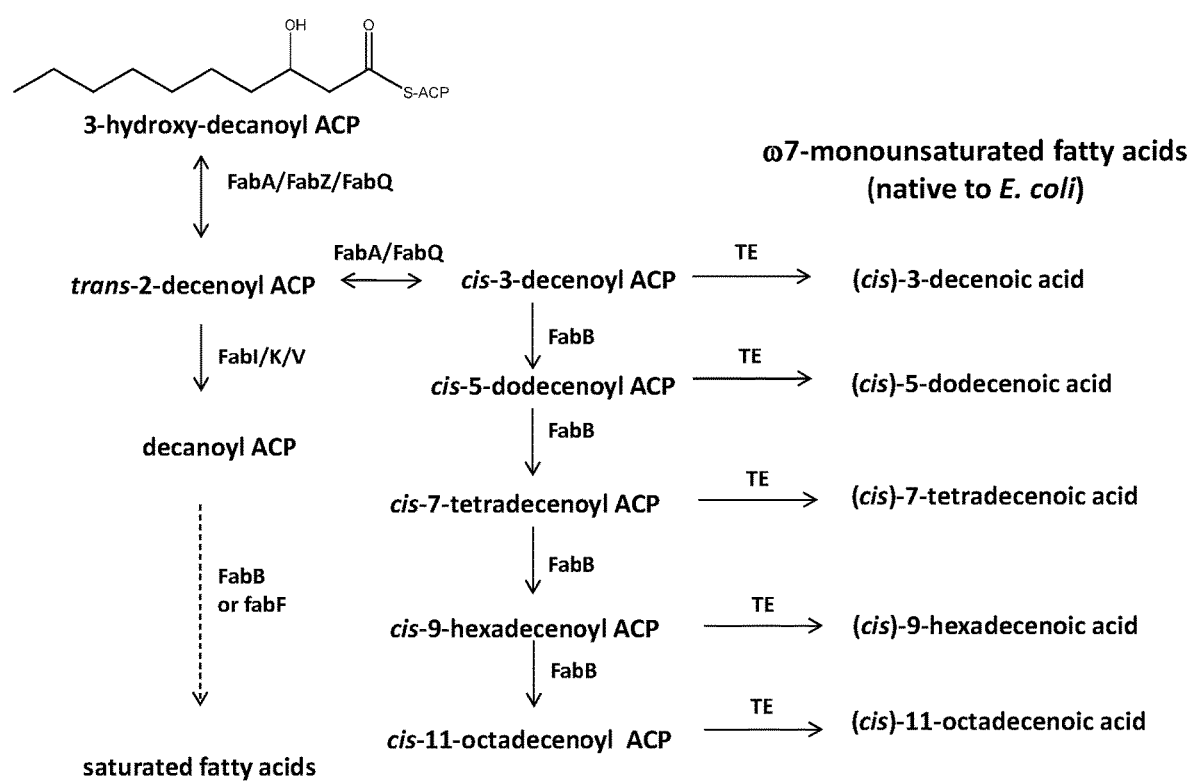
FIG. 1 Illustrates a biochemical pathway for the production of $\omega$7-monounsaturated fatty acids.

As used herein and in the appended claims, singular articles such as "a" and "an" and "the" and similar referents in the context of describing the elements are to be construed to cover both the singular and the plural, unless otherwise indicated herein or clearly contradicted by context.

As used herein, "about" is understood by persons of ordinary skill in the art and may vary to some extent depending upon the context in which it is used. If there are uses of the term which are not clear to persons of ordinary skill in the art given the context in which the term "about" is used, "about" will mean up to plus or minus 10% of the particular term.

As will be understood by one skilled in the art, for any and all purposes, all ranges disclosed herein also encompass any and all possible subranges and combinations of subranges thereof. Furthermore, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

Unless defined otherwise, technical and scientific terms used herein have the same meaning as commonly understood by a person of ordinary skill in the art. In particular, this disclosure utilizes routine techniques in the field of recombinant genetics, organic chemistry, fermentation and biochemistry. Basic texts disclosing the general terms in molecular biology and genetics include e.g., Lackie, *Dictionary of Cell and Molecular Biology*, Elsevier (5th ed. 2013). Basic texts disclosing methods in recombinant genetics and molecular biology include e.g., Sambrook et al., Molecular Cloning—A Laboratory Manual, Cold Spring Harbor Press 4th Edition (Cold Spring Harbor, N.Y. 2012) and Current Protocols in Molecular Biology Volumes 1-3, John Wiley & Sons, Inc. (1994-1998) and Supplements 1-115 (1987-2016). Basic texts disclosing the general methods and terms in biochemistry include e.g., *Lehninger Principles of Biochemistry* sixth edition, David L. Nelson and Michael M. Cox eds. W.H. Freeman (2012). Basic texts disclosing the general methods and terminology of fermentation include e.g., *Principles of Fermentation Technology*, 3rd Edition by Peter F Stanbury, Allan Whitaker and Stephen J Hall. Butterworth-Heinemann (2016). Basic texts disclosing the general methods and terms organic chemistry include e.g., Favre, Henri A. and Powell, Warren H. *Nomenclature of Organic Chemistry. IUPAC Recommendations and Preferred Name* 2013. Cambridge, UK: The Royal Society of Chemistry, 2013; *Practical Synthetic Organic Chemistry: Reactions, Principles, and Techniques*, Stephane Caron ed., John Wiley and Sons Inc. (2011); *Organic Chemistry*, 9th Edition—Francis Carey and Robert Giuliano, McGraw Hill (2013).

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the compounds having one or more of the utilities described herein, as well as a mixture of these various different forms.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, quinazolinones may exhibit the following isomeric forms, which are referred to as tautomers of each other:

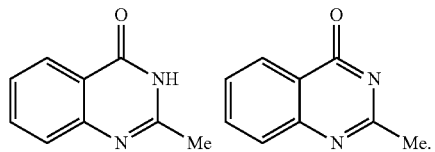

As another example, guanidines may exhibit the following isomeric forms in protic organic solution, also referred to as tautomers of each other:

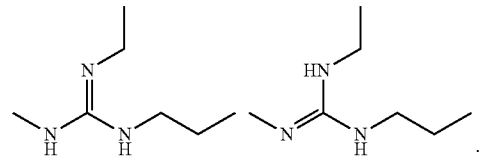

Because of the limits of representing compounds by structural formulas, it is to be understood that all chemical formulas of the compounds described herein represent all tautomeric forms of compounds and are within the scope of the present technology.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

Geometric isomers can be represented by the symbol which denotes a bond that can be a single, double or triple bond as described herein. Provided herein are various geometric isomers and mixtures thereof resulting from the arrangement of substituents around a carbon-carbon double bond. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or "trans," where "cis" represents substituents on the same side of the double bond and "trans" represents substituents on opposite sides of the double bond. The term "cis" represents substituents on the same side of the plane of the ring, and the term "trans" represents substituents on opposite sides of the plane of the ring. Mixtures of compounds wherein the substituents are disposed on both the same and opposite sides of plane of the ring are designated "cis/trans."

In certain embodiments, the pharmaceutically acceptable form thereof is an isomer. "Isomers" are different compounds that have the same molecular formula. "Stereoisomers" are isomers that differ only in the way the atoms are arranged in space. As used herein, the term "isomer" includes any and all geometric isomers and stereoisomers. For example, "isomers" include cis- and trans-isomers, E- and Z-isomers, R- and S-enantiomers, diastereomers, (d)-isomers, (l)-isomers, racemic mixtures thereof, and other mixtures thereof, as falling within the scope of this disclosure.

"Enantiomers" are a pair of stereoisomers that are non-superimposable mirror images of each other. A mixture of a pair of enantiomers in any proportion can be known as a "racemic" mixture. The term "(+−)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer, the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry, as (R)- or (S)-. The present chemical entities, pharmaceutical compositions and methods are meant to include all such possible isomers, including racemic mixtures, optically pure forms and intermediate mixtures. Optically active (R)- and (S)-isomers can be prepared, for example, using chiral synthons or chiral reagents, or resolved using conventional techniques. The optical activity of a compound can be analyzed via any suitable method, including but not limited to chiral chromatography and polarimetry, and the degree of predominance of one stereoisomer over the other isomer can be determined.

The term "fatty acid" as used herein, refers to an aliphatic carboxylic acid having the formula RCOOH wherein R is an aliphatic group having at least 4 carbons, typically between about 4 and about 28 carbon atoms. The aliphatic R group can be saturated or unsaturated, branched or unbranched. Unsaturated "fatty acids" may be monounsaturated or polyunsaturated.

A "fatty acid" or "fatty acids", as used herein, can be produced within a cell through the process of fatty acid biosynthesis, through the reverse of fatty acid degradation or beta-oxidation, or they can be fed to a cell. As is well known in the art, fatty acid biosynthesis is generally a malonyl-CoA dependent synthesis of acyl-ACPs or acyl CoAs, while the reverse of beta-oxidation results is acetyl-CoA dependent and results in the synthesis of acyl-CoAs. Fatty acids fed to cell are converted to acyl-CoAs and can be converted to acyl-ACPs. Fatty acids can be synthesized in a cell by natural fatty acid biosynthetic pathways or can be synthesized from heterologous fatty acid biosynthetic pathways that comprise a combination of fatty acid biosynthetic and/or degradation enzymes that result in the synthesis of acyl-CoAs and/or Acyl-ACPs.

Fatty acid biosynthesis and degradation occur in all life forms, including prokaryotes, single cell eukaryotes, higher eukaryotes, and Archaea. The tools and methods disclosed herein are useful in the production of fatty acid derivatives that are derived through any one or more of fatty acid synthesis, degradation, or feeding in any organism that naturally produces alkyl thioesters.

The term "fatty acid derivative" as used herein, refers to a product derived from a fatty acid. Thus, a "fatty acid derivative" includes "fatty acids" as defined above. In general, "fatty acid derivatives" include malonyl-CoA derived compounds including acyl-ACP or acyl-ACP derivatives. "Fatty acid derivatives" also include malonyl-CoA derived compounds such as acyl-CoA or acyl-CoA derivatives. "Fatty acid derivatives" also include acetyl-CoA derived compounds such as acyl-CoA or acyl-CoA derivatives. Thus, a "fatty acid derivatives" include alkyl-thioesters and acyl-thioesters. Further, a "fatty acid derivative" includes a molecule/compound that is derived from a metabolic pathway that includes a fatty acid derivative enzyme. Exemplary fatty acid derivatives include fatty acids, fatty acid esters (e.g., waxes, fatty acid esters, fatty acid methyl esters (FAME), fatty acid ethyl esters (FAEE)), fatty alcohol acetate esters (FACE), fatty amines, fatty aldehydes, fatty alcohols, hydrocarbons e.g., alkanes, alkenes, etc, ketones, terminal olefins, internal olefins, 3-hydroxy fatty acid derivatives, bifunctional fatty acid derivatives (e.g., ω-hydroxy fatty acids, (ω-1)-hydroxy fatty acids, (ω-2)-hydroxy fatty acids, (ω-3)-hydroxy fatty acids, 10-hydroxy fatty acids, 1,3 fatty-diols, α,ω-diols, α,ω-3-hydroxy triols, ω-hydroxy FAME, ω-OH FAEE, etc.), and unsaturated fatty acid derivatives, including unsaturated compounds of each of the above mentioned fatty acid derivatives.

The expression "fatty acid derivative composition" as used herein, refers to a composition of fatty acid derivatives, for example a fatty acid composition produced by viable recombinant bacterium comprising a heterologous dual 3-hydroxy-acyl-ACP dehydratase/isomerase as disclosed herein. A "fatty acid derivative composition" may comprise a single fatty acid derivative species or may comprise a mixture of fatty acid derivative species. In some exemplary embodiments, the mixture of fatty acid derivatives includes more than one type of fatty acid derivative product (e.g., fatty acids, fatty acid esters, fatty alcohols, fatty alcohol acetates, fatty aldehydes, fatty amine, bifunctional fatty acid derivatives, and non-native monounsaturated fatty acid derivatives, etc.). In other exemplary embodiments, the mixture of fatty acid derivatives includes a mixture of non-native monounsaturated fatty acid esters (or another fatty acid derivative) with different chain lengths, saturation and/or branching characteristics. In other exemplary embodiments, the mixture of fatty acid derivatives comprises predominantly one type of fatty acid derivative e.g., an ω3-monounsaturated fatty acid or fatty acid derivative composition, an ω5-monounsaturated fatty acid or fatty acid derivative composition, an ω11-monounsaturated fatty acid or fatty acid derivative composition, etc. In still other exemplary embodiments, a "fatty acid derivative composition" comprises a mixture of more than one type of fatty acid derivative product e.g., fatty acid derivatives with different chain lengths, saturation and/or branching characteristics. In still other exemplary embodiments, a "fatty acid derivative composition" comprises a mixture of fatty esters and 3-hydroxy esters. In still other exemplary embodiments, a fatty acid derivative composition comprises a mixture of fatty alcohols and fatty aldehydes, for example a mixture of non-native monounsaturated fatty alcohols or fatty aldehydes. In still other exemplary embodiments, a fatty acid derivative composition comprises a mixture of FAME and/or FAEE. In still other exemplary embodiments, a fatty acid derivative composition comprises a mixture of fatty alcohol acetate esters (FACE), for example a mixture of non-native monounsaturated fatty alcohol acetate esters (FACE). In other exemplary embodiments, the mixture of fatty acid derivatives includes a mixture of non-native monounsaturated fatty acid derivatives with different chain lengths, saturation and/or functional group characteristics.

The term "multifunctional fatty acid derivatives" or equivalently "multifunctional molecules" as used herein, refers to fatty acid derivative molecules typically having a carbon chain length of between 8 and 18 carbons that have at least three functional groups which comprise a heteroatom. In some embodiments, "multifunctional molecules" have more than 18 carbons, e.g., 19, 20, 21, 22, 23, 24 carbons. Exemplary functional groups which comprise a heteroatom include e.g. a hydroxy or equivalently, hydroxyl (—OH), oxo, carboxyl (COOH), amino (NH2), O-acetyl (CO2C2H3), methoxy (OCH3) or ester (CO2CH3, CO2C2H5, CO2C3H7, CO2C2H3) group.

"Multifunctional fatty acid derivatives" disclosed herein may be saturated or unsaturated multifunctional fatty acid derivatives. In embodiments an unsaturated "multifunctional molecule" is a non-native monounsaturated multifunctional molecule. In other embodiments a "multifunctional molecule" is a native monounsaturated multifunctional molecule. For example, (9E)-1,3,16-trihydroxy-hexadecene produced in *E. coli*, has a 16-hydroxyl group that is added by a hydroxylase to the reducing end of (9E)-1,3 dihydroxy hexadecane, a fatty diol unsaturated at the omega-7 position.

The term "non-native monounsaturated fatty acid derivative" as used herein, refers to any monounsaturated fatty acid derivative derived from a monounsaturated fatty acid acyl-thioester where the double bond position is non-native to the producing (host) bacterium. For example, in *E. coli* the native double-bond position in monounsaturated fatty acid acyl-thioesters is omega-7 (ω7). Therefore, for example in *E. coli*, a monounsaturated fatty acid derivative derived from monounsaturated fatty acid acyl-thioester with a double bond in a position other than ω7 is defined as non-native monounsaturated fatty acid derivative for this bacterium.

"Fatty acid derivative compositions" may comprise non-native monounsaturated fatty acid derivatives. Compositions comprising non-native monounsaturated fatty acid derivatives produced by the viable recombinant bacteria disclosed herein typically comprise compositions wherein the non-native monounsaturated fatty acid derivative is at least about 10% of the total monounsaturated fatty acid derivatives. In some embodiments, compositions comprising non-native monounsaturated fatty acid derivatives produced by the viable recombinant bacteria disclosed herein comprise compositions wherein the non-native monounsaturated fatty acid derivative is at least about 20% of the total monounsaturated fatty acid derivatives. In other embodiments, compositions comprising non-native monounsaturated fatty acid derivatives produced by the viable recombinant bacteria disclosed herein comprise compositions wherein the non-native monounsaturated fatty acid derivative is at least about 30%, at least about 40%, at least about 50%, at least about 60%, at least about 70%, at least about 75%, at least about 80%, at least about 85%, at least about 90%, at least about 95%, at least about 96%, at least about 97%, at least about 98%, at least about 99%, of the total monounsaturated fatty acid derivatives.

The term "malonyl-CoA derived compound" as used herein refers to any compound or chemical entity (i.e., intermediate or end product) that is made via a biochemical pathway wherein malonyl-CoA functions as intermediate and/or is made upstream of the compound or chemical entity. For example, a malonyl-CoA derived compound may include, but is not limited to, a fatty acid derivative such as, for example, a fatty acid; a fatty ester including, but not limited to a fatty acid methyl ester (FAME) and/or a fatty acid ethyl ester (FAEE); a fatty alcohol; a fatty aldehyde; a fatty amine; an alkane; an olefin or alkene; a hydrocarbon; a beta hydroxy fatty acid derivative, a bifunctional fatty acid derivative, a multifunctional fatty acid derivative and/or a native or non-native unsaturated fatty acid derivative.

As used herein "alkyl-thioester" or equivalently an "acyl thioester" is a compound in which the carbonyl carbon of an acyl chain and the sulfydryl group of an organic thiol forms a thioester bond. Representative organic thiols include Cystein, beta-cysteine, glutathione, mycothiol, pantetheine, Coenzyme A (CoA) and the acyl carrier protein (ACP). Thus "acyl-ACP" refers to an alkyl thioester formed between the carbonyl carbon of an acyl chain and the sulfhydryl group of the phosphopantetheinyl moiety of an ACP. An "Acyl-CoA" refers to an alkyl thioester formed between the carbonyl carbon of an acyl chain and the sulfhydryl group of the phosphopantetheinyl moiety of CoA. In some exemplary embodiments an alkyl thioester, such as acyl-ACP or acyl CoA, is an intermediate in the synthesis of fully saturated acyl-thioesters. In other exemplary embodiments an alkyl thioester, such as acyl-ACP or acyl CoA, is an intermediate in the synthesis of unsaturated acyl thioesters. In some exemplary embodiments, the carbon chain of the acyl group of an acyl thiester has 5, 6, 7, 8, 9, 10, 11, 12, 13, 14, 15, 16, 17, 18, 19, 20, 21, 22, 23, 24, 25, 26, 27 or 28 carbons. In other exemplary embodiments, the carbon chain of the acyl group of acyl-thioester is a medium-chain and has 6, 7, 8, 9, 10, 11, 12, 13, 14, 15, 16 or 18 carbons. In other exemplary embodiments the carbon chain of the acyl group of acyl-thioester is 8 carbons in length. In other exemplary embodiments the carbon chain of the acyl group of acyl-thioester is 10 carbons in length. In still other exemplary embodiments, the carbon chain of the acyl group of acyl-thioester is 12 carbons in length. In still other exemplary embodiments, the carbon chain of the acyl group of acyl-thioester is 14 carbons in length. In still other exemplary embodiments, the carbon chain of the acyl group of acyl-thioester is 16 carbons in length. Each of these acyl-thioesters are substrates for fatty acid derivative enzymes such as e.g., thioesterases, acyl ACP reductases, ester synthases and their engineered variants that convert the acyl-thioester to fatty acid derivatives.

As used herein, the expression "fatty acid derivative biosynthetic pathway" refers to a biochemical pathway that produces fatty acid derivatives. The enzymes that comprise a "fatty acid derivative biosynthetic pathway" are thus referred to herein as "fatty acid derivative biosynthetic polypeptides" or equivalently "fatty acid derivative enzymes". As discussed supra, the term "fatty acid derivative," includes a molecule/compound derived from a biochemical pathway that includes a fatty acid derivative enzyme. Thus, a thioesterase enzyme (e.g., an enzyme having thioesterase activity EC 3.1.1.14) is a "fatty acid derivative biosynthetic peptide" or equivalently a "fatty acid derivative enzyme." In addition to a thioesterase, a fatty acid derivative biosynthetic pathway may include additional fatty acid derivative enzymes to produce fatty acid derivatives having desired characteristics. Thus the term "fatty acid derivative enzymes" or equivalently "fatty acid derivative biosynthetic polypeptides" refers to, collectively and individually, enzymes that may be expressed or overexpressed to produce fatty acid derivatives. Non-limiting examples of "fatty acid derivative enzymes" or equivalently "fatty acid derivative biosynthetic polypeptides" include e.g., fatty acid synthases, thioesterases, acyl-CoA synthetases, acyl-CoA reductases, acyl ACP reductases, alcohol dehydrogenases, alcohol oxidases, aldehyde dehydrogenases, qwalcohol O-acyltransferases, fatty alcohol-forming acyl-CoA reductases, fatty acid decarboxylases, fatty aldehyde decarbonylases and/or oxidative deformylases, carboxylic acid reductases, fatty alcohol 0-acetyl transferases, ester synthases, etc. "Fatty acid derivative enzymes" or equivalently "fatty acid derivative biosynthetic polypeptides" convert substrates into fatty acid derivatives. In exemplary embodiments, a suitable substrate for a fatty acid derivative enzyme may be a first fatty acid derivative, which is converted by the fatty acid derivative enzyme into a different, second fatty acid derivative.

The expression "dual 3-hydroxy-acyl-ACP dehydratase/isomerases" as used herein, refers to enzymes having (3-hydroxyacyl-[acyl-carrier-protein] dehydratase) activity described by EC number: EC 4.2.1.59 and acyl-carrier protein isomerase activity described by EC number: EC 5.3.3.14 (see e.g., Heath R J, Rock C O (1996) Roles of the FabA and FabZ beta-hydroxyacyl-acyl carrier protein dehydratases in *Escherichia coli* fatty acid biosynthesis. J Biol Chem 271:27795-801).

Sequence Accession numbers throughout this description were obtained from databases provided by the NCBI (National Center for Biotechnology Information) maintained by the National Institutes of Health, U.S.A. (which are identified herein as "NCBI Accession Numbers" or alternatively as "GenBank Accession Numbers" or alternatively a simply "Accession Numbers"), and from the UniProt Knowledgebase (UniProtKB) and Swiss-Prot databases provided by the Swiss Institute of Bioinformatics (which are identified herein as "UniProtKB Accession Numbers").

The term "enzyme classification (EC) number" refers to a number that denotes a specific polypeptide sequence or enzyme. EC numbers classify enzymes according to the reaction they catalyze. EC numbers are established by the nomenclature committee of the international union of biochemistry and molecular biology (IUBMB), a description of which is available on the IUBMB enzyme nomenclature website on the world wide web.

As used herein, the term "isolated," with respect to products (such as monounsaturated fatty acid derivatives disclosed herein) refers to products that are separated from cellular components, cell culture media, or chemical or synthetic precursors. The monounsaturated fatty acid derivatives disclosed herein produced by the methods disclosed herein can be relatively immiscible in the fermentation broth, as well as in the cytoplasm. Therefore, in exemplary embodiments, the non-native monounsaturated fatty acid derivatives disclosed herein collect in an organic phase extracellularly and are thereby "isolated".

As used herein, the terms "polypeptide" and "protein" are used interchangeably to refer to a polymer of amino acid residues that is typically 12 or more amino acids in length. Polypeptides less than 12 amino acids in length are referred to herein as "peptides". The terms apply to amino acid polymers in which one or more amino acid residue is an artificial chemical mimetic of a corresponding naturally occurring amino acid, as well as to naturally occurring amino acid polymers and non-naturally occurring amino acid polymers. The term "recombinant polypeptide" refers to a polypeptide that is produced by recombinant techniques, wherein generally DNA or RNA encoding the expressed protein is inserted into a suitable expression vector that is in turn used to transform a host cell to produce the polypeptide. In some exemplary embodiments, DNA or RNA encoding an expressed peptide, polypeptide or protein is inserted into the host chromosome via homologous recombination or other means well known in the art, and is so used to transform a host cell to produce the peptide or polypeptide. Similarly, the terms "recombinant polynucleotide" or "recombinant nucleic acid" or "recombinant DNA" are produced by recombinant techniques that are known to those of skill in the art (see e.g., methods described in Sambrook et al. (supra) and/or Current Protocols in Molecular Biology (supra).

When referring to two nucleotide or polypeptide sequences, the "percentage of sequence identity" between the two sequences is determined by comparing the two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The "percentage of sequence identity" is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

Thus, the expression "percent identity," or equivalently "percent sequence identity" in the context of two or more nucleic acid sequences or peptides or polypeptides, refers to two or more sequences or subsequences that are the same or have a specified percentage of nucleotides or amino acids that are the same (e.g., about 50% identity, preferably 55%, 60%, 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured e.g., using a BLAST or BLAST 2.0 sequence comparison algorithm with default parameters (see e.g., Altschul et al. (1990) *J. Mol. Biol.* 215(3):403-410) and/or the NCBI web site at ncbi.nlm.nih.gov/BLAST/) or by manual alignment and visual inspection. Percent sequence identity between two nucleic acid or amino acid sequences also can be determined using e.g., the Needleman and Wunsch algorithm that has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6 (Needleman and Wunsch (1970) *J. Mol. Biol.* 48:444-453). The percent sequence identity between two nucleotide sequences also can be determined using the GAP program in the GCG software package, using a NWSgapdna.CMP matrix and a gap weight of 40, 50, 60, 70, or 80 and a length weight of 1, 2, 3, 4, 5, or 6. One of ordinary skill in the art can perform initial sequence identity calculations and adjust the algorithm parameters accordingly. A set of parameters that may be used if a practitioner is uncertain about which parameters should be applied to determine if a molecule is within a sequence identity limitation of the claims, are a Blossum 62 scoring matrix with a gap penalty of 12, a gap extend penalty of 4, and a frameshift gap penalty of 5. Additional methods of sequence alignment are known in the biotechnology arts (see, e.g., Rosenberg (2005) BMC Bioinformatics 6:278; Altschul et al. (2005) FEBS 272(20): 5101-5109).

Two or more nucleic acid or amino acid sequences are said to be "substantially identical," when they are aligned and analyzed as discussed above and are found to share about 50% identity, preferably 55%, 60%, 65%, 70%, 75%, 80%, 85%, 90%, 91%, 92%, 93%, 94%, 95%, 96%, 97%, 98%, 99%, or higher identity over a specified region. Two nucleic acid sequences or polypeptide sequences are said to be "identical" if the sequence of nucleotides or amino acid residues, respectively, in the two sequences are the same when aligned for maximum correspondence as described above. This definition also refers to, or may be applied to, the compliment of a test sequence. Identity is typically calculated over a region that is at least about 25 amino acids or nucleotides in length, or more preferably over a region that is 50-100 amino acids or nucleotides in length, or over the entire length of a given sequence.

The expressions "hybridizes under low stringency, medium stringency, high stringency, or very high stringency conditions" describe conditions for hybridization and washing. Guidance for performing hybridization reactions can be found e.g., in Current Protocols in Molecular Biology, John Wiley & Sons, N.Y. (1989), 6.3.1-6.3.6. Aqueous and non-aqueous methods are described in the cited reference and either method can be used. Specific hybridization conditions referred to herein are as follows: (1) low stringency hybridization conditions—6× sodium chloride/sodium citrate (SSC) at about 45° C., followed by two washes in 0.2×SSC, 0.1% SDS at least at 50° C. (the temperature of the washes can be increased to 55° C. for low stringency conditions); (2) medium stringency hybridization conditions—6×SSC at about 45° C., followed by one or more washes in 0.2×SSC, 0.1% SDS at 60° C.; (3) high stringency hybridization conditions—6×SSC at about 45° C., followed by one or more washes in 0.2.×SSC, 0.1% SDS at 65° C.; and (4) very high stringency hybridization conditions—0.5M sodium phosphate, 7% SDS at 65° C., followed by one or more washes at 0.2×SSC, 1% SDS at 65° C. Very high stringency conditions (4) are the preferred conditions unless otherwise specified.

The term "endogenous" as used herein refers to a substance e.g., a nucleic acid, protein, etc. that is produced from within a cell. Thus, an "endogenous" polynucleotide or polypeptide refers to a polynucleotide or polypeptide produced by the cell. In some exemplary embodiments an "endogenous" polypeptide or polynucleotide is encoded by the genome of the parental cell (or host cell). In other exemplary embodiments, an "endogenous" polypeptide or polynucleotide is encoded by an autonomously replicating plasmid carried by the parental cell (or host cell). In some exemplary embodiments, an "endogenous" gene is a gene that was present in the cell when the cell was originally isolated from nature i.e., the gene is "native to the cell". In other exemplary embodiments, an "endogenous" gene has been altered through recombinant techniques e.g., by altering the relationship of control and coding sequences. Thus, a "heterologous" gene may, in some exemplary embodiments, be "endogenous" to a host cell.

In contrast, an "exogenous" polynucleotide or polypeptide, or other substance (e.g., fatty acid derivative, small molecule compound, etc.) refers to a polynucleotide or polypeptide or other substance that is not produced by the parental cell and which is therefore added to a cell, a cell culture or assay from outside of the cell.

As used herein the term "native" refers to the form of a nucleic acid, protein, polypeptide or a fragment thereof that is isolated from nature or a nucleic acid, protein, polypeptide or a fragment thereof that is in its natural state without intentionally introduced mutations in the structural sequence and/or without any engineered changes in expression such as e.g., changing a developmentally regulated gene to a constitutively expressed gene.

As used herein, the term "fragment" of a polypeptide refers to a shorter portion of a full-length polypeptide or protein ranging in size from two amino acid residues to the entire amino acid sequence minus one amino acid residue. In certain embodiments of the disclosure, a fragment refers to the entire amino acid sequence of a domain of a polypeptide or protein (e.g., a substrate binding domain or a catalytic domain).

The term "gene" as used herein, refers to nucleic acid sequences e.g., DNA sequences, which encode either an RNA product or a protein product, as well as operably-linked nucleic acid sequences that affect expression of the RNA or protein product (e.g., expression control sequences such as e.g., promoters, enhancers, ribosome binding sites, translational control sequences, etc). The term "gene product" refers to either the RNA e.g., tRNA, mRNA and/or protein expressed from a particular gene.

The term "expression" or "expressed" as used herein in reference to a gene, refers to the production of one or more transcriptional and/or translational product(s) of a gene. In exemplary embodiments, the level of expression of a DNA molecule in a cell is determined on the basis of either the amount of corresponding mRNA that is present within the cell or the amount of protein encoded by that DNA produced by the cell. The term "expressed genes" refers to genes that are transcribed into messenger RNA (mRNA) and then translated into protein, as well as genes that are transcribed into other types of RNA, such as e.g., transfer RNA (tRNA), ribosomal RNA (rRNA), and regulatory RNA, which are not translated into protein.

The level of expression of a nucleic acid molecule in a cell or cell free system is influenced by "expression control sequences" or equivalently "regulatory sequences". "Expression control sequences" or "regulatory sequences" are known in the art and include, for example, promoters, enhancers, polyadenylation signals, transcription terminators, nucleotide sequences that affect RNA stability, internal ribosome entry sites (IRES), and the like, that provide for the expression of the polynucleotide sequence in a host cell. In exemplary embodiments, "expression control sequences"

interact specifically with cellular proteins involved in transcription (see e.g., Maniatis et al., *Science*, 236: 1237-1245 (1987); Goeddel, Gene Expression Technology: Methods in Enzymology, Vol. 185, Academic Press, San Diego, Calif. (1990)). In exemplary methods, an expression control sequence is operably linked to a polynucleotide sequence. By "operably linked" is meant that a polynucleotide sequence and an expression control sequence(s) are functionally connected so as to permit expression of the polynucleotide sequence when the appropriate molecules (e.g., transcriptional activator proteins) contact the expression control sequence(s). In exemplary embodiments, operably linked promoters are located upstream of the selected polynucleotide sequence in terms of the direction of transcription and translation. In some exemplary embodiments, operably linked enhancers can be located upstream, within, or downstream of the selected polynucleotide.

As used herein, the phrase "the expression of said nucleotide sequence is modified relative to the wild type nucleotide sequence", refers to a change e.g., an increase or decrease in the level of expression of an native nucleotide sequence or a change e.g., an increase or decrease in the level of the expression of a heterologous or non-native polypeptide-encoding nucleotide sequence as compared to a control nucleotide sequence e.g., wild-type control. In some exemplary embodiments, the phrase "the expression of said nucleotide sequence is modified relative to the wild type nucleotide sequence," refers to a change in the pattern of expression of a nucleotide sequence as compared to a control pattern of expression e.g., constitutive expression as compared to developmentally timed expression.

A "control" sample e.g., a "control" nucleotide sequence, a "control" polypeptide sequence, a "control" cell, etc., or value refers to a sample that serves as a reference, usually a known reference, for comparison to a test sample. For example, in an exemplary embodiment, a test sample comprises a non-native monounsaturated fatty acid derivative composition made by a viable recombinant bacterium that comprises a heterologous dual 3-hydroxy-acyl-ACP dehydratase/isomerase as disclosed herein, while the control sample comprises a non-native monounsaturated fatty acid derivative composition made by the corresponding or designated bacterium that does not comprise a heterologous dual 3-hydroxy-acyl-ACP dehydratase/isomerase. One of skill will recognize that controls can be designed for assessment of any number of parameters. Furthermore, one of skill in the art will understand which controls are valuable in a given situation and will be able to analyze data based on comparisons to control values.

The term "overexpressed" as used herein, refers to a gene whose expression is elevated in comparison to a "control" level of expression. In exemplary embodiments, "overexpression" of a gene is caused by an elevated rate of transcription as compared to the native transcription rate for that gene. In other exemplary embodiments, overexpression is caused by an elevated rate of translation of the gene compared to the native translation rate for that gene. Methods of testing for overexpression are well known in the art, for example transcribed RNA levels can be assessed using rtPCR and protein levels can be assessed using SDS page gel analysis.

In other embodiments, the polypeptide, polynucleotide, or hydrocarbon having an altered level of expression is "attenuated" or has a "decreased level of expression." As used herein, "attenuate" and "decreasing the level of expression" mean to express or cause to be expressed a polynucleotide, polypeptide, or hydrocarbon in a cell at a lesser concentration than is normally expressed in a corresponding control cell (e.g., wild type cell) under the same conditions.

A polynucleotide or polypeptide can be attenuated using any method known in the art. For example, in some exemplary embodiments, the expression of a gene or polypeptide encoded by the gene is attenuated by mutating the regulatory polynucleotide sequences which control expression of the gene. In other exemplary embodiments, the expression of a gene or polypeptide encoded by the gene is attenuated by overexpressing a repressor protein, or by providing an exogenous regulatory element that activates a repressor protein. In still other exemplary embodiments, DNA- or RNA-based gene silencing methods are used to attenuate the expression of a gene or polynucleotide. In some embodiments, the expression of a gene or polypeptide is completely attenuated, e.g., by deleting all or a portion of the polynucleotide sequence of a gene.

The degree of overexpression or attenuation can be 1.5-fold or more, e.g., 2-fold or more, 3-fold or more, 5-fold or more, 10-fold or more, or 15-fold or more. Alternatively, or in addition, the degree of overexpression or attenuation can be 500-fold or less, e.g., 100-fold or less, 50-fold or less, 25-fold or less, or 20-fold or less. Thus, the degree of overexpression or attenuation can be bounded by any two of the above endpoints. For example, the degree of overexpression or attenuation can be 1.5-500-fold, 2-50-fold, 10-25-fold, or 15-20-fold.

As used herein, "modified activity" or an "altered level of activity" of a protein/polypeptide in a recombinant host cell refers to a difference in one or more characteristics in the activity the protein/polypeptide as compared to the characteristics of an appropriate control protein e.g., the corresponding parent protein or corresponding wild type protein. Thus, in exemplary embodiments, a difference in activity of a protein having "modified activity" as compared to a corresponding control protein is determined by measuring the activity of the modified protein in a recombinant host cell and comparing that to a measure of the same activity of a corresponding control protein in an otherwise isogenic host cell. Modified activities can be the result of, for example, changes in the structure of the protein (e.g., changes to the primary structure, such as e.g., changes to the protein's nucleotide coding sequence that result in changes in substrate specificity, changes in observed kinetic parameters, changes in solubility, etc.); changes in protein stability (e.g., increased or decreased degradation of the protein) etc.

The term "heterologous" as used herein refers to a polypeptide or polynucleotide which is in a non-native state. In the context of a cell and a protein or cell and a polynucleotide the term "heterologous" refers to a polypeptide or a polynucleotide that is not native to the cell in which it is expressed/produced. Thus, a polynucleotide or a polypeptide is "heterologous" to a cell when the polynucleotide and/or the polypeptide and the cell are not found in the same relationship to each other in nature. Therefore, a polynucleotide or polypeptide sequence is "heterologous" to an organism or a second sequence if it originates from a different organism, different cell type, or different species, or, if from the same species, it is modified from its original form. Thus, in an exemplary embodiment, a polynucleotide or polypeptide is "heterologous" when it is not naturally present in a given organism. For example, a polynucleotide sequence that is native to cyanobacteria can be introduced into a host cell of *E. coli* by recombinant methods, and the polynucleotide from cyanobacteria is then heterologous to the *E. coli* cell (i.e., the now recombinant *E. coli* cell).

Similarly, a polynucleotide or polypeptide is "heterologous" when it is modified from its native form or from its relationship with other polynucleotide sequences or is present in a recombinant host cell in a non-native state. Thus, in an exemplary embodiment, a "heterologous" polynucleotide or polypeptide comprises two or more subsequences that are not found in the same relationship to each other in nature. For example, a promoter operably linked to a nucleotide coding sequence derived from a species different from that from which the promoter was derived. Alternatively, in another example, if a promoter is operably linked to a nucleotide coding sequence derived from a species that is the same as that from which the promoter was derived, then the operably-linked promoter and coding sequence are "heterologous" if the coding sequence is not naturally associated with the promoter (e.g. a constitutive promoter operably linked to a developmentally regulated coding sequence that is derived from the same species as the promoter). In other exemplary embodiments, a "heterologous" polynucleotide or polypeptide is modified relative to the wild type sequence naturally present in the corresponding wild type host cell, e.g., an intentional modification e.g., an intentional mutation in the sequence of a polynucleotide or polypeptide or a modification in the level of expression of the polynucleotide or polypeptide. Typically, a heterologous nucleic acid or polynucleotide is recombinantly produced.

The term "recombinant" as used herein, refers to a genetically modified polynucleotide, polypeptide, cell, tissue, or organism. When used with reference to a cell, the term "recombinant" indicates that the cell has been modified by the introduction of a heterologous nucleic acid or protein or has been modified by alteration of a native nucleic acid or protein, or that the cell is derived from a cell so modified and that the derived cell comprises the modification. Thus, for example, "recombinant cells" or equivalently "recombinant host cells" may be modified to express genes that are not found within the native (non-recombinant) form of the cell or may be modified to abnormally express native genes e.g., native genes may be overexpressed, underexpressed or not expressed at all. In exemplary embodiments, a "recombinant cell" or "recombinant host cell" is engineered to express a heterologous enzyme pathway capable of producing a bifunctional fatty acid derivative molecule. A recombinant cell can be derived from a microorganism such as a bacterium, a virus or a fungus. In addition, a recombinant cell can be derived from a plant or an animal cell. In exemplary embodiments, a "recombinant host cell" or "recombinant cell" is used to produce one or more non-native monounsaturated fatty acid derivatives including, but not limited to, non-native monounsaturated fatty acids, non-native monounsaturated fatty esters (e.g., waxes, fatty acid esters, fatty esters, fatty acid methyl esters (FAME), fatty acid ethyl esters (FAEE)), non-native monounsaturated fatty acyl acetate esters (FAce), non-native monounsaturated fatty alcohols (e.g., polyols), non-native monounsaturated fatty aldehydes, non-native monounsaturated fatty amines, non-native monounsaturated terminal olefins, non-native monounsaturated ketones, etc. Therefore, in some exemplary embodiments a "recombinant host cell" is a "production host" or equivalently, a "production host cell". In some exemplary embodiments, the recombinant cell includes one or more polynucleotides, each polynucleotide encoding a polypeptide having fatty acid biosynthetic enzyme activity, wherein the recombinant cell produces a non-native monounsaturated fatty acid derivative composition when cultured in the presence of a (simple) carbon source under conditions effective to express the polynucleotides.

When used with reference to a polynucleotide, the term "recombinant" indicates that the polynucleotide has been modified by comparison to the native or naturally occurring form of the polynucleotide or has been modified by comparison to a naturally occurring variant of the polynucleotide. In an exemplary embodiment, a recombinant polynucleotide (or a copy or complement of a recombinant polynucleotide) is one that has been manipulated by the hand of man to be different from its naturally occurring form. Thus, in an exemplary embodiment, a recombinant polynucleotide is a mutant form of a native gene or a mutant form of a naturally occurring variant of a native gene wherein the mutation is made by intentional human manipulation e.g., made by saturation mutagenesis using mutagenic oligonucleotides, through the use of UV radiation, mutagenic chemicals, chemical synthesis etc. Such a recombinant polynucleotide might comprise one or more point mutations, deletions and/or insertions relative to the native or naturally occurring variant form of the gene. Similarly, a polynucleotide comprising a promoter operably linked to a second polynucleotide (e.g., a coding sequence) is a "recombinant" polynucleotide. Thus, a recombinant polynucleotide comprises polynucleotide combinations that are not found in nature. A recombinant protein (discussed supra) is typically one that is expressed from a recombinant polynucleotide, and recombinant cells, tissues, and organisms are those that comprise recombinant sequences (polynucleotide and/or polypeptide).

As used herein, the term "microorganism" refers generally to a microscopic organism. Microorganisms can be prokaryotic or eukaryotic. Exemplary prokaryotic microorganisms include e.g., bacteria, archaea, cyanobacteria, etc. An exemplary bacterium is *Escherichia coli*. Exemplary eukaryotic microorganisms include e.g., yeast, protozoa, algae, etc. In exemplary embodiments, a "recombinant microorganism" is a microorganism that has been genetically altered and thereby expresses or encompasses a heterologous nucleic acid sequence and/or a heterologous protein.

The expression "viable bacterium" or "viable bacteria" or "viable microorganism" as used herein, refers to a bacterium that grows on a carbon source e.g., a simple carbon source, wherein the media used for culturing the microorganism does not contain any exogenous fatty acid or fatty acid derivative, nor any compound(s) that is/are an inhibitor of fatty acid biosynthesis, e.g., triclosan, which inhibits the fabI-type trans-2-enoyl-ACP reductase. Thus, a "viable recombinant bacterium" is a bacterium that has been altered by the hand of Man (recombinant) which grows on a carbon source, wherein the media used for culturing the bacterium does not contain any exogenous fatty acid or fatty acid derivative, nor any compound(s) that is/are an inhibitor of fatty acid biosynthesis. Typically, as used herein, a "viable recombinant bacterium" or "viable recombinant bacteria" comprises at least one heterologous dual 3-hydroxy-acyl-ACP dehydratase/isomerase that replaces the native dual 3-hydroxy-acyl-ACP dehydratase/isomerase.

Typically, a "viable recombinant bacterium" as disclosed herein will comprise within its cellular fatty acids/membrane phospholipids the non-native monounsaturated fatty acid (or fatty acid derivative) produced by the cell that has the characteristic double bond structure of the heterologous dual 3-hydroxy-acyl-ACP dehydratase/isomerase that replaces the native dual 3-hydroxy-acyl-ACP dehydratase/isomerase. In embodiments, the non-native monounsaturated fatty acid derivative comprises at least 5% of the membrane phospholipids. In another embodiment, the non-native monounsaturated fatty acid derivative comprises at least 10% of the membrane phospholipids. In still other embodiments, the non-native monounsaturated fatty acid derivative comprises at least 11%, at least 12%, at least 15%, at least 20%, at least 25%, at least 30%, at least 35%, at least 40%, of the membrane phospholipids.

A "production host" or equivalently a "production host cell" is a cell used to produce products. As disclosed herein, a "production host" is typically modified to express or overexpress selected genes, or to have attenuated expression of selected genes. Thus, a "production host" or a "production host cell" is a "recombinant host" or equivalently a "recombinant host cell". Non-limiting examples of production hosts include e.g., "viable recombinant bacteria" as disclosed above. An exemplary "production host" is a viable recombinant *Escherichia coli* cell comprising a heterologous dual 3-hydroxy-acyl-ACP dehydratase/isomerase.

The term "acetyl-CoA derived compound" refers to any compound or chemical entity (i.e., intermediate or end product) that is made via a biochemical pathway wherein acetyl-CoA functions as intermediate and/or is made upstream of the compound or chemical entity. For example, a acetyl-CoA derived compound may include, but is not limited to, a fatty acid derivative such as, for example, a fatty acid; a fatty ester including, but not limited to a fatty acid methyl ester (FAME) and/or a fatty acid ethyl ester (FAEE); a fatty alcohol; a fatty aldehyde; a fatty amine; an alkane; an olefin or alkene; a hydrocarbon; a 3-hydroxy fatty acid derivative, a bifunctional fatty acid derivative, a non-native monounsaturated fatty acid derivative, an unsaturated fatty acid derivative, etc.

As used herein, the terms "purify," "purified," or "purification" mean the removal or isolation of a molecule from its environment by, for example, isolation or separation. "Substantially purified" molecules are at least about 60% free (e.g., at least about 65% free, at least about 70% free, at least about 75% free, at least about 80% free, at least about 85% free, at least about 90% free, at least about 95% free, at least about 96% free, at least about 97% free, at least about 98% free, at least about 99% free) from other components with which they are associated. As used herein, these terms also refer to the removal of contaminants from a sample. For example, the removal of contaminants can result in an increase in the percentage of malonyl-CoA derived compounds including non-native monounsaturated fatty acid derivatives or other compounds in a sample. For example, when a malonyl-CoA derived compound including a non-native monounsaturated fatty acid derivative or other compound is produced in a recombinant host cell, the malonyl-CoA derived compound including the non-native monounsaturated fatty acid derivative or other compound can be purified by the removal of host cell proteins. After purification, the percentage of malonyl-CoA derived compounds including non-native monounsaturated fatty acid derivatives or other compounds in the sample is increased. The terms "purify," "purified," and "purification" are relative terms which do not require absolute purity. Thus, for example, when a malonyl-CoA derived compound (including a non-native monounsaturated fatty acid derivative disclosed herein or other compound) is produced in recombinant host cells, a malonyl-CoA derived compound (including a purified non-native monounsaturated fatty acid derivative or other compound) is a malonyl-CoA derived compound (including a non-native monounsaturated fatty acid derivative or other compound) that is substantially separated from other cellular components (e.g., nucleic acids, polypeptides, lipids, carbohydrates, or other hydrocarbons).

As used herein, the term "attenuate" means to weaken, reduce, or diminish. For example, a polypeptide can be attenuated by modifying the polypeptide to reduce its activity (e.g., by modifying a nucleotide sequence that encodes the polypeptide).

As used herein, the term "carbon source" refers to a substrate or compound suitable to be used as a source of carbon for prokaryotic or simple eukaryotic cell growth. Carbon sources can be in various forms, including, but not limited to polymers, carbohydrates, acids, alcohols, aldehydes, ketones, amino acids, peptides, and gases (e.g., CO and $CO_2$). Exemplary carbon sources include, but are not limited to, monosaccharides, such as glucose, fructose, mannose, galactose, xylose, and arabinose; oligosaccharides, such as fructo-oligosaccharide and galacto-oligosaccharide; polysaccharides such as starch, cellulose, pectin, and xylan; disaccharides, such as sucrose, maltose, cellobiose, and turanose; cellulosic material and variants such as hemicelluloses, methyl cellulose and sodium carboxymethyl cellulose; succinate, lactate, and acetate; alcohols, such as ethanol, methanol, and glycerol, or mixtures thereof. The carbon source can also be a product of photosynthesis, such as glucose. In certain embodiments, the carbon source is biomass. In other embodiments, the carbon source is glucose. In other embodiments the carbon source is sucrose. In other embodiments the carbon source is glycerol. In other embodiments, the carbon source is a simple carbon source such as e.g., glucose. In other embodiments, the carbon source is a renewable carbon source. In other embodiment, the carbon source is natural gas. In other embodiments the carbon source comprises one or more components of natural gas, such as methane, ethane, or propane. In other embodiments, the carbon source is flu gas or synthesis gas. In still other embodiments, the carbon source comprises one or more components of flu or synthesis gas such as carbon monoxide, carbon dioxide, hydrogen, etc. As used herein, the term "carbon source" or "simple carbon source" specifically excludes oleochemicals such as e.g., saturated or unsaturated fatty acids.

As used herein, the term "biomass" refers to any biological material from which a carbon source is derived. In some embodiments, a biomass is processed into a carbon source which is suitable for bioconversion. In other embodiments, the biomass does not require further processing into a carbon source. The carbon source can be converted into a composition comprising non-native monounsaturated fatty acid derivatives.

An exemplary source of biomass is plant matter or vegetation, such as corn, sugar cane, or switchgrass. Another exemplary source of biomass is metabolic waste products, such as animal matter (e.g., cow manure). Further exemplary sources of biomass include algae and other marine plants. Biomass also includes waste products from industry, agriculture, forestry, and households, including, but not limited to, glycerol, fermentation waste, ensilage, straw, lumber, sewage, garbage, cellulosic urban waste, and food leftovers (e.g., soaps, oils and fatty acids). The term "biomass" also can refer to sources of carbon, such as carbohydrates (e.g., monosaccharides, disaccharides, or polysaccharides).

I. Introduction

As discussed above, the molecular mechanism that *E. coli* and many other bacteria use to incorporate double bonds into fatty acid derivative molecules is well understood and serves as the paradigm for the "oxygen-independent" (anaerobic) monounsaturated fatty acid (mUFA) biosynthesis (see e.g., Magnuson et al. (1993) Appl. Microbial Rev. 57(3):522-542)

In particular, *E. coli* has two 3-hydroxy-acyl-ACP dehydratases, FabA and FabZ. FabA and FabZ differ in that FabZ catalyzes only the dehydratase reaction (see e.g., Mohan, S., et al. (1994) JBC Vol. 269, No. 52, Issue of December 30, pp. 32896-32903), whereas FabA, which is a dual function dehydratase/isomerase, also catalyzes isomerization of trans-2-decenoyl-ACP to cis-3-decenoyl-ACP (see e.g., Kass L. R., Bloch K. (1967) Proc. Natl. Acad. Sci. U.S.A 58:1168-1173).

The key enzyme for the "oxygen-independent" (anaerobic) mUFA synthesis is FabA. FabA isomerizes trans-2-decenoyl-ACP to cis-3-decenoyl-ACP. Cis-3-decenoyl-ACP cannot be reduced by trans-2-enoyl-ACP reductase (FabI) but can be elongated by β-keto-acyl-ACP synthase I (FabB) which fixes the double bond position in the ω-7 position (see e.g., FIG. 1). It is generally accepted that FabA from most bacteria is very specific for isomerizing trans-2-decenoyl-ACP and that this is the reason for predominantly ω-7 mUFAs in these bacteria.

That said, in some bacteria, the primary structure of dual 3-hydroxy-decanoyl-ACP dehydratase/isomerase is more closely related to fabZ-type dehydratases than to fabA-type dual function dehydratases/isomerases. For example, the dual function dehydratase/isomerase of *Enterococcus faecalis* is a fabZ homolog (see e.g., Wang and Cronan 2004, J. Biol. Chem. 279: 34489-34495).

Figure 2:
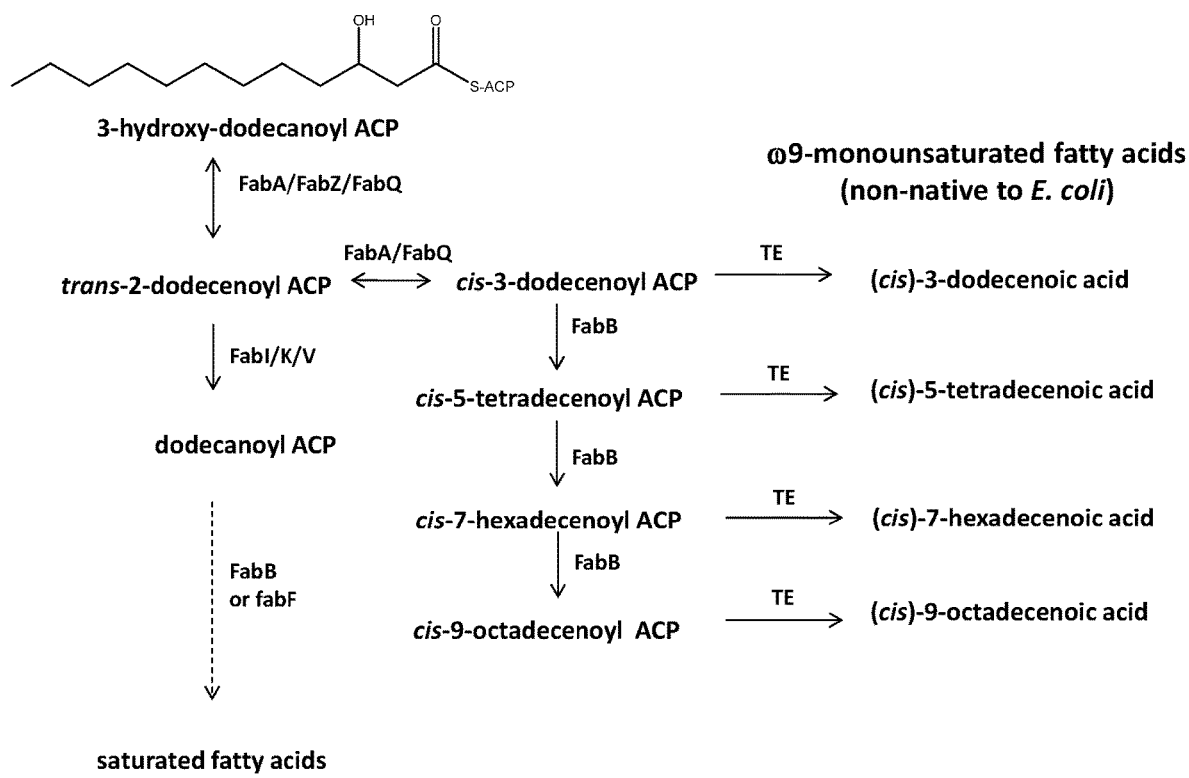
FIG. 2 Illustrates a biochemical pathway to produce $\omega$9-monounsaturated fatty acids.

Interestingly, bacterial enzymes having dual function dehydratase/isomerase function do not necessarily complement one another. For example, the dual function dehydratase/isomerase of *Aerococcus viridans* (which does not comprise a fabA homolog) is fabQ, which has low homology to fabZ (see e.g., Bi et al. (2013) *Chem. & Biol.* 20:1157-1167). FabQ isomerizes trans-2-dodecenoyl-ACP to cis-3-dodecenoyl-ACP thereby incorporating the double bond into the ω9 position (see FIG. 2) and demonstrating that FabQ is a dual 3-hydroxy-acyl-ACP dehydratase/isomerase.

However, even though FabQ is a dual 3-hydroxy-acyl-ACP dehydratase/isomerase, fabQ can not functionally replace FabA in *E. coli*. This was tested experimentally in recombinant *E. coli* strains which had deletions in the fabA gene and which overexpressed the fabQ gene from *A. viridans*. Such recombinant *E. coli* strains were not viable and required supplementation of oleic acid to the media for growth. Moreover, only small amounts of ω9-mUFA could be detected in the recombinant *E. coli* and only when a very sensitive radioactive labeling method was employed and only in the presence of triclosan, a known inhibitor of *E. coli*'s trans-2-enoyl-ACP reductase (FabI) (see e.g., Bi et al. (2013) supra). Thus, despite the fact that fabQ is a dual 3-hydroxy-acyl-ACP dehydratase/isomerase it could not function in this role in *E. coli*.

Since enzymes having dual 3-hydroxy-acyl-ACP dehydratase/isomerase activity are not necessarily interchangeable, it appears that it is no simple matter to engineer bacteria to produce non-native monounsaturated fatty acids and fatty acid derivatives using such a mechanism.

An alternative approach to incorporate double bonds in non-native positions of an acyl chain is the use of certain desaturases, which are oxygen-dependent, require additional redox partners and can regioselectively incorporate cis-double bonds into acyl chains, e.g. acyl-CoAs, acyl-ACPs or within membrane phospolipids. For example the 45 desaturase from *Bacillus subtilis* and the Δ6-(16:0)-ACP desaturase from *Thunbergia alata* have been expressed in *E. coli* to create membrane phospholipids with non-native monunsaturation (Bonamore et al., J. Biotechnol. 2006, vol. 121: 49-53; Cahoon et al., J. Bacteriol. 1996, vol. 178: 936-939). However, such approaches have worked only poorly and can only be applied under high oxygen conditions, which is undesirable in many biotechnological production processes.

Therefore, since monounsaturated fatty acids and fatty acid derivatives are the basis for many different nutritional products, as well as flavors, fragrances and fuel (e.g., biodiesel) what is needed in the art are methods for making these compounds that meet the needs of industry. As bacterial systems are the workhorse of industrial biotechnology, a need exists for bacteria e.g., *E. coli*, that are capable of producing "tailored," mUFAs having a double bond in the ω-3, ω-4, ω-5, ω-6, ω-8, ω-9, ω-10, ω-11, ω-12, etc. positions as well as in the native ω-7, position. Fortunately, the instant disclosure provides for this and other needs.

II. Bacteria that Produce Non-Native Monounsaturated Fatty Acid Derivative Molecules A. General Methods This disclosure utilizes routine techniques in the field of recombinant genetics. Basic texts disclosing the general methods and terms in molecular biology and genetics include e.g., Sambrook et al., *Molecular Cloning, a Laboratory Manual*, Cold Spring Harbor Press 4th edition (Cold Spring Harbor, N.Y. 2012); Current Protocols in Molecular Biology Volumes 1-3, John Wiley & Sons, Inc. (1994-1998). This disclosure also utilizes routine techniques in the field of biochemistry. Basic texts disclosing the general methods and terms in biochemistry include e.g., *Lehninger Principles of Biochemistry* sixth edition, David L. Nelson and Michael M. Cox eds. W.H. Freeman (2012). This disclosure also utilizes routine techniques in industrial fermentation. Basic texts disclosing the general methods and terms in fermentation include e.g., *Principles of Fermentation Technology*, 3rd Edition by Peter F. Stanbury, Allan Whitaker and Stephen J. Hall. Butterworth-Heinemann (2016); *Fermentation Microbiology and Biotechnology*, 2nd Edition, E. M. T. El-Mansi, C. F. A. Bryce, Arnold L. Demain and A. R. Allman eds. CRC Press (2007). This disclosure also utilizes routine techniques in the field of organic chemistry. Basic texts disclosing the general methods and terms in organic chemistry include e.g., *Practical Synthetic Organic Chemistry: Reactions, Principles, and Techniques*, Stephane Caron ed., John Wiley and Sons Inc. (2011); *The Synthetic Organic Chemist's Companion*, Michael C. Pirrung, John Wiley and Sons Inc. (2007); *Organic Chemistry*, 9th Edition—Francis Carey and Robert Giuliano, McGraw Hill (2013).

For nucleic acids, sizes are given in either kilobases (kb) or base pairs (bp). Estimates are typically derived from agarose or acrylamide gel electrophoresis, from sequenced nucleic acids, or from published DNA sequences. For proteins, sizes are given in kilodaltons (kDa) or amino acid residue numbers. Protein sizes may be estimated from gel electrophoresis, from sequenced proteins, from derived amino acid sequences, or from published protein sequences.

Oligonucleotides that are not commercially available can be chemically synthesized e.g., according to the solid phase phosphoramidite triester method first described by Beaucage & Caruthers, Tetrahedron Letts. 22:1859-1862 (1981), using an automated synthesizer, as described in Van Devanter et al., Nucleic Acids Res. 12:6159-6168 (1984). Purification of oligonucleotides is e.g., by either native acrylamide gel electrophoresis or by anion-exchange HPLC as described in Pearson & Reanier, J. Chrom. 255:137-149 (1983).

The sequence of cloned genes and synthetic oligonucleotides can be verified after cloning using, e.g., the chain termination method for sequencing double-stranded templates of Wallace et al., Gene 16:21-26 (1981).

B. Bacteria that Produce Non-Native Monounsaturated Fatty Acids Derivative Molecules in Different Positions In an exemplary embodiment, the disclosure provides recombinant bacteria that produce non-native monounsaturated fatty acids derivatives wherein the double bond is present in different positions. Some examples of microorganisms with the predominant double-bond position other than ω7 in their cellular fatty acids are shown in Table 1. Taxonomic Classification of Bacteria is known in the art see e.g., *Taxonomic Outline of Bacteria and Archaea*, Michigan State University (2007), George M. Garrity ed.; *Bergey's Manual of Systematic Bacteriology*, George M. Garrity ed: Springer, New York, 2005, Volume 2: The Proteobacteria, Part B: The Gammaproteobacteria.

However, as the present inventors disclose herein, viable recombinant bacteria comprising a heterologous dual 3-hydroxy-acyl-ACP dehydratase/isomerase enzyme have been constructed wherein the heterologous dual 3-hydroxy-acyl-ACP dehydratase/isomerase enzyme replaces the native enzyme e.g., native fabA.

In particular, as shown herein below, a fabA-type dual 3-hydroxy-acyl-ACP dehydratase/isomerase from a microorganism belonging to the taxonomic class of "Gammaproteobacteria" (e.g. *Marinobacter* ssp.) was able to functionally complement the fabA-type dual 3-hydroxy-acyl-ACP dehydratase/isomerase from another microorganism belonging to the taxonomic class of "Gammaproteobacteria" (e.g. *E. coli*). Thus, similarity of the fatty acid biosynthetic machinery within the "Gammaproteobacteria" allows for cross complementation of fabA-type dual 3-hydroxy-acyl-

TABLE 1

Examples of bacteria with the double bond in unusual position in their cellular fatty acids and the putative 3-hydroxyacyl-ACP dehydratase genes in their genomes

| microorganism | Taxonomic classification (Class) | predominant double bond position in mUFA | fabA homolog | fabZ homolog | fabQ homolog |
|---|---|---|---|---|---|
| *Escherichia coli* | Gammaproteobacteria | ω7 | NP_415474 | NP_414722 | none |
| *Enterococcus faecalis* | Firmicutes | ω7 | none | NP_816498 NP_814076 | none |
| "unusual" double bond position | | | | | |
| *Aerococcus viridans* | Firmicutes | ω9 | none | none | WP_070467837 |
| *Jeotgalibaca dankookensis* | Firmicutes | ω9 | none | none | WP_062471723 |
| *Paraclostridium benzoelyticum* | Firmicutes | ω9 | none | none | WP_046822481 |
| *Marinobacter aquaeolei* | Gammaproteobacteria | ω9 | WP_011786589 | HCP19805 | none |
| *Marinobacter segnicrescens* | Gammaproteobacteria | ω9 | WP_091850164 | WP_091854130 | none |
| *Marinobacter nanhaiticus* | Gammaproteobacteria | ω9 | WP_004580667 | WP_004581673 | none |
| *Marinobacter similis* | Gammaproteobacteria | ω7 or ω9 | WP_041339271 | WP_041342533 | none |
| *Alcanivorax borkumensis* | Gammaproteobacteria | ω9 | WP_011588119 | WP_035458334 | none |
| *Oleiphilus messinensis* | Gammaproteobacteria | ω7 or ω9 | Ga0198489_113772 Ga0198489_112592 | Ga0198489_111977 | none none |
| *Leucothrix pacifica* | Gammaproteobacteria | ω9 | one* | one* | none* |
| *Methylomonas lenta* | Gammaproteobacteria | ω6 or ω7 | WP_066979795 | WP_066979280 | none |
| *Zavarzinella formosa* | Planctomycetes | ω5 | none | WP_020473045 WP_020473048 WP_020469995 | none |
| *Mucilaginibacter paludis* | Bacteroidetes | ω5 | none | WP_008512849 WP_040625927 | none |
| *Marichromatium bheemlicum* | Gammaproteobacteria | ω5 | one* | one* | none* |
| *Marichromatium indicum* | Gammaproteobacteria | ω5 | one* | one* | none* |

*fabA/Z/Q sequences are unknown, number of genes is deduced from the closely related Leucothrix mucor or Marichromatium gracile genomes As discussed above, not every dual 3-hydroxy-acyl-ACP dehydratase/isomerase can substitute for another dual 3-hydroxy-acyl-ACP dehydratase/isomerase. In particular, the fabQ-type dual 3-hydroxy-acyl-ACP dehydratase/isomerase from a microorganism belonging to the taxonomic class of "Firmicutes" (e.g. *Aerococcus viridans*) was not able to functionally complement the fabA-type dual dehydratase/isomerase from a microorganism belonging to the taxonomic class of "Gammaproteobacteria" (e.g. *E. coli*) see e.g., Bi et al (2013) supra.

ACP dehydratase/isomerases, even though they dehydrate and isomerize different intermediates of fatty acid biosynthesis, e.g., 3-hydroxydecanoyl-ACP leading to ω7-mUFA or 3-hydroxydodecanoyl-ACP leading to ω9-mUFA or 3-hydroxyoctanoyl-ACP leading to ω5-mUFA, etc. Therefore, reprograming of the fatty acid biosynthetic machinery of a microorganism such as *E. coli* to produce non-native monounsaturated fatty acids is successful when a fabA-type dual dehydratase/isomerase from another Gammaproteobacteria is employed.

Therefore, without being bound by theory, it is believed that a heterologous dual 3-hydroxy-acyl-ACP dehydratase/isomerase derived from a microorganism whose overall fatty acid biosynthesis machinery (the fab genes) resembles that of the host microorganism may be interchanged with the host enzyme(s) to provide viable recombinant bacteria that efficiently produce non-native mUFAs which have the characteristic double bond structure of the heterologous enzyme rather than that of the host.

Thus, for example, as demonstrated herein, the fabA homologs of bacteria whose overall fatty acid biosynthesis machinery (the fab genes) resembles that of *E. coli* are interchanged with the *E. coli* enzyme(s) to provide viable recombinant bacteria that efficiently produce non-native mUFAs which have the characteristic double bond structure of the heterologous enzyme. Similarities of fatty acid biosynthesis machinery have been reviewed (see e.g., Beld, J., et al., Mol Biosyst. 2015 Jan. 2; 11(1): 38-59; see also Taxonomic Outline of Bacteria and Achaea supra).

Exemplary gamma-proteobacteria with unusual monounsaturated fatty acids include e.g., *Marinobacter* ssp., *Alcanivorax borkumensis*, *Oleiphilus messinensis*, *Leucothrix pacifica*, *Marichromatium bheemlicu*, *Marichromatium indicum* (see e.g., Table 1).

However, a fabZ-type or fabQ-type dual 3-hydroxy-acyl-ACP dehydratase/isomerase or a fabA-type dual 3-hydroxy-acyl-ACP dehydratase/isomerase from an unrelated organism can still be employed to produce non-native monounsaturated fatty acids in a microorganism such as *E. coli*. For this to be successful, additional engineering of the *E. coli* fatty acid biosynthetic machinery, e.g. replacing or engineering the enoyl-ACP reductase (FabI), a β-ketoacyl-ACP synthase (FabB or fabF), the 3-hydroxy acyl-ACP dehydratase (FabZ) or the acyl carrier protein (ACP), or combinations thereof to be compatible with the heterologous dual 3-hydroxy-acyl-ACP dehydratase/isomerase is carried out. See e.g., Examples 8 and 9.

Relationships Between FabA, FabZ and FabQ

In general, a fabA-type dual 3-hydroxy-acyl-ACP dehydratase/isomerase is an enzyme that shows highest sequence similarity to another fabA-type enzyme, e.g. fabA from *E. coli* (UniProtKB—P0A6Q3) and not to a fabZ-type or fabQ-type enzyme. For example, for a microorganism that has a fabA-type and a fabZ-type enzyme, the fabA-type enzyme will have greater sequence similarity to a fabA-type enzyme from another microorganism than to its own fabZ-type enzyme (note that most microorganisms with a fabA-type enzyme also have a fabZ-type enzyme).

Similarly, a fabZ-type dual 3-hydroxy-acyl-ACP dehydratase/isomerase is an enzyme that shows highest sequence simlarity to another fabZ-type enzyme, e.g. fabZ1 from *Enterococcus faecalis* (UniProtKB—Q820V3), and not to a fabA or fabQ enzyme. For example, for a microorganism that has a fabZ-type and a fabA-type enzyme, the fabZ-type enzyme have greater sequence similarity and therefore will be more homologous to a fabZ-type enzyme from another microorganism than to its own fabA-type enzyme (note that not all microorganisms with a fabZ-type enzyme have a fabA-type enzyme).

Similarly, a fabQ-type dual 3-hydroxy-acyl-ACP dehydratase/isomerase is an enzyme that shows highest sequence similarity/homology to another fabQ-type enzyme, e.g. fabQ from *Aerococcus viridans* (UniProtKB—A0A2J9PPT2) (note that most microorganisms with a fabQ-type enzyme do not have a fabA- or fabZ-type enzyme).

The use of sequence similarly to identify homology is known in the art see e.g., Pearson W, R. (2013) Curr Protoc Bioinformatics. 2013 June; 0 3: doi:10.1002/0471250953.bi0301s42; Ladunga, I. Curr Protoc Bioinformatics. 2003 February: Chapter 3:Unit 3.4; Ladunga, I. Curr Protoc Bioinformatics. 2017 Sep. 13:59:3.4.1-3.4.24.

Recombinant Bacteria that Produce a Non-Native Monounsaturated Fatty Acid Derivatives Having a Double Bond in the Omega-9 (ω-9) Position As is shown in detail below, fabA genes from different *Marinobacter* species were transformed into *E. coli* replacing the native fabA gene. The transformed cells were viable even though the native *E. coli* fabA was replaced and the heterologous enzyme was able to efficiently isomerize trans-2-dodecenoyl-ACP to cis-3-dodecenoyl-ACP thereby fixing the double bond in the ω-9 position (see FIG. 2).

*Marinobacter* ssp. comprise mUFA with predominantly ω-9 double bonds (see e.g. Huu et al. (1999) *Int. J. System. Evol. Microbiol.* 49:367-375). As is demonstrated herein, recombinant bacteria e.g., *E. coli*, which comprise a heterologous a *Marinobacter* dual 3-hydroxy-acyl-ACP dehydratase/isomerase produce mUFAs having the double bond in the ω-9 position, characteristic of the *Marinobacter* enzyme (see e.g., Examples 2-6, below).

As is disclosed in detail in the Examples below, *E. coli* were engineered such that the fabA gene from a *Marinobacter* species replaced the native *E. coli* fabA gene. In contrast to strains engineered with fabQ from *Aerococcus viridans* (discussed above), the resulting strains (e.g. *E. coli* ΔfabA::fabA_Maqu) were viable, did not require oleic acid supplementation and synthesized predominantly w 9-mUFAs without the need of inhibiting trans-2-enoyl-ACP reductase activity. Thus, non-native monounsaturated fatty acid derivatives having ω-9 double bonds were produced in *E. coli*.

Figure 3:
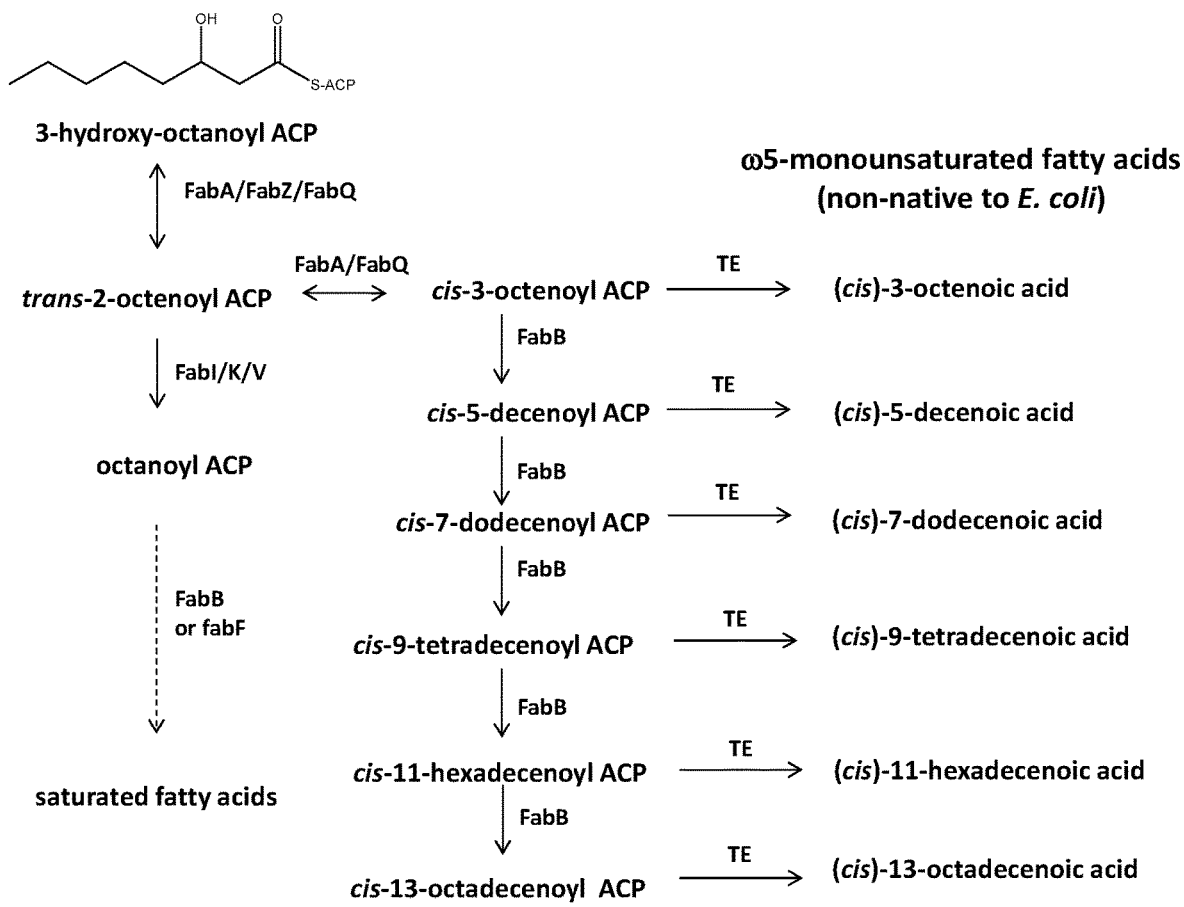
FIG. 3 Illustrates a biochemical pathway to produce ω5-monounsaturated fatty acids.

Recombinant Bacteria that Produce a Non-Native Monounsaturated Fatty Acid Derivatives Having a Double Bond in the Omega-5 (ω-5) Position In embodiments, recombinant microorganisms are constructed which produce predominantly non-native ω5-monounsaturated fatty acids within their cellular fatty acids. Microorganisms with predominantly ω5-monounsaturated fatty acids within their cellular fatty acids have a dual 3-hydroxyacyl-ACP dehydratase/isomerase (e.g. a homolog of fabA or fabZ or fabQ) that isomerizes trans-2-octenoyl-ACP to cis-3-octenoyl-ACP (see e.g., Table 1). When such a dual 3-hydroxyacyl-ACP dehydratase/isomerase is heterologously expressed in a compatible bacterium that naturally produces ω7-monounsaturated fatty acids (e.g. *E. coli*, FIG. 1), this recombinant bacterium produces non-native ω5-monounsaturated fatty acids (see e.g., FIG. 3 and Examples 8 and 9)

Recombinant Bacteria that Produce a Non-Native Monounsaturated Fatty Acid Derivatives Having a Double Bond in the Omega-3 (ω-3) Position In embodiments, recombinant microorganisms are constructed which produce predominantly non-native ω3-monounsaturated fatty acids within their cellular fatty acids. Microorganisms with ω3-monounsaturated fatty acids within their cellular fatty acids have a dual 3-hydroxyacyl-ACP dehydratase/isomerase (e.g. a homolog of fabA or fabZ or fabQ) that isomerizes trans-2-hexenoyl-ACP to cis-3-hexenoyl-ACP (see e.g., PKS genes Table 2). When such a dual 3-hydroxyacyl-ACP dehydratase/isomerase is heterologously expressed in a compatible bacterium that naturally produces ω7-monounsaturated fatty acids (e.g. *E. coli*, FIG. 2), the resultant recombinant bacterium produces non-native ω3-monounsaturated fatty acids (see e.g., FIG. 4 and Example 10).

Figure 5:
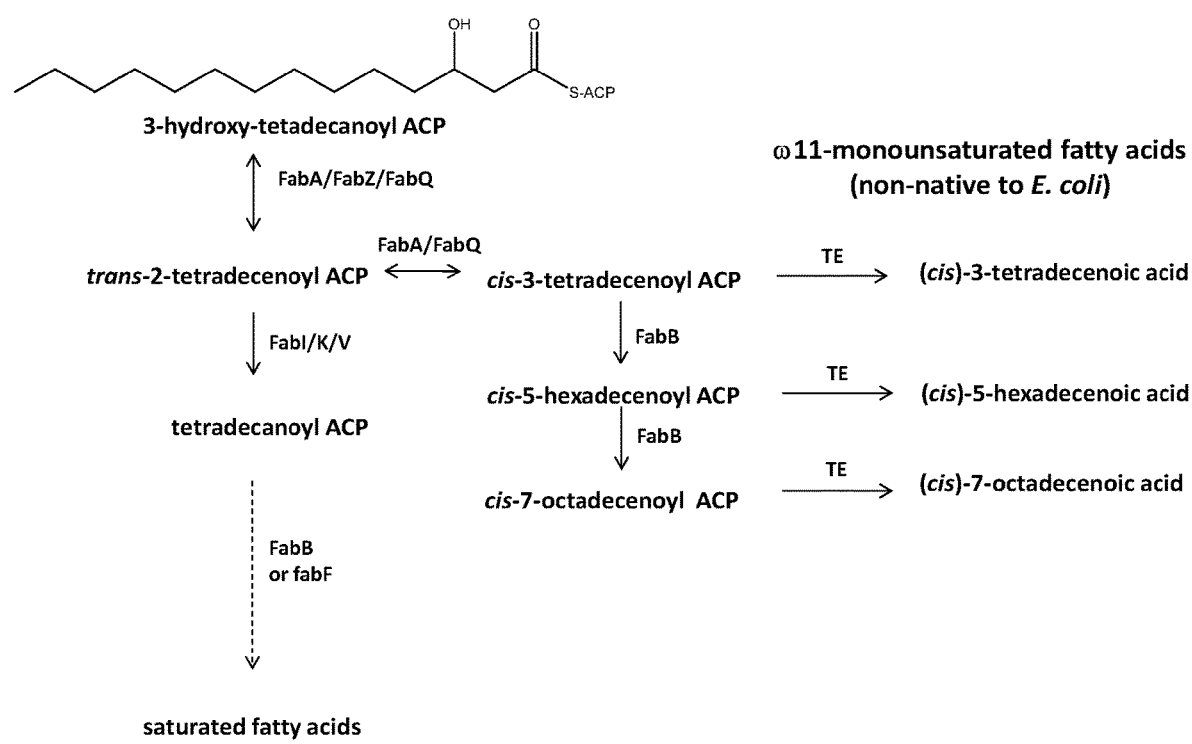
FIG. 5 Illustrates a biochemical pathway to produce ω11-monounsaturated fatty acids.

Recombinant Bacteria that Produce a Non-Native Monounsaturated Fatty Acid Derivatives Having a Double Bond in the Omega-11 (ω-11) Position In embodiments, a microorganism with predominantly cull-monounsaturated fatty acids within its cellular fatty acids has a dual 3-hydroxyacyl-ACP dehydratase/isomerase (e.g. a homolog of fabA or fabZ or fabQ) that isomerizes trans-2-tetradecenoyl-ACP to cis-3-tetradecenoyl—ACP. When such a dual 3-hydroxyacyl-ACP dehydratase/isomerase is heterologously expressed in a compatible bacterium that naturally produces ω7-monounsaturated fatty acids (e.g. *E. coli*, FIG. 2), the resultant recombinant bacterium produces non-native cull-monounsaturated fatty acids (FIG. 5).

Figure 6:
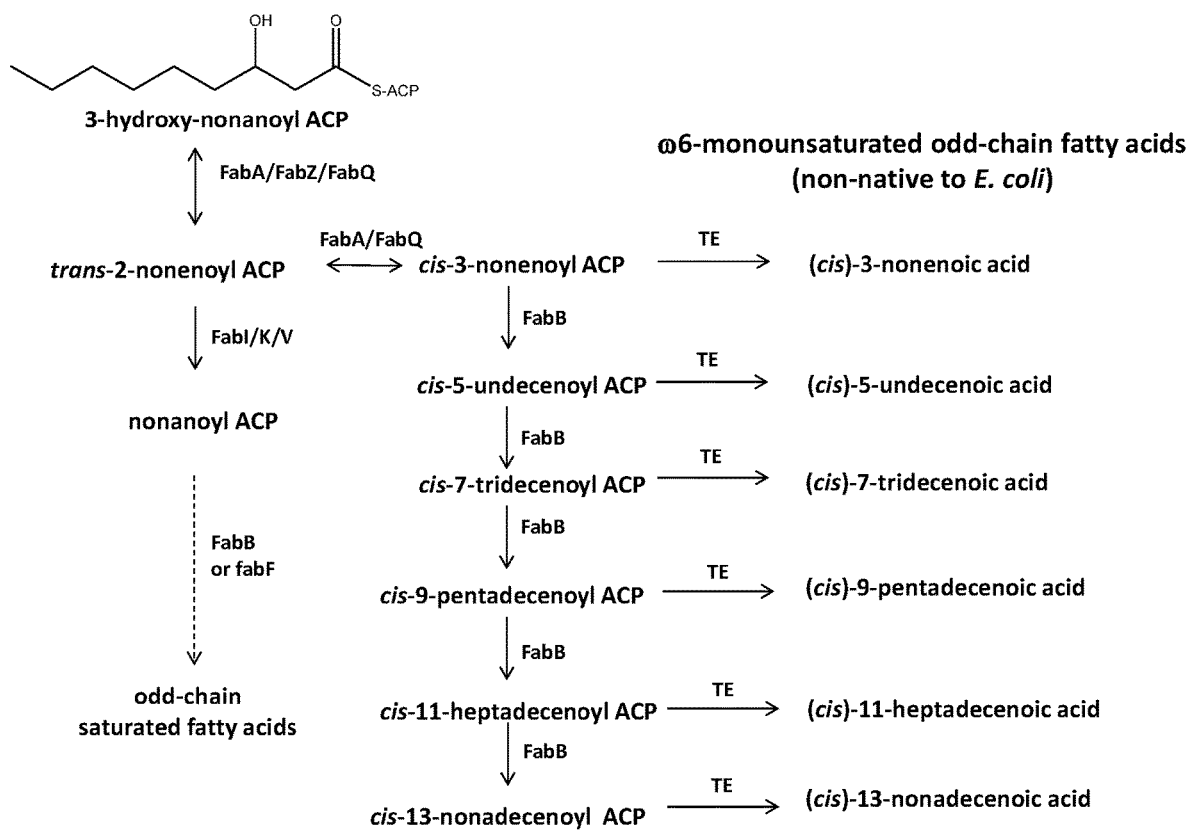
FIG. 6 Illustrates a biochemical pathway to produce ω6-monounsaturated fatty acids.
Figure 7:
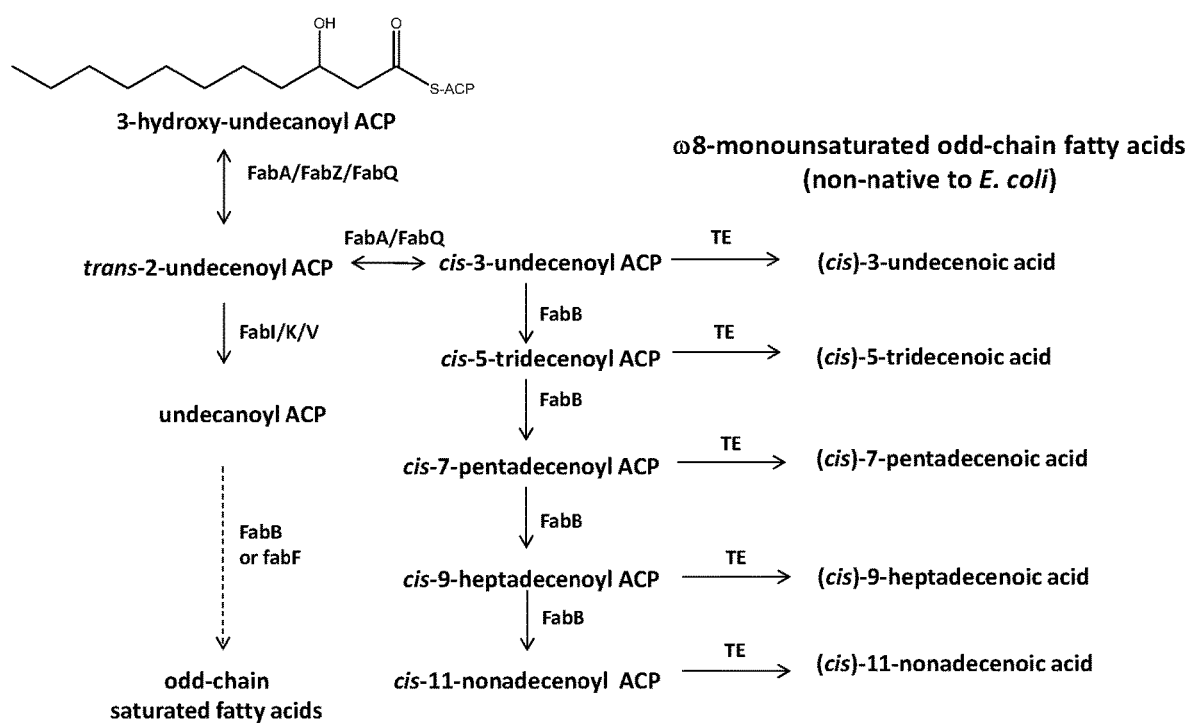
FIG. 7 Illustrates a biochemical pathway to produce ω8-monounsaturated fatty acids.

Recombinant Bacteria that Produce a Non-Native Monounsaturated Fatty Acid Derivatives Wherein the Carbon Chain has an Odd-Number of Carbons and the Double Bond is in an Even-Numbered Positon Fatty acid derivatives having double bonds in "odd-numbered" position in their non-native monounsaturated fatty acids, e.g. ω3, ω5, ω9 and ω11 typically have even-numbered carbon chains e.g. C12, C14, C16, C18, etc. When recombinant bacteria that produce odd-chain fatty acids (see e.g. U.S. Pat. No. 8,372,610), heterologously express a compatible dual 3-hydroxyacyl-ACP dehydratase/isomerase (e.g. a homolog of fabA or fabZ or fabQ) then depending on the substrate specificity of the heterologous dual 3-hydroxyacyl-ACP dehydratase/isomerase, non-native monounsaturated fatty acids with the double-bond in even-numbered position can be produced, e.g. ω4, ω6, ω8, ω10, ω12, etc. (see e.g., FIG. 6 and FIG. 7).

Recombinant Bacteria Comprising a Heterologous Dual 3-Hydroxyacyl-ACP Dehydratase/Isomerases from Modular Polyketide Synthase (PKS) Gene Clusters In some embodiments, suitable heterologous dual 3-hydroxyacyl-ACP dehydratase/isomerases are part of modular polyketide synthase (PKS) gene clusters from microorganisms that produce polyunsaturated fatty acids (PUFAs) using an oxygen-independent ("anaerobic") mechanism via such PKS (Metz et al. 2001, *Science* vol. 293, pp. 290; Okuyama et al. 2007, *Appl. Environ. Microbiol.* vol. 73, pp. 665).

Figure 4:
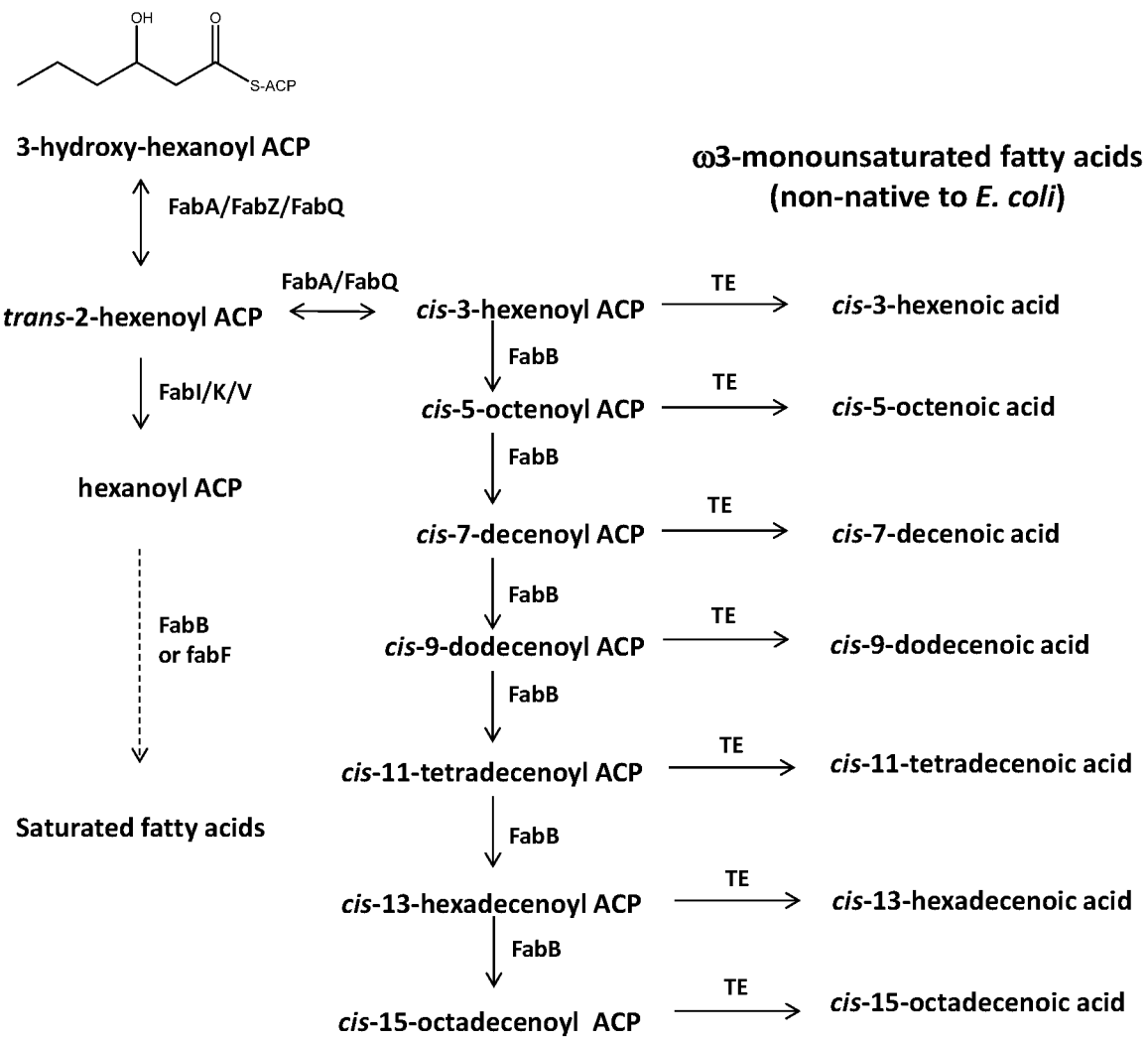
FIG. 4 Illustrates a biochemical pathway to produce ω3-monounsaturated fatty acids.

Polyketide synthases have dehydratase domains with homology to fabA-type dual 3-hydroxyacyl-ACP dehydratase/isomerases, and are responsible for incorporating up to six double bonds into polyunsaturated fatty acids (PUFAs). The first dehydration/isomerization leading to a PUFA occurs at the 3-hydroxyhexenoyl-ACP step leading to an ω-3 double bond in the growing fatty acyl chain. This step occurs before any other double bonds are integrated (Metz et al. 2001, *Science* vol. 293, pp. 290) (see also FIG. 4). Thus, in embodiments, when such a PKS dual 3-hydroxyacyl-ACP dehydratase/isomerase domain or didomain is heterologously expressed in a compatible bacterium that naturally produces ω7-monounsaturated fatty acids (e.g. *E. coli*, FIG. 1 and Example 10), the resultant recombinant bacterium produces non-native ω3-monounsaturated fatty acids (FIG. 4).

Exemplary polyketide synthases with fabA-type dual 3-hydroxyacyl-ACP dehydratase/isomerase domains are provided in Table 2. Polyketide synthases typically have fabA-type didomains, i.e. two fabA-like domains are present in tandem in such polyketide synthases (see e.g., Oyola Robles et al. 2013, Prot. Science vol. 22, pp. 954; Xie et al. 2018, Appl. Micobiol. Biotechnol. vol. 102, pp. 847).

Therefore, in embodiments, recombinant microorganisms are constructed which produce predominantly non-native ω-3 monounsaturated fatty acids within its cellular fatty acids. Microorganisms with predominantly PUFAs within its cellular fatty acids have a modular polyketide synthase (PKS) (e.g. a homolog of fabA). When a fabA-type domain or didomain from such a modular polyketide synthase (PKS) is heterologously expressed in a compatible bacterium that naturally produces ω7-monounsaturated fatty acids (e.g. *E. coli*, FIG. 1), the resultant recombinant bacterium produces non-native ω-3 monounsaturated fatty acids (see e.g., FIG. 4 and Example 10).

TABLE 2

Examples of polyketide synthases with fabA-type dual 3-hydroxyacyl-ACP dehydratase/isomerase didomains

| Microorganism | PKS with fabA-type didomain | Accession number |
|---|---|---|
| *Shewanella* sp. SCR2738 | orf7 | AB025342 |
| *Shewanella oneidensis* MR-1 | PfaC | WP_011071757 |
| *Photobacterium profundum* | PfaC | AF409100 |
| *Montella marina* MP-1 | PfaC | AB025342 |
| *Schizochtrium* sp. | orfC | AF378329 |
| *Thraustochytrium* sp. 26185 | orfC | AOG21006 | g. Additional Heterologous Fatty Acid Biosynthetic Genes

In embodiments, providing other heterologous elements of biosynthetic machinery further improve the ability of recombinant microbial cells to produce fatty acid derivatives having double bonds in non-native positions.

As disclosed in detail in the Examples below, experiments show that when recombinant *E. coli* cells having a heterologous *Marinobacter* dual 3-hydroxy-acyl-ACP dehydratase/isomerase are further transformed so as to replace the native *E. coli* 3-hydroxyacyl-ACP dehydratase, fabZ, with a heterologous 3-hydroxyacyl-ACP dehydratase, fabZ, from the respective *Marinobacter* species, the recombinant cells show improved growth and production of ω9-mUFA (e.g. *E. coli* ΔfabA::fabA_Maqu and ΔfabZ::fabZ_Maqu). Therefore, efficient production of non-native mUFA in *E. coli* benefits from the expression of heterologous fabZ-type 3-hydroxyacyl-ACP dehydratases.

Similarly, in embodiments efficient production of non-native mUFA in *E. coli* is improved by expressing heterologous trans-2-enoyl-ACP reductases (EC 1.3.1.10, EC 1.3.1.10, EC 1.3.1.38, EC 1.3.1.39, EC 1.3.1.104), e.g. FabK-type trans-2-enoyl-ACP reductases (Marrakchi et al. 2003, *Biochem. J.* 370:1055-1062), FabV-type trans-2-enoyl-ACP reductases (Massengo-Tiasse & Cronan 2008, J. Biol. Chem. 283: 1308-1316), FabI-type trans-2-enoyl-ACP reductases (Bergeler et al. 1994, J. Biol. Chem. 269: 5493-5496) or FabL-type trans-2-enoyl-ACP reductases (Heath et al. 2000, J. Biol. Chem. 275: 40128-40133).

In other embodiments, efficient production of non-native mUFA in *E. coli* is improved by expression of heterologous β-ketoacyl-ACP synthases (also known as 3-oxoacyl-ACP synthases) (EC 2.3.1.42, EC 2.3.1.179, EC 2.3.1.180), e.g. FabB-type KASI enzymes or fabF-type KASII enzymes (Garwin et al. 1980, J. Biol. Chem. 255: 3263-3265).

2. Assaying for Non-Native Monounsaturated Fatty Acid Derivative Molecules

In exemplary embodiments, non-native monounsaturated fatty acid derivatives are identified by assaying for the production of non-native monounsaturated fatty acid derivatives (e.g., an ω3-monounsaturated fatty acid, an ω5-monounsaturated fatty acid, ω9-monounsaturated fatty acid, ω11-monounsaturated fatty acid, etc.) by a recombinant microbial host strain. In exemplary embodiments, Gas- Chromatography with Flame-Ionization Detection (GC-FID) is used to assay the non-native monounsaturated fatty acid derivative. GC-FID is known in the art (see e.g., Adlard, E. R.; Handley, Alan J. (2001). *Gas chromatographic techniques and applications*. London: Sheffield Academic). However, any appropriate method for quantitation and analysis may be used e.g., mass spectrometry (MS), Gas Chromatography-mass spectrometry (GC-MS), liquid chromatography-mass spectrometry (LC-MS), thin layer chromatography (TLC), etc.

The position of the double bond can be confirmed e.g., either by using authentic standards or by GC/MS of their dimethyl disulphide (DMDS) adducts (see e.g., Nichols et al. 1986, J. Microbiol. Methods 5: 49-55).

3. Non-Native Monounsaturated Fatty Acid Derivative Molecules as Building Blocks for Flavors Fragrances and Other Uses Non-native monounsaturated fatty acid derivative molecules such as the non-native monounsaturated fatty acid derivatives disclosed herein have applications as e.g., fragrances, flavors, nutritional supplements, fuel and etc.

Thus, in some embodiments, non-native monounsaturated fatty acid derivatives disclosed herein are used alone or in combination with other molecules to provide renewable fuels and/or fragrances and flavors for the production of perfume, food, drink, toiletries, etc, nutritional supplements, industrial chemicals, etc (see e.g., International Patent Application Publication WO 2015/157719 A9).

II. Preparation of Non-Native Monounsaturated Fatty Acid Derivatives Molecules

1. Introduction

Monounsaturated fatty acid derivatives as disclosed herein are typically made using recombinant host cells e.g., using bacterial cells e.g., *E. coli* cells, that are engineered as disclosed herein to produce non-native monounsaturated fatty acid derivatives molecules. Accordingly, as disclosed herein, recombinant host cells are engineered and constructed to utilize nucleic acids and their corresponding polypeptides of enzymatic function in order to provide heterologous enzyme pathways for the in vivo production of the non-native monounsaturated fatty acid derivatives disclosed herein. Petrochemical or oleochemical feedstocks are not required, as the disclosed recombinant bacteria use simple carbon sources to produce native and non-native monounsaturated fatty acid derivatives having desired carbon chain lengths and having double bonds placed in specific positions.

2. Host Cells and Host Cell Cultures

In view of the present disclosure, the person having ordinary skill in the art will appreciate that any of the embodiments contemplated herein may be practiced with any host cell or microorganism that can be genetically modified via the introduction of one or more nucleic acid sequences that code for the appropriate fatty acid biosynthetic enzymes. Accordingly, the recombinant microorganisms disclosed herein function as host cells and comprise one or more polynucleotide sequences that include an open reading frame that encode one or more fatty acid biosynthetic enzymes together with operably-linked regulatory sequences that facilitate expression of the fatty acid biosynthetic polypeptide(s) in the host cell.

In some exemplary embodiments, the host cell is a Gram-positive bacterial cell. In other exemplary embodiments, the host cell is a Gram-negative bacterial cell. Exemplary microorganisms that provide suitable host cells, include but are not limited to cells from the Class gammaproteobacteria, cells from the genus *Escherichia, Bacillus, Lactobacillus, Zymomonas, Pseudomonas, Marinobacter*, or *Streptomyces*.

In some exemplary embodiments, the host cell is an *E. coli* cell. In some exemplary embodiments, the *E. coli* cell is a strain B, a strain C, a strain K, or a strain W *E. coli* cell.

a. Expression of Heterologous Enzymatic Activities in Microorganisms

The expression of enzymatic activities in microorganisms and microbial cells for the production of fatty acid derivative molecules is taught e.g., in the following U.S. Pat. Nos. 9,133,406; 9,340,801; 9,200,299; 9,068,201; 8,999,686; 8,658,404; 8,597,922; 8,535,916; 8,530,221; 8,372,610; 8,323,924; 8,313,934; 8,283,143; 8,268,599; 8,183,028; 8,110,670; 8,110,093; and 8,097,439.

Therefore, in exemplary embodiments, the host cells or host microorganisms that express heterologous dual 3-hydroxyacyl-ACP dehydratase/isomerase polypeptides for biosynthesis of non-native mUFA molecules also comprise heterologous enzyme activities that make up pathways for the biosynthetic production of fatty acid derivatives.

In some embodiments, the host cells or host microorganisms that are used to express polypeptides for biosynthesis of non-native mUFA molecules also express polypeptides having ester synthase activity (E.C. 2.3.1.75) for the production of fatty esters. In other embodiments, the host cell that expresses polypeptides for biosynthesis of non-native mUFA molecules also expresses ester synthase activity (E.C. 2.3.1.75) and acyl-CoA synthase (FadD) (E.C. 6.2.1.3) activity for the production of fatty esters.

In another embodiment, the host cell that expresses polypeptides for biosynthesis of non-native mUFA molecules also expresses polypeptides that have acyl-ACP reductase (AAR) (E.C. 1.2.1.80) activity and/or alcohol dehydrogenase activity (E.C. 1.1.1.1.) and/or fatty alcohol acyl-CoA reductase (FAR) (E.C. 1.1.1.-) activity and/or carboxylic acid reductase (CAR) (EC 1.2.99.6) activity for the production of fatty alcohols. In another exemplary embodiment, the host cell that expresses polypeptides for biosynthesis of non-native mUFA molecules also expresses polypeptides that have acyl-CoA reductase (E.C. 1.2.1.50) activity, and acyl-CoA synthase (FadD) (E.C. 6.2.1.3) activity, for the production of fatty alcohols. In another embodiment, the host cell that expresses polypeptides for biosynthesis of non-native mUFA molecules also expresses polypeptides that have acyl-ACP reductase (AAR) (E.C. 1.2.1.80) activity and alcohol dehydrogenase activity (E.C. 1.1.1.1.) for the production of fatty alcohols.

In another exemplary embodiment, the host cell that expresses polypeptides for biosynthesis of non-native mUFA molecules also expresses polypeptides that have acyl-ACP reductase (AAR) (E.C. 1.2.1.80) activity for the production of fatty aldehydes. In another embodiment, the host cell that expresses polypeptides for biosynthesis of non-native mUFA molecules also expresses polypeptides that have acyl-ACP reductase (AAR) (E.C. 1.2.1.80) activity and decarbonylase activity (aldehyde forming oxygenase) for the production of alkanes and alkenes.

In another exemplary embodiment, the host cell that expresses polypeptides for biosynthesis of non-native mUFA molecules also expresses polypeptides that have OleA activity for the production of ketones. In another exemplary embodiment, the host cell that expresses polypeptides for biosynthesis of non-native mUFA molecules also expresses polypeptides that have OleBCD activity for the production of internal olefins. In another embodiment, the host cell that expresses polypeptides for biosynthesis of non-native mUFA molecules also expresses polypeptides that have decarboxylase activity for making terminal olefins.

In some embodiments, the host cell that expresses polypeptides for biosynthesis of non-native mUFA molecules also comprise certain native enzyme activities that are upregulated or overexpressed in order to produce one or more particular fatty acid derivative(s) such as e.g., fatty esters, fatty alcohols, fatty amines, fatty aldehydes, bifunctional fatty acid derivatives, diacids, etc.

Typically, the fatty acid derivatives which comprise non-native mUFAs disclosed herein are recovered from the culture medium and/or are isolated from the host cells. In one exemplary embodiment, the non-native monounsaturated fatty acid derivatives are recovered from the culture medium (extracellular). In another exemplary embodiment, the non-native monounsaturated fatty acid derivatives are isolated from the host cells (intracellular). In another exemplary embodiment, the non-native monounsaturated fatty acid derivatives are recovered from the culture medium and isolated from the host cells.

A fatty acid derivative composition produced by a host cell can be analyzed using methods known in the art, for example, Gas-Chromatography with Flame Ionization Detection (GC-FID) in order to determine the distribution of particular non-native monounsaturated fatty acid derivatives as well as chain lengths and degree of saturation of the components of the fatty acid derivative composition. Similarly, other compounds can be analyzed through methods well known in the art.

b. Genetic Alterations for Fine Tuning Recombinant Host Cells

In some exemplary embodiments, host cells comprise optional genetic manipulations and alterations can be used to enhance or otherwise fine tune the production of non-native monounsaturated fatty acid derivative molecules. As will be appreciated by a person having ordinary skill in the art, optional genetic manipulations can be used interchangeably from one host cell to another, depending on what other heterologous enzymes and what native enzymatic pathways are present in the host cell. Some optional genetic manipulations are discussed below.

FadE

FadE (Acyl-CoA dehydrogenase) catalyzes the first step the first step in fatty acid utilization/degradation (β-oxidation cycle) which is the oxidation of acyl-CoA to 2-enoyl-CoA (see e.g., Campbell, J. W. and Cronan, J. E. Jr (2002) *J. Bacteriol.* 184(13): 3759-3764, Lennen, R. M. and Pfleger, B. F (2012) *Trends Biotechnol.* 30(12):659-667). Since fadE initiates the β-oxidation cycle, when *E. coli* lacks FadE, it cannot grow on fatty acids as a carbon source (see e.g., Campbell, J. W. and Cronan supra). The same effect can be achieved by attenuating other enzymes from the β-oxidation cycle, e.g. FadA, which is a 3-ketoacyl-CoA thiolase, or FadB, which is a dual 3-hydroxyacyl-CoA-dehydrogenase/dehydratase.

However, when *E. coli* is grown on a carbon source other than fatty acids e.g., grown on sugar, acetate, etc., fadE attenuation is optional because under such conditions fadE expression is repressed by FadR. Therefore, when cells are grown on a simple carbon source such as e.g., glucose, the fadE gene product is already attenuated. Accordingly, when grown on a carbon source other than fatty acids, a fadE mutation/deletion is optional.

fhuA

The gene fhuA codes for the TonA protein, which is an energy-coupled transporter and receptor in the outer membrane of *E. coli* (see e.g., V. Braun (2009) *J Bacteriol.* 191(11):3431-3436). The fhuA deletion allows the cell to become more resistant to phage attack. This phenotype can be beneficial in certain fermentation conditions. Its deletion is optional.

entD

For example, the entD gene codes for a phosphopantetheinyl transferase. Overexpression of native *E. coli* entD, a phosphopantetheinyl transferase, enables the activation of CarB from apo-CarB to holo-CarB, thereby allowing conversion of free fatty acids into fatty aldehydes, which can then be converted to fatty alcohols by a fatty aldehyde reductase see e.g., U.S. Pat. No. 9,340,801.

Overexpression of Non-Native and/or Native and/or Variants of Genes Involved in the Synthesis of Acyl-ACP In some embodiments, the fatty acid biosynthetic pathway in the production host uses the precursors acetyl-CoA and malonyl-CoA. *E. coli* or other host organisms engineered to overproduce these components can serve as the starting point for subsequent genetic engineering steps to provide the specific output product (such as, fatty acids, fatty esters, hydrocarbons, fatty alcohols). Several different modifications can be made, either in combination or individually, to the host strain to obtain increased acetyl-CoA/malonyl-CoA/fatty acid and fatty acid derivative production see e.g., US Patent Application Publication 2010/0199548.

Other exemplary modifications of a host cell include e.g., overexpression of non-native and/or native and/or variants of genes involved in the synthesis of acyl-ACP. In general, by increasing acyl-ACP synthesis increases the amount of acyl-ACP, which is the substrate of thioesterases, estersynthases and acyl-ACP reductases. Exemplary enzymes that increase acyl-ACP production include e.g., enzymes that make up the "fatty acid synthase" (FAS). As is known in the art (see e.g., US 2010/0199548) FAS enzymes are a group of enzymes that catalyze the initiation and elongation of acyl chains. The acyl carrier protein (ACP) along with the enzymes in the FAS pathway control the length, degree of saturation, and branching of the fatty acids produced. Enzymes that comprise FAS include e.g., AccABCD, FabD, FabH, FabG, FabA, FabZ, FabI, FabK, FabL, FabM, FabQ, FabV, FabX, FabB, and FabF. Depending upon the desired product one or more of these genes can be attenuated or over-expressed.

Therefore, in exemplary embodiments a host strain may overexpress of one or more of the FAS genes. Exemplary FAS genes that may be overexpressed include e.g., fadR from *Escherichia coli* (NP 415705.1)fabA from *Salmonella typhimurium* (NP_460041), fabD from *Salmonella typhimurium* (NP_460164), fabG from *Salmonella typhimurium* (NP_460165), fabH from *Salmonella typhimurium* (NP_460163), fabV from *Vibrio cholera* (YP_001217283), and fabF from *Clostridium acetobutylicum* (NP_350156). In some exemplary embodiments, the overexpression of one or more of these genes, which code for enzymes and regulators in fatty acid biosynthesis, serves to further increase the titer of fatty-acid derivative compounds under particular culture conditions. In some exemplary embodiments, the wild-type *E. coli* strains MG1655 or W3110 (see e.g., Blattner, et al. (1997) 277(5331): 1453-1462; Jensen, K. F. (1993) *J. Bact.,* 175(11): 3401-3407) are used as host strains.

3. Methods of Making Recombinant Host Cells and Cultures

Any method known in the art can be used to engineer host cells to produce fatty acid derivatives and/or fatty acid derivative compositions or other compounds. Methods for engineering host cells are well known in the art and are readily appreciated and accessible to the skilled practitioner. See e.g., Sambrook et al. (supra); Current Protocols in Molecular Biology (supra).

Generally, a polynucleotide (or gene) sequence is provided to the host cell by way of a recombinant vector that comprises a promoter operably linked to the fatty acid biosynthetic polynucleotide sequence of interest. Once a polynucleotide sequence(s) encoding fatty acid biosynthetic pathway polypeptide has been prepared and isolated, various methods may be used to construct expression cassettes, vectors and other DNA constructs. The skilled artisan is well aware of the genetic elements that must be present on an expression construct/vector in order to successfully transform, select and propagate the expression construct in host cells. Techniques for manipulation of nucleic acids such as subcloning nucleic acid sequences into expression vectors, labeling probes, DNA hybridization, and the like are described generally in e.g., Sambrook, et al., supra; Current Protocols in Molecular Biology, supra.

A number of recombinant vectors are available to those of skill in the art for use in the stable transformation/transfection of bacteria and other microorganisms (see e.g., Sambrook, et al., supra). Appropriate vectors are readily chosen by one of skill in the art.

Once an appropriate vector is identified and constructed, the appropriate transformation technique is readily chosen by the skilled practitioner. Exemplary transformation/transfection methods available to those skilled in the art include e.g., electroporation, calcium chloride transformation and etc., such methods being well known to the skilled artisan (see e.g., Sambrook, supra). In exemplary embodiments, polynucleotide sequences, comprising open reading frames encoding proteins and operably-linked regulatory sequences can be integrated into a chromosome of the recombinant host cells, incorporated in one or more plasmid expression system resident in the recombinant host cells, or both.

As will be appreciated by those skilled in the art, the design of the expression vector can depend on such factors as e.g., the choice of the host cell to be transformed, the level of expression of polypeptide desired, etc.

III. Culture and Fermentation of Recombinant Host Cells

As used herein, fermentation broadly refers to the conversion of organic materials into target substances by recombinant host cells. For example, this includes the conversion of a carbon source by recombinant host cells into non-native monounsaturated fatty acid derivative molecules as disclosed herein by propagating a culture of the recombinant host cells in a media comprising a carbon source. Conditions permissive for the production of target substances such as e.g., non-native monounsaturated fatty acid derivative molecules as disclosed herein, are any conditions that allow a host cell to produce a desired product, such as a non-native monounsaturated fatty acid derivative composition. Suitable conditions include, for example, typical fermentation conditions see e.g., *Principles of Fermentation Technology*, 3rd Edition (2016) supra; *Fermentation Microbiology and Biotechnology*, 2nd Edition, (2007) supra.

Fermentation conditions can include many parameters, well known in the art, including but not limited to temperature ranges, pH levels, levels of aeration, feed rates and media composition. Each of these conditions, individually and in combination, allows the host cell to grow. Fermentation can be aerobic, anaerobic, or variations thereof (such as micro-aerobic). Exemplary culture media include broths (liquid) or gels (solid). Generally, the medium includes a carbon source (e.g., a simple carbon source derived from a renewable feedstock) that can be metabolized by a host cell directly. In addition, enzymes can be used in the medium to facilitate the mobilization (e.g., the depolymerization of starch or cellulose to fermentable sugars) and subsequent metabolism of the carbon source to produce non-native monounsaturated fatty acid derivatives.

For small scale production, the host cells engineered to produce non-native monounsaturated fatty acid derivative compositions are typically grown in batches of, for example, about 100 µL, 200 µL, 300 µL, 400 µL, 500 µL, 1 mL, 5 mL, 10 mL, 15 mL, 25 mL, 50 mL, 75 mL, 100 mL, 500 mL, 1 L, 2 L, 5 L, or 10 L.

For large scale production, the engineered host cells can be grown in cultures having a volume batches of about 10 L, 100 L, 1000 L, 10,000 L, 100,000 L, 1,000,000 L or larger; fermented; and induced to express any desired polynucleotide sequence.

The non-native monounsaturated fatty acid derivative compositions disclosed herein can be found in the extracellular environment of the recombinant host cell culture and can be readily isolated from the culture medium by methods known in the art. A non-native monounsaturated fatty acid derivative may be secreted by the recombinant host cell, transported into the extracellular environment or passively transferred into the extracellular environment of the recombinant host cell culture.

Exemplary microorganisms suitable for use as production host cells for the production of non-native monounsaturated fatty acid derivatives include e.g., bacteria, cyanobacteria, etc. To produce fatty acid derivative compositions production host cells (or equivalently, host cells) are engineered to comprise fatty acid biosynthesis pathways that are modified relative to non-engineered or native host cells e.g., engineered as discussed above and as disclosed e.g., in U.S. Patent Application Publication 2015/0064782. Production hosts engineered to comprise modified fatty acid biosynthesis pathways are able to efficiently convert glucose or other renewable feedstocks into fatty acid derivatives. Protocols and procedures for high density fermentations for the production of various compounds have been established (see, e.g., U.S. Pat. Nos. 8,372,610; 8,323,924; 8,313,934; 8,283,143; 8,268,599; 8,183,028; 8,110,670; 8,110,093; and 8,097,439).

In some exemplary embodiments, a production host cell is cultured in a culture medium (e.g., fermentation medium) comprising an initial concentration of a carbon source (e.g., a simple carbon source) of about 20 g/L to about 900 g/L. In other embodiments, the culture medium comprises an initial concentration of a carbon source of about 2 g/L to about 10 g/L; of about 10 g/L to about 20 g/L; of about 20 g/L to about 30 g/L; of about 30 g/L to about 40 g/L; or of about 40 g/L to about 50 g/L. In some embodiments, the level of available carbon source in the culture medium can be monitored during the fermentation proceeding. In some embodiments, the method further includes adding a supplemental carbon source to the culture medium when the level of the initial carbon source in the medium is less than about 0.5 g/L.

In some exemplary embodiments, a supplemental carbon source is added to the culture medium when the level of the carbon source in the medium is less than about 0.4 g/L, less than about 0.3 g/L, less than about 0.2 g/L, or less than about 0.1 g/L. In some embodiments, the supplemental carbon source is added to maintain a carbon source level of about 1 g/L to about 25 g/L. In some embodiments, the supplemental carbon source is added to maintain a carbon source level of about 2 g/L or more (e.g., about 2 g/L or more, about 3 g/L or more, about 4 g/L or more). In certain embodiments, the supplemental carbon source is added to maintain a carbon source level of about 5 g/L or less (e.g., about 5 g/L or less, about 4 g/L or less, about 3 g/L or less). In some embodiments, the supplemental carbon source is added to maintain a carbon source level of about 2 g/L to about 5 g/L, of about 5 g/L to about 10 g/L, or of about 10 g/L to about 25 g/L.

In one exemplary embodiment the carbon source for the fermentation is derived from a renewable feedstock. In some embodiments, the carbon source is glucose. In other embodiments, the carbon source is glycerol. Other possible carbon sources include, but are not limited to, fructose, mannose, galactose, xylose, arabinose, starch, cellulose, pectin, xylan, sucrose, maltose, cellobiose, and turanose; cellulosic material and variants such as hemicelluloses, methyl cellulose and sodium carboxymethyl cellulose; saturated or unsaturated fatty acids, succinate, lactate, and acetate; alcohols, such as ethanol, methanol, and glycerol, or mixtures thereof. In one embodiment, the carbon source is derived from corn, sugar cane, sorghum, beet, switch grass, ensilage, straw, lumber, pulp, sewage, garbage, cellulosic urban waste, flu-gas, syn-gas, or carbon dioxide. The simple carbon source can also be a product of photosynthesis, such as glucose or sucrose. In one embodiment, the carbon source is derived from a waste product such as glycerol, flu-gas, or syn-gas; or from the reformation of organic materials such as biomass; or from natural gas or from methane, or from the reformation of these materials to syn-gas; or from carbon dioxide that is fixed photosynthetically, for example non-native monounsaturated fatty acid derivatives may be produced by recombinant cyanobacteria growing photosynthetically and using $CO_2$ as carbon source. In some exemplary embodiments, the carbon source is derived from biomass. An exemplary source of biomass is plant matter or vegetation, such as corn, sugar cane, or switchgrass. Another exemplary source of biomass is metabolic waste products, such as animal matter (e.g., cow manure). Further exemplary sources of biomass include algae and other marine plants. Biomass also includes waste products from industry, agriculture, forestry, and households, including, but not limited to, fermentation waste, ensilage, straw, lumber, sewage, garbage, cellulosic urban waste, municipal solid waste, and food leftovers.

In some exemplary embodiments, a non-native monounsaturated fatty acid derivative is produced at a concentration of about 0.5 g/L to about 40 g/L. In some embodiments, a fatty acid derivative is produced at a concentration of about 1 g/L or more (e.g., about 1 g/L or more, about 10 g/L or more, about 20 g/L or more, about 50 g/L or more, about 100 g/L or more). In some embodiments, a fatty acid derivative is produced at a concentration of about 1 g/L to about 170 g/L, of about 1 g/L to about 10 g/L, of about 40 g/L to about 170 g/L, of about 100 g/L to about 170 g/L, of about 10 g/L to about 100 g/L, of about 1 g/L to about 40 g/L, of about 40 g/L to about 100 g/L, or of about 1 g/L to about 100 g/L.

In other exemplary embodiments, a non-native monounsaturated fatty acid derivative is produced at a titer of about 25 mg/L, about 50 mg/L, about 75 mg/L, about 100 mg/L, about 125 mg/L, about 150 mg/L, about 175 mg/L, about 200 mg/L, about 225 mg/L, about 250 mg/L, about 275 mg/L, about 300 mg/L, about 325 mg/L, about 350 mg/L, about 375 mg/L, about 400 mg/L, about 425 mg/L, about 450 mg/L, about 475 mg/L, about 500 mg/L, about 525 mg/L, about 550 mg/L, about 575 mg/L, about 600 mg/L, about 625 mg/L, about 650 mg/L, about 675 mg/L, about 700 mg/L, about 725 mg/L, about 750 mg/L, about 775 mg/L, about 800 mg/L, about 825 mg/L, about 850 mg/L, about 875 mg/L, about 900 mg/L, about 925 mg/L, about 950 mg/L, about 975 mg/L, about 1000 mg/L, about 1050 mg/L, about 1075 mg/L, about 1100 mg/L, about 1125 mg/L, about 1150 mg/L, about 1175 mg/L, about 1200 mg/L, about 1225 mg/L, about 1250 mg/L, about 1275 mg/L, about 1300 mg/L, about 1325 mg/L, about 1350 mg/L, about 1375 mg/L, about 1400 mg/L, about 1425 mg/L, about 1450 mg/L, about 1475 mg/L, about 1500 mg/L, about 1525 mg/L, about 1550 mg/L, about 1575 mg/L, about 1600 mg/L, about 1625 mg/L, about 1650 mg/L, about 1675 mg/L, about 1700 mg/L, about 1725 mg/L, about 1750 mg/L, about 1775 mg/L, about 1800 mg/L, about 1825 mg/L, about 1850 mg/L, about 1875 mg/L, about 1900 mg/L, about 1925 mg/L, about 1950 mg/L, about 1975 mg/L, about 2000 mg/L (2 g/L), 3 g/L, 5 g/L, 10 g/L, 20 g/L, 30 g/L, 40 g/L, 50 g/L, 60 g/L, 70 g/L, 80 g/L, 90 g/L, 100 g/L or a range bounded by any two of the foregoing values. In other embodiments, a fatty acid derivative or other compound is produced at a titer of more than 100 g/L, more than 200 g/L, or more than 300 g/L. In exemplary embodiments, the titer of fatty acid derivative or other compound produced by a recombinant host cell according to the methods disclosed herein is from 5 g/L to 200 g/L, 10 g/L to 150 g/L, 20 g/L to 120 g/L and 30 g/L to 100 g/L. The titer may refer to a particular fatty acid derivative or a combination of fatty acid derivatives or another compound or a combination of other compounds produced by a given recombinant host cell culture. In exemplary embodiments, the expression of ChFatB2 thio-esterase variant in a recombinant host cell such as *E. coli* results in the production of a higher titer as compared to a recombinant host cell expressing the corresponding wild type polypeptide. In one embodiment, the higher titer ranges from at least about 5 g/L to about 200 g/L.

In other exemplary embodiments, the host cells engineered to produce a non-native monounsaturated fatty acid derivative according to the methods of the disclosure have a yield of at least 1%, at least 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 26%, at least about 27%, at least about 28%, at least about 29%, or at least about 30% or a range bounded by any two of the foregoing values. In other embodiments, a fatty acid derivative or derivatives or other compound(s) are produced at a yield of more than about 30%, more than about 35%, more than about 40%, more than about 45%, more than about 50%, more than about 55%, more than about 60%, more than about 65%, more than about 70%, more than about 75%, more than about 80%, more than about 85%, more than about 90%, more than 100%, more than 200%, more than 250%, more than 300%, more than 350%, more than 400%, more than 450%, more than 500%, more than 550%, more than 600%, more than 650%, more than 700%, more than 750%, or more. Alternatively, or in addition, the yield is about 30% or less, about 27% or less, about 25% or less, or about 22% or less. In another embodiment, the yield is about 50% or less, about 45% or less, or about 35% or less. In another embodiment, the yield is about 95% or less, or 90% or less, or 85% or less, or 80% or less, or 75% or less, or 70% or less, or 65% or less, or 60% or less, or 55% or less, or 50% or less. Thus, the yield can be bounded by any two of the above endpoints. For example, the yield of a non-native monounsaturated fatty acid derivative e.g., a 6, 7, 8, 9, 10, 11, 12, 13, 14, 15, 16, 18, etc. carbon non-native monounsaturated fatty acid derivative produced by the recombinant host cell according to the methods disclosed herein can be about 5% to about 15%, about 10% to about 25%, about 10% to about 22%, about 15% to about 27%, about 18% to about 22%, about 20% to about 28%, about 20% to about 30%, about 30% to about 40%, about 40% to about 50%, about 50% to about 60%, about 60% to about 70%, about 70% to about 80%, about 80% to about 90%, about 90% to about 100%, about 100% to about 200%, about 200% to about 300%, about 300% to about 400%, about 400% to about 500%, about 500% to about 600%, about 600% to about 700%, or about 700% to about 800%. The yield may refer to a particular non-native monounsaturated fatty acid derivative or a combination of fatty acid derivatives. In one embodiment, the higher yield ranges from about 10% to about 800% of theoretical yield. In addition, the yield will also be dependent on the feedstock used.

In some exemplary embodiments, the productivity of the host cells engineered to produce a non-native monounsaturated fatty acid derivative according to the methods of the disclosure is at least 100 mg/L/hour, at least 200 mg/L/hour, at least 300 mg/L/hour, at least 400 mg/L/hour, at least 500 mg/L/hour, at least 600 mg/L/hour, at least 700 mg/L/hour, at least 800 mg/L/hour, at least 900 mg/L/hour, at least 1000 mg/L/hour, at least 1100 mg/L/hour, at least 1200 mg/L/hour, at least 1300 mg/L/hour, at least 1400 mg/L/hour, at least 1500 mg/L/hour, at least 1600 mg/L/hour, at least 1700 mg/L/hour, at least 1800 mg/L/hour, at least 1900 mg/L/hour, at least 2000 mg/L/hour, at least 2100 mg/L/hour, at least 2200 mg/L/hour, at least 2300 mg/L/hour, at least 2400 mg/L/hour, 2500 mg/L/hour, or as high as 10 g/L/hour (dependent upon cell mass). For example, the productivity of a malonyl-CoA derived compound including a fatty acid derivative or derivatives or other compound(s) produced by a recombinant host cell according to the methods of the disclosure may be from 500 mg/L/hour to 2500 mg/L/hour, or from 700 mg/L/hour to 2000 mg/L/hour. The productivity may refer to a particular 8 and/or 10 carbon fatty acid derivative or a combination of fatty acid derivatives or other compound(s) produced by a given host cell culture. For example, the expression of a ChFatB2 thioesterase variant in a recombinant host cell such as E. coli results in increased productivity of an 8 and/or 10 carbon fatty acid derivatives or other compounds as compared to a recombinant host cell expressing the corresponding wild type polypeptide. In exemplary embodiments, higher productivity ranges from about 0.3 g/L/h to about 3 g/L/h to about 10 g/L/h to about 100 g/L/h to about a 1000 g/L/h.

As disclosed supra, in some exemplary embodiments, the host cell used in the fermentation procedures discussed herein (supra) is a mammalian cell, plant cell, insect cell, yeast cell, fungus cell, filamentous fungi cell, an algal cell, a cyanobacterial cell, and bacterial cell.

IV. Isolation

Bioproducts e.g., compositions comprising non-native monounsaturated fatty acid derivatives as disclosed herein which are produced utilizing recombinant host cells as discussed above are typically isolated from the fermentation broth by methods known in the art. In an exemplary embodiment the compositions comprising non-native monounsaturated fatty acid derivatives as disclosed herein which are produced utilizing recombinant host cells are discussed above are isolated from the fermentation broth by gravity settling, centrifugation, or decantation.

V. Compositions and Formulations of Non-Native Monounsaturated Fatty Acid Derivative Molecules Bioproducts e.g., compositions comprising non-native monounsaturated fatty acid derivative molecules produced utilizing engineered bacteria as discussed herein, are produced from renewable sources (e.g., from a simple carbon source derived from renewable feedstocks) and, as such, are new compositions of matter. These new bioproducts can be distinguished from organic compounds derived from petrochemical carbon on the basis of dual carbon-isotopic fingerprinting or $^{14}C$ dating. Additionally, the specific source of biosourced carbon (e.g., glucose vs. glycerol) can be determined by dual carbon-isotopic fingerprinting by methods known in the art (see, e.g., U.S. Pat. No. 7,169,588, WO 2016/011430 A1, etc.).

The following examples are offered to illustrate, but not to limit the invention.

EXAMPLES

Example 1

The following Example illustrates materials and methods for Examples 2-9 disclosed herein below.

Methods

Small Scale Fermentation Protocol:

40 µL LB culture (from an LB culture growing in a 96 well plate) was used to inoculate 360 µL LB media, which was then incubated for approximately 4 hours at 32° C. shaking. 80 µL of the LB seed was used to inoculate 320 µL Nlim media (Table 6). After growing at 32° C. for 2 hours, the cultures were induced with IPTG (final concentration 1 mM). The cultures were then incubated at 32° C. with shaking for 20 hours if not noted otherwise, after which they were extracted following the standard extraction protocol detailed below.

TABLE X

| N-lim Media Formulation | |
| --- | --- |
| 1 × | 5 × Salt Soln. with NH4Cl |
| 1 × | 1000 × Trace Vitamins |
| 1 mg/L | 10 mg/mL Thiamine |
| 1 mM | 1M MgSO4 |
| 0.1 mM | 1M CaCl2 |
| 40 g/L | 500 g/L glucose |
| 1 × | 1000 × Trace minerals |
| 10 mg/L | 10 g/L Fe Citrate |
| 100 µg/mL | 100 mg/ml spectinomycin |
| 100 mM | 2M BisTris (pH7.0) |
| 0.5 mM | Aminolevulinic acid |

Fatty Acid Species Standard Extraction and Analytical Protocol

To each well to be extracted, 80 µL of 1M HCl, followed by 400 µL of butyl acetate containing 500 mg/L 1-undecanol or 500 mg/L undecanoic acid as internal standard (IS) was added as internal standard (IS) was added. The 96 well plates were then heat-sealed using a plate sealer (ALPS-300 heater; Abgene, ThermoScientific, Rockford, IL), and shaken for 15 minutes at 2000 rpm using MIXMATE mixer (Eppendorf, Hamburg, Germany). After shaking, the plates were centrifuged for 10 minutes at 4500 rpm at room temperature (Allegra X-15R, rotor SX4750A, Beckman Coulter, Brea, CA) to separate the aqueous and organic layers. 50 µL of the organic layer was transferred to a 96 well plate (polypropylene, Corning, Amsterdam, The Netherlands) and derivatized with 50 µL of trimethylsiloxy/N,O-Bis(trimethylsilyl)

trifluoroacetamide (TMS/BSTFA). The plate was subsequently heat sealed and stored at −20° C. until evaluated by either Gas Chromatography with Flame Ionization Detection (GC-FID) or Gas Chromatography-Mass Spectrometry (GC-MS).

The GC-MS parameters used to generate chromatograms and mass spectra for compounds identification were as follows: 1 µl sample was injected into analytical Column: DB-1HT, 15 m×250 µm×0.1 µm, available from Agilent with cat #J&W 122-1111E, Oven temperature: initial at 50° C., hold for 5 minutes, increase to 300° C. at 25° C./min, and hold for 5.24 minutes for a total run time of 24 minutes. Column flow: 1.2 mL/min, Inlet temperature: 300° C., Split ratio: 20:1, Software: ChemStation E.02.01.1177. MS parameters: Transfer line temperature: 300° C., MS source: 230° C., MS Quad: 150° C. Auto sampler: Combi PAL (CTC analytics) distributed by LEAP Technologies. The GC-FID parameters used to quantify each compound were carried out as follows: 1 µL of sample was injected onto an analytical column (UFC Rtx-1, 5 M×0.1 mm×0.1 µM) in a Thermo Fisher UltraFast TRACE GC (Thermo Fisher Scientific, West Palm Beach, FL). Oven temperature: initial at 100° C., hold for 0.2 minutes, increase to 320° C. at 100° C./min, and hold for 0.5 minutes for a total run time of 2.5 minutes using column flow of 0.5 ml/min, Inlet temperature: 300° C. and flame ionization detector temperature: 300° C.

The protocol detailed above represents standard conditions, which may be modified as necessary to optimize the analytical results.

Cellular Fatty Acid Analysis:

Strains were grown over night in Luria-Bertani (LB) medium. The cellular fatty acids (i.e. fatty acids mainly from membrane phospholipids) were extracted and analyzed as following: 10-20 mL of cultures were harvested and saponified at 70° C. for 1 hr using 1 mL of 15% (W/V) NaOH in 50% MeOH. The solutions were cooled down to room temperature and acidified by concentrated HCl to pH of 1-2. The acidic solution was then extracted with butyl acetate using a vortexer (DVX-2500 multi-tube vortexer, VWR) at 2500 rpm for 5 minutes. Extracts were centrifuged in an Eppendorf centrifuge (centrifuge 5424) at 15000 rpm for 5 minutes at room temperature. The organic layer (100 µL) was pipetted to a GC vial with insert, derivatized by adding 100 µL of N,O-bis(trimethylsilyl) trifluoroacetamide (BSTFA) and 1% trimethylchlorosilane (TMCS) and mixed using a vortexer for 30 seconds. The sample was then injected on GC-MS to generate chromatograms and mass spectra for compound identification. The GC-MS parameters were the same as above.

Example 2

The following Example illustrates a recombinant E. coli strain having non-native ω9-monounsaturated fatty acids in its cellular fatty acids.

As will be shown below, a recombinant E. coli strain with its fabA gene replaced with a heterologous fabA gene from Marinobacter aquaeolei is viable and contains in its cellular fatty acids (i.e. within its membrane phospholipids) non-native monounsaturated fatty acids.

The chromosomal copy of the E. coli fabA gene was replaced with the fabA gene from a Marinobacter strain in the following way. The fabA gene was amplified from Marinobacter aquaeolei VT8 (or synonymously Marinobacter hydrocarbonoclasticus VT8 Accession WP 011786589) genomic DNA (accession number ABM20221). Sewing PCR (see e.g., Bryksin, A. V., and Matsumura I., Biotechniques. 2010 June; 48(6): 463-465) was used to construct a fabA replacement cassette consisting of ~500 bp fabA_Ecol upstream DNA region, the full fabA_Maqu gene, a Kanamycin cassette and ~500 bp of fabA_Ecol downstream DNA region.

The sewing PCR product was electroporated into E. coli PAM155 (see e.g., Johnson and Greenberg (1975) J. Bacteriol. 122(2):570-574) and integrated into the E. coli chromosome using the widely used lambda-red helper system (see e.g., Datsenko and Wanner (2000) PNAS 97(12):6640-6645). The exact replacement of the E. coli fabA gene with the Marinobacter fabA gene was verified by PCR and sequencing. The resulting strain, E. coli PAM155 ΔfabA_Ecol::fabA_Maqu-Kan, was named AA.029. The strain grew slower than its parent strain, both in Luria-Bertani as well as in Mineral-glucose media, but it was viable and it did not require any growth supplements such as oleic acid or the FabI inhibitor triclosan. These results demonstrate that Marinobacter FabA can functionally replace the E. coli FabA.

Figure 8:
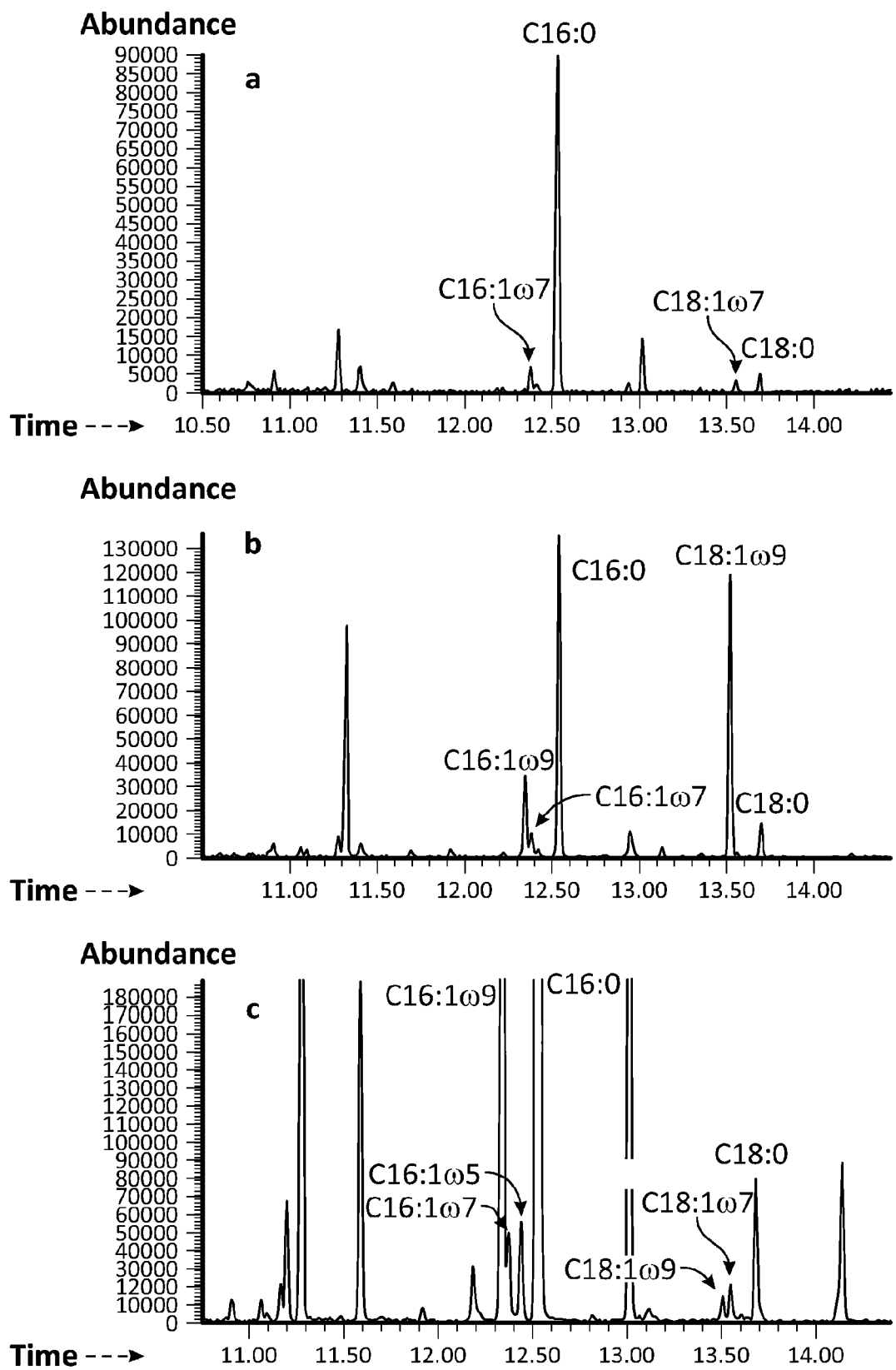
FIG. 8 Illustrates GC/MS chromatographs of cellular fatty acids from *E. coli* PAM155 (A), *Marinobacter hydrocarbonoclasticus* (B) and *E. coli* AA.209 (C).
Figure 9:
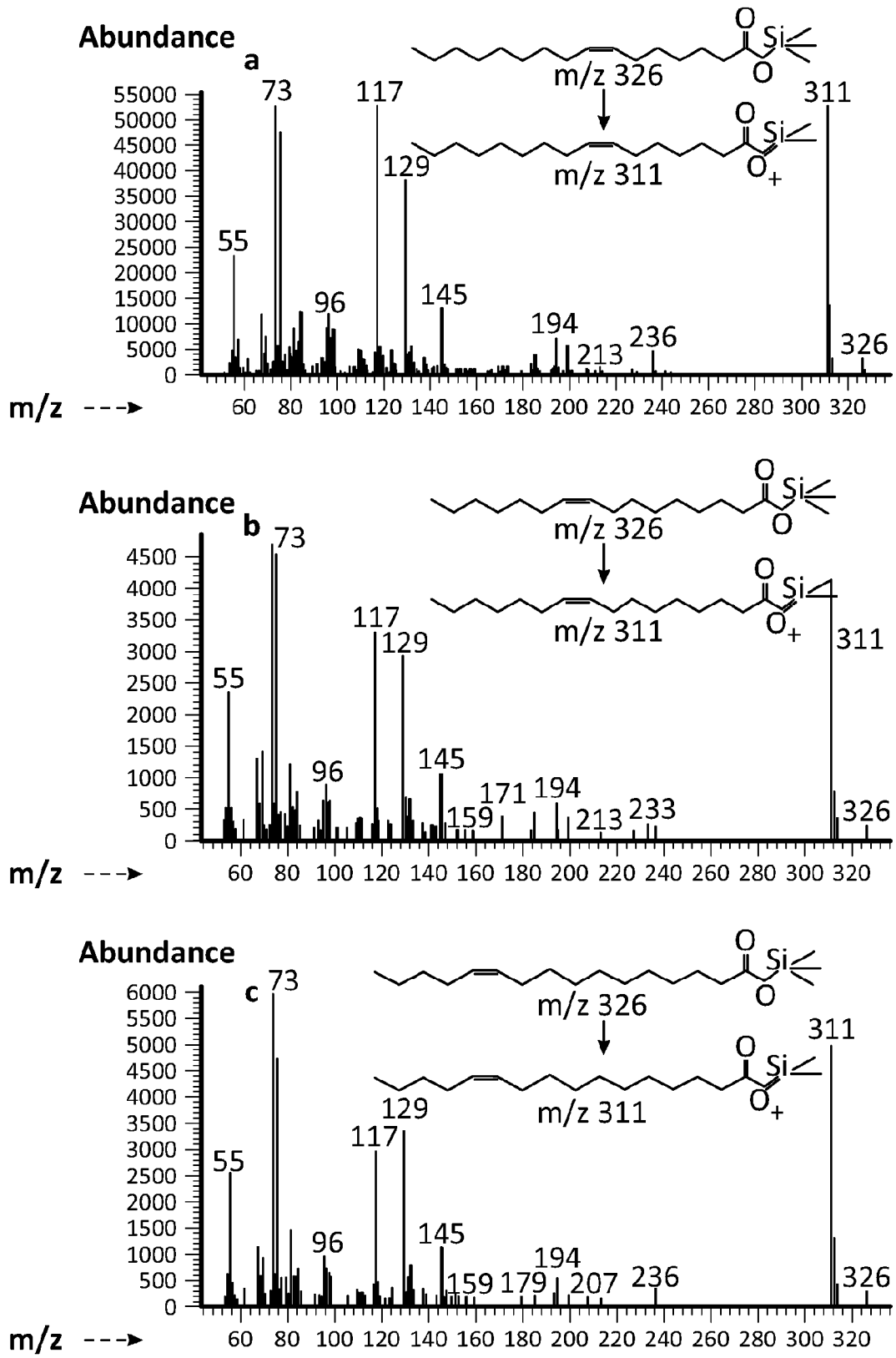
FIG. 9 Illustrates the mass spectrum and ion fragmentation pattern of the peaks corresponding to (ω9)Δ7-hexadecenoic acid (A), (ω7)Δ9-hexadecenoic acid (B) (ω5)Δ11-hexadecenoic acid (C) in cellular fatty acids of *E. coli* AA.209 from FIG. 8C.

The cellular fatty acids of strain AA.029 (E. coli ΔfabA_Ecol::fabA_Maqu-Kan) and control strains E. coli MG1655 and Marinobacter hydrocarbonoclasticus DSMZ8798 were analyzed as described in Example 1. The GC chromatograph of trimethylsilyl derivatives of the cellular fatty acids for all three strains is shown in FIG. 8. The peak identification was performed using authentic standards, for example ω9-hexadecenoic acid (also known as (z7)-hexadecenoic acid), ω7-hexadecenoic acid (also known as (z9)-hexadecenoic acid) and ω5-hexadecenoic acid (also known as (z11)-hexadecenoic acid) (see FIG. 8 for their retention time and FIG. 9 for their ion fragmentation pattern), and the position of the double bond was confirmed either by using authentic standards or by GC/MS of their dimethyl disulphide (DMDS) adducts (see e.g., Nichols et al. 1986, J. Microbiol. Methods 5: 49-55).

As expected, the cellular fatty acids of wildtype E. coli (see FIG. 8A) contained only ω7-mUFAs (ω7-hexadecenoic acid and ω7-octadecenoic acid) and the cellular fatty acids of M. hydrocarbonoclasticus (see FIG. 8B) contained mainly ω9-mUFAs (ω9-hexadecenoic acid and ω9-octadecenoic acid). The cellular fatty acid profile of E. coli strain AA.029 (ΔfabA_Ecol::fabA_Maqu-Kan) (see FIG. 8C) was different from the wildtype E. coli strain. It contained ω9-hexadecenoic acid as its major mUFA as well as smaller amounts of ω7-hexadecenoic acid, ω5-hexadecenoic acid, ω7-octadecenoic acid and ω9-octadecenoic acid. ω9-hexadecenoic acid, ω5-hexadecenoic acid and ω9-octadecenoic acid are non-native fatty acids for E. coli. The composition of trimethylsilyl derivatives of cellular fatty acids is given in Table 5.

Thus, a recombinant E. coli expressing Marinobacter FabA in place of its native FabA 3-hydroxy-acyl-ACP dehydratase/isomerase synthesized mainly non-native ω9-mUFAs instead of its native ω7-mUFAs.

TABLE 5

Composition of trimethylsilyl derivatives of CFAs obtained for E. coli MG1655,
M. hydrocarbonoclasticus, and E. coli AA.029 (ΔfabA_Ecol::fabA_Maqu-Kan)

| | % of Total Trimethylsilyl Derivatives of Cellular Fatty Acids | | | | | | | | | | | |
|---|---|---|---|---|---|---|---|---|---|---|---|---|
| Strain | C12:0 | C14:1 | C14:0 | C16:1ω9 | C16:1ω7 | C16:1ω5 | C16:0 | C17:cyc | C18:1ω9 | C18:1ω7 | C18:0 | C19:cyc |
| E. coli MG1665 | ND | ND | 11.6 | ND | 3.8 | ND | 69.6 | 10 | ND | 2.2 | 2.8 | ND |
| M. hydrocarbonoclasticus | 7 | ND | 23.2 | 6.4 | 1.4 | ND | 30.4 | 1.3 | 26.3 | ND | 3.7 | ND |
| E.coli AA.029 | 4 | 0.2 | 7.7 | 12.9 | 0.4 | 1 | 58.1 | 11.4 | 0.4 | 0.4 | 1.7 | 1.8 |

ND = not detected,
cyc = cyclopropyl fatty acids

Example 3

The following Example illustrates production of secreted ω9-monounsaturated C16 and C18 fatty acids by a recombinant E. coli strain expressing heterologous FabA and FabB from Marinobacter aquaeolei.

This example shows that recombinant E. coli strains ω-expressing a heterologous thioesterase and a heterologous fabA gene from M. aquaeolei/hydrocarbonoclasticus (Example 2) produce non-native secreted ω9-monounsaturated fatty acids with and without the heterologous fabB from M. aquaeolei.

The fabA gene from M. aquaeolei (Example 2) was amplified with or without the adjacent fabB gene from genomic DNA of M. aquaeolei (WP_011786590) and was cloned into a pACYC-derivative vector (p15a replicon, kanamycin resistance marker), such that the transcription of the gene(s) was controlled by the IPTG-inducible Ptrc promoter. The plasmids were named pAA.001 (fabA_Maqu) and pAA.008 (fabAB_Maqu) (see Table 6).

An additional plasmid was created as follows: The gene encoding a plant thioesterase (fatA3) from Arabidopsis thaliana (UniProtKB—Q42561) was synthesized and cloned into a pCL1920-derivative vector (SC101 replicon, spectinomycin resistance marker), such that its transcription was controlled by the IPTG-inducible Ptrc promoter and such that it formed an operon with genes coding for acetyl-CoA carboxylase (accDACB) (WP_011013833, WP_011013826) from Corynebacterium glutamicum, biotin ligase (birA) (BAB98102) from Corynebacterium glutamicum and an acyl-carrier protein from E. coli. The plasmid was named pAS.033 (see Table 6).

Plasmid pAS.033 was cotransformed with plasmids pAA.001, pAA.008 and OP-115 (empty control plasmid) into strain E. coli PAM155 (Example 2) resulting in strains AA.007, AA.013 and AA.006, respectively. The strains were analyzed for their ability to produce (ω9-monounsaturated free fatty acids (mUFA) from glucose as described in Example 1. ω9-mUFA were identified as described in Example 2.

TABLE 6

Expression Plasmids used for the production
of non-native mUFAs in E. coli

| Plasmid | Description |
|---|---|
| OP-115 | pACYC (w/o insert) |
| pAA.001 | pACYC-fabA Maqu |
| pAA.008 | pACYC-fabAB Maqu |
| pAS.033 | pCL-Ptrc-fatA3_Atal_accCDAB-birA_Cglu-ACP |
| pLKW.072 | pCL-Ptrc-fatA3_Atal_fabB |

TABLE 6-continued

Expression Plasmids used for the production
of non-native mUFAs in E. coli

| Plasmid | Description |
|---|---|
| pXC.008 | pCL-Ptrc-A3DJY9_CLOTH |
| pKM.022 | pCL-Ptrc-fatA3_Atal_fabB |
| pKM.010 | pCL-Ptrc-fatA3_Atal_fabB-PT5-cyp153A-RhF |

TABLE 7

E. coli strains used for the production of non-native mUFAs in E. coli

| Strain | Base strain, relevant genotype | plasmid |
|---|---|---|
| MG1655 | E. coli wildtype | none |
| PAM155 | E. coli fabA (ts) | none |
| sLKW.186 | MG1655 derived base strain, fabA (wt), fabZ (wt) | none |
| sZR.409 | MG1655 derived base strain, fabA (wt), fabZ (wt) | none |
| AA.029 | PAM155 ΔfabA::fabA_Maqu | none |
| sRF.048 | sLKW.186 ΔfabA::fabA_Maqu, ΔfabZ::fabZ_Maqu | none |
| sKM.472 | sZR.409 ΔfabA::fabA_Maqu, ΔfabZ::fabZ_Maqu | none |
| sKM.545 | sZR.409 ΔfabA::fabA_Mnan, ΔfabZ::fabZ_Maqu | none |
| sKM.547 | sZR.409 ΔfabA::fabA_Mseg, ΔfabZ::fabZ_Maqu | none |
| sAL.180 | sZR.409 ΔfabA::fabA_Msim, ΔfabZ::fabZ_Msim | none |
| AA.006 | PAM155 | OP-115 |
| AA.007 | PAM155 | pAA.001 |
| AA.013 | PAM155 | pAA.008 |
| sRF.056 | sRF.048 | pLKW.072 |
| sRF.057 | sRF.048 | pXC.008 |
| sLKW.196 | sLKW.186 | pLKW.072 |
| sRF.025 | sLKW.186 | pXC.008 |
| sKM.478 | sKM.472 | pKM.022 |
| sKM.557 | sKM.545 | pKM.022 |
| sKM.559 | sKM.547 | pKM.022 |
| sAL.219 | sAL.180 | pKM.022 |
| sRF.068 | sRF.048 | pKM.010 |

As shown in Table 8 (below), control strain AA.006 produced only ω7-mUFAs (429 mg/L). Strains AA.007 as well as AA.013 produced significant amounts of ω9-mUFAs constituting 36% of the mUFAs of the respective strains.

Figure 10:
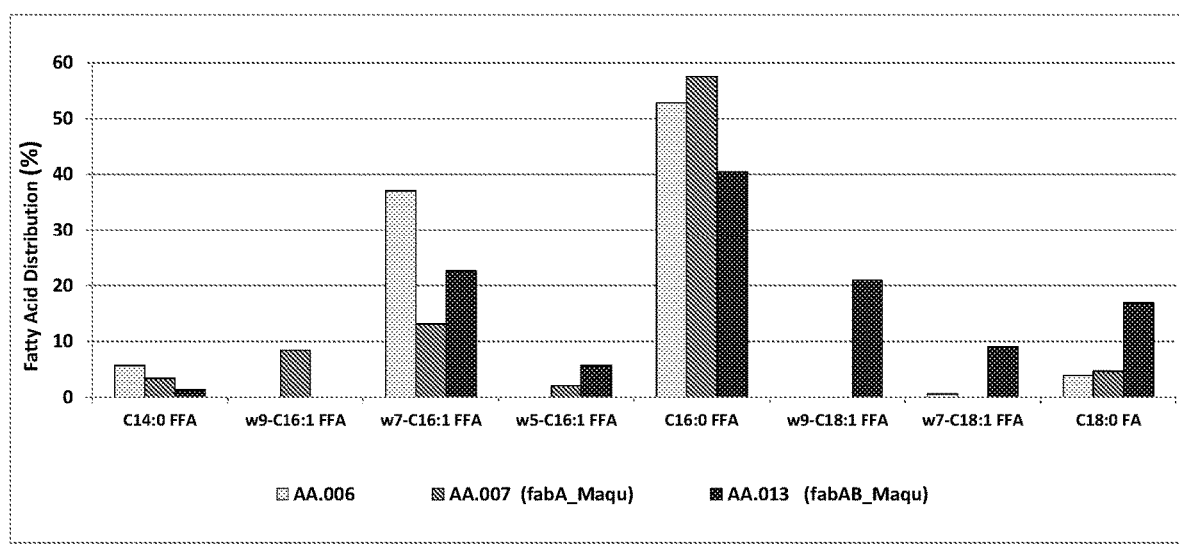
FIG. 10 Illustrates the distribution of free fatty acids produced by three recombinant *E. coli* strains.

As shown in FIG. 10, ω9-mUFAs in strain AA.007 (fabA_Maqu) were mainly ω9-hexadecenoic acid and in strain AA.013 (fabAB_Maqu) were mainly ω9-octadecenoic acid. In contrast to the control strain, both recombinant strains also produced small amounts of ω5-hexadecenoic acid.

Accordingly, this Example shows that E. coli strains overexpressing heterologous FabA from M. aquaeolei with or without heterologous FabB from *M. aquaeolei* produce significant amounts of non-native mUFAs, e.g. ω5(z11)-hexadecenoic acid, ω9(z7)-hexadecenoic acid and ω9(z9)-octadecenoic acid.

TABLE 8

Production of ω9-mUFAs in recombinant E. coli strains expressing FabA_Maqu and FabAB_Maqu

|  | Total FFA (mg/L) | Total mUFA (mg/L) | Total ω9-mUFA (mg/L) | ω9-mUFA of mUFA (%) |
|---|---|---|---|---|
| AA.006 | 1138 | 429 | 0 | 0 |
| AA.007 (fabA_Maqu) | 1015 | 268 | 96 | 36 |
| AA.013 (fabAB_Maqu) | 1393 | 663 | 238 | 36 |

Example 4

The following Example illustrates that recombinant *E. coli* strains expressing heterologous FabA and FabZ from *Marinobacter aquaeolei* replacing native *E. coli* FabA and FabZ produce ω9-monounsaturated fatty acids.

This example further shows that recombinant *E. coli* strains that ω-express heterologous fabA and fabZ genes from *Marinobacter aquaeolei* and a heterologous thioesterase produce free unsaturated free fatty acids that are almost exclusively non-native ω9-monounsaturated fatty acids.

The genome of the base strain for this experiment, sLKW.186 (Table 7) was engineered as follows: the genes coding for native chromosomal acyl-CoA dehydrogenase (FadE), β-ketoacyl-ACP synthase II (FabF), and transcriptional regulator FabR were attenuated (see e.g., U.S. Patent Application Publication 2010/0274033). A transcriptional regulator fadR was also overexpressed. Then successively both of the fabZ and fabA genes in sLKW.186 were replaced with the fabZ and fabA genes from *Marinobacter aquaeolei* (Example 2) yielding strain sRF.048.

Plasmid pLKW.072 (Table 6), a pCL1920-derivative vector (SC101 replicon, spectinomycin resistance marker), contained a thioesterase, fatA, from *Arabidopsis thaliana* (UniProtKB—Q42561) and a β-ketoacyl-ACP synthase, fabB from *E. coli* such that they formed an operon controlled by the IPTG-inducible Ptrc promoter.

Plasmid pXC.008 (Table 6), a pCL1920-derivative vector (SC101 replicon, spectinomycin resistance marker), contained thioesterase from *Clostridium thermocellum*, (A3DJY9_CLOTH), controlled by the IPTG-inducible Ptrc promoter.

Plasmids pLKW.072 and pXC.008 were transformed into sRF.048 resulting in strains sRF.056 and sRF.057, respectively (table 7). Plasmids pLKW.072 and pXC.008 were also transformed into sLKW.186 resulting in control strains sLKW.196 and sRF.025, respectively (table 7). All strains were subjected to small scale fermentation and product analysis as described in the methods (see above).

As expected the control strains sLKW.195 and sRF.025 did not produce detectable amounts of ω9-mUFA. In contrast, the mUFA produced by sRF.056 and sRF.057 consisted of almost exclusively ω9-mUFA including ω9-(z5) tetradecenoic acid, ω9-(z7) hexadecenoic acid and ω9-(z9) octadecenoic acid. Table 9 shows the total amounts of fatty acids and composition of ω9-mUFA produced by strains sRF.056 and sRF.057

Thus, this example shows that *E. coli* strains wherein the native FabA and fabZ genes are replaced by the fabA and fabZ genes from *M. aquaeolei* are (1) viable and (2) when a thioesterase is expressed, the *E. coli* strains carrying fabA and fabZ genes from *M. aquaeolei* produce significant amounts of mUFAs consisting of almost exclusively non-native ω9-mUFA, e.g. ω9-(z5)-tetradecenoic acid, ω9(z7)-hexadecenoic acid and ω9(z9)-octadecenoic acid.

TABLE 9

Production of ω9-mUFAs in recombinant E. coli strains with FabA::fabA_Maqu and fabZ::fabZ_Maqu

|  | FFA (mg/L) | mUFA (mg/L) | total (D9-mUFA (mg/L) | ω9-C14:1 mUFA (mg/L) | ω9-C16:1 mUFA (mg/L) | ω9-C18:1 mUFA (mg/L) | ω9-mUFA of mUFA (%) |
|---|---|---|---|---|---|---|---|
| sLKW.195 (control) | 4462 | 3293 | 0 | 0 | 0 | 0 | 0 |
| sRF.056 | 2481 | 1531 | 1520 | 30 | 1437 | 55 | 99 |
| sRF.025 (control) | 2372 | 1684 | 0 | 0 | 0 | 0 | 0 |
| sRF.057 | 1496 | 970 | 957 | 438 | 509 | 10 | 98 |

Example 5

The following Example illustrates production of ω9-monounsaturated fatty acids by recombinant *E. coli* strains expressing heterologous FabA and fabZ from various *Marinobacter* spp. replacing native FabA and FabZ.

This example shows that a recombinant *E. coli* strains with their fabA gene replaced by different heterologous fabA genes from the genus *Marinobacter* are viable and when expressing a heterologous thioesterase produce non-native ω9-monounsaturated fatty acids.

The genome of the base strain for this experiment, sZR.409 (Table 7), was engineered as follows: the genes coding for an acyl-CoA dehydrogenase, FadE (AAC73325 EC Number 1.3.99.3, 1.3.99.-) the β-ketoacyl-ACP synthase II (FabF, E.C. 2.3.1.179) and the transcriptional regulator FabR (NP_415705, see e.g., Cronan et al., *Mol. Microbiol.*, 29(4): 937-943 (1998)) were attenuated and a transcriptional regulator fadR was overexpressed.

The fabZ gene and then the fabA gene of sZR.409 (Table 7) were replaced with the fabZ gene *Marinobacter aquaeolei* (WP_011785996) and then the fabA gene from *Marinobacter aquaeolei* (Example 2) (Table 11) to give strain sKM.472 (Table 7). The fabZ gene and then the fabA gene of sZR.409 were replaced with the fabZ gene from *Marinobacter aquaeolei* and then the fabA gene from *Marinobacter nanhaiticus* (Table 11) to give strain sKM.545. The fabZ gene and then the fabA gene of sZR.409 were replaced with the fabZ gene from *Marinobacter aquaeolei* and the fabA gene from *Marinobacter segnicrescens* (Table 11) to give strain sKM.547. The fabZ gene and then the fabA gene of sZR.409 were replaced with the fabZ gene from *Marinobacter similis* (WP_041342533) and then the fabA gene from *Marinobacter similis* (Table 11) to give strain sAL.180.

Plasmid pKM.022 (Table 6), a pCL1920-derivative vector (SC101 replicon, spectinomycin resistance marker), comprised a thioesterase, fatA, from *Arabidopsis thaliana* and a β-ketoacyl-ACP synthase, fabB, such that they formed an operon controlled by the IPTG-inducible Ptrc promoter.

Plasmid pKM.022 was transformed into strains sKM.472, sKM.545, sKM.547 and sAL.180 resulting in strains sKM.478, sKM.557, sKM.559 and sAL.219, respectively (table 7). The four strains were subjected to small scale fermentation and product analysis as described in the methods (see above).

All four strains produced significant amounts of ω9-mUFA. As can be seen in table 10, the strain with fabA from *Marinobacter aquaeolei*, sKM.478, produced 1357 mg/L ω9-mUFA, the strain with fabA from *Marinobacter nanhaiticus*, sKM.557, produced 279 mg/L ω9-mUFA, the strain with fabA from *Marinobacter segnicrescens*, sKM.559, produced 1344 mg/L ω9-mUFA, and the strain with fabA from *Marinobacter similis*, sAL.219, produced 200 mg/L ω9-mUFA. The majority of ω9-mUFA in all three strains was ω9-(z7) hexadecenoic acid.

This example showed that *E. coli* strains with the native fabA gene replaced by heterologous fabA genes from the genus *Marinobacter*, e.g. *M. aquaeolei*, *M. nanhaiticus*, *M. segnicrescens* and *M. similis*, are viable and when a thioesterase is expressed produce significant amounts of non-native ω9-mUFA, e.g. ω9(z7)-hexadecenoic acid.

Table 11 shows fabA genes from various *Marinobacter* species.

TABLE 10

Production of ω9-mUFAs in recombinant *E. coli* strains with fabA from various Marinobacter strains.

| | fabA gene | fabZ gene | FFA (mg/L) | mUFA (mg/L) | ω9-mUFA (mg/L) | ω9-mUFA of mUFA (%) |
|---|---|---|---|---|---|---|
| sKM.478 | Maqu | Maqu | 2202 | 1449 | 1357 | 94 |
| sKM.557 | Mnan | Maqu | 1270 | 357 | 279 | 78 |
| sKM.559 | Mseg | Maqu | 2370 | 1428 | 1344 | 94 |
| sAL.219 | Msim | Msim | 316 | 217 | 200 | 90 |

TABLE 11

FabA-type dual 3-OH acyl-ACP dehydratase/ isomerases from *Marinobacter* ssp.

| Species | Accession Number | Sequence Identity to fabA_Maqu |
|---|---|---|
| *Marinobacter aquaeolei* VT8 (Maqu) | WP_011786589 | 100 |
| *Marinobacter similis* (Msim) | WP_041339271 | 88.2 |
| *M. segnicrescens* (Mseg) | WP_091850164 | 88.8 |
| *Marinobacter nanhaiticus* (Mnan) | WP_004580667 | 74.7 |
| *Marinobacter santoriniensis* | WP_008939378 | 85.2 |
| *Marinobacter lipolyticus* | WP_018404558 | 80.5 |
| *Marinobacter lipolyticus* | WP_012136761 | 87.6 |
| *Marinobacter algicola* | WP_036132164 | 81.7 |
| *Marinobacter excellens* | WP_044383626 | 95.3 |
| *Marinobacter daepoensis* | WP_029652437 | 95.3 |
| *Marinobacter* sp. ELB17 | WP_007349446 | 81.7 |
| *Marinobacter* sp. BSs20148 | WP_014872483 | 81.1 |

TABLE 11-continued

FabA-type dual 3-OH acyl-ACP dehydratase/ isomerases from *Marinobacter* ssp.

| Species | Accession Number | Sequence Identity to fabA_Maqu |
|---|---|---|
| *Marinobacter* sp. HL-58 | WP_027833128 | 84.7 |
| *Marinobacter* sp. AK21 | WP_036132164 | 92.9 |
| *Marinobacter* sp. MCTG268 | WP_036208832 | 80.5 |
| *Marinobacter* sp. ES-1 | WP_022989297 | 97.6 |
| *Marinobacter hydrocarbonoclasticus* | WP_072676371 | 95.0 |

Example 6

The following Example illustrates production of ω9-monounsaturated hydroxyl fatty acids in recombinant *E. coli*. The *E. coli* strains heterologously express FabA and FabZ from *Marinobacter aquaeolei* replacing native *E. coli* FabA and FabZ. The ω9-monounsaturated hydroxyl fatty acids produced are predominantly 16 carbon hydroxyl fatty acids.

As is shown below, a recombinant *E. coli* strain which has both its fabA and fabZ genes replaced by heterologous fabA and fabZ genes from *Marinobacter aquaeolei* that also expresses a heterologous thioesterase and a heterologous ω-hydroxylase produces monounsaturated hydroxyl fatty acids with the double bond almost exclusively in the non-native ω9 position and mainly 16 carbon atoms.

The base strain for this experiment was sRF.048 (see Example 4 and Table 7). sRF.048 heterologously FabA and FabZ from *Marinobacter aquaeolei*. Plasmid pKM.010 was transformed into sRF.048 resulting in strain sRF.068 (Table 7).

Plasmid pKM.10 (Table 6) comprises a pCL1920-derivative vector (SC101 replicon, spectinomycin resistance marker) with a FatA thioesterase from *Arabidopsis thaliana* (UniProtKB—Q42561 (FATA1_ARATH) and a *E. coli* β-ketoacyl-ACP synthase (FabB see e.g., Carlsberg Res. Commun. Vol. 53, p. 357-370, 1988) which together form an operon controlled by the IPTG-inducible Ptrc promoter. The plasmid pKM.10 further comprises a gene coding for a hybrid CYP153A-reductase hybrid fusion (cyp153A-RhF) enzyme (see International Patent Application Publication WO 2017/106205) controlled by an IPTG-inducible PT5 promoter.

Strain sRF.068 was subjected to small scale fermentation and product analysis as described above in Example 1.

Strain sRF.068 produced 300 mg/L fatty acids and 1935 mg/L ω-hydroxy fatty acids of which 1109 mg/L was 16-hydroxyhexadecenoic acid.

An authentic standard for ω9(z7)-16-hydroxyhexadecenoic acid was not available. Therefore, the structure and the double bond position of 16-hydroxy-ω9-hexadecenoic acid was determined by GC/MS of its dimethyl disulphide (DMDS) adduct after BSTFA/TMCS derivatization (FIG. 11).

Figure 11:
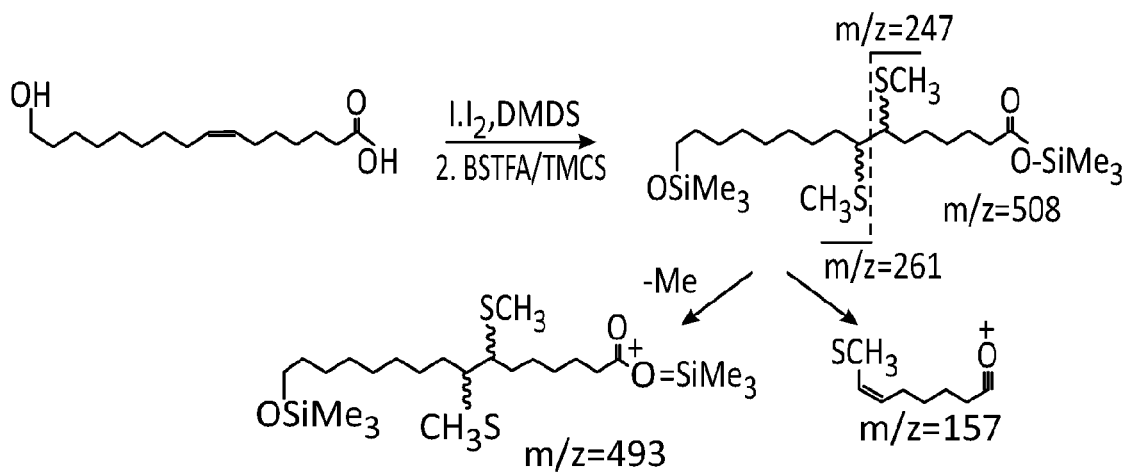
FIG. 11 Illustrates the mass spectrum and ion fragmentation pattern of the dimethyl disulphide (DMDS) adduct of ω9(z7)-16-hydroxy-hexadecenoic acid from an extract of *E. coli* sRF.068 after BSTFA/TMCS derivatization.
Figure 11:
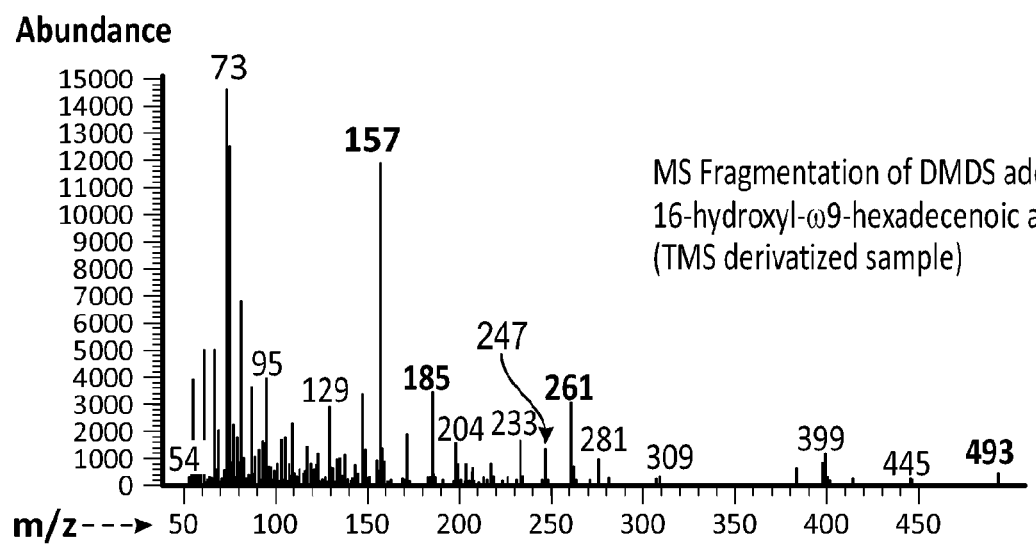

As can be seen from FIG. 11, the double bond of the 16-hydroxyhexadecenoic acid was in the ω9 position, i.e. the compound was identified as ω9-(z7)-16-hydroxyhexadecenoic. The DMDS adduct of (ω7-(z9)-16-hydroxyhexadecenoic was not detectable in this sample.

Thus, this example shows that *E. coli* strains with the native FabA and fabZ genes replaced by the fabA and fabZ genes from *M. aquaeolei* are viable and when a thioesterase and ω-hydroxylase are expressed the strain produces significant amounts of monounsaturated hydroxyl fatty acids with the double bond almost exclusively in the non-native ω9 position, e.g. ω9 (z7)-16-hydroxyhexadecenoic acid.

ω9 (z7)-16-hydroxyhexadecenoic acid can be chemically converted to (z7)-16 hexadecenolide (see e.g., International Patent Application Publication WO 2015/157719 A9) also known as ambrettolide, a musk fragrance that naturally occurs in seeds of the ambrette flower.

Example 7

The following Example illustrates production of 18 carbon ω9-monounsaturated hydroxyl fatty acids and 18 carbon ω9-monounsaturated diacids by recombinant *E. coli* strains that heterologously express FabA and FabZ from *Marinobacter aquaeolei* replacing native *E. coli* FabA and FabZ.

As is shown below, a recombinant *E. coli* strain that heterologously expresses FabA and FabZ from *Marinobacter aquaeolei* replacing native *E. coli* FabA and FabZ and which also expresses a heterologous thioesterase and a heterologous ω-hydroxylase, produces 18 carbon monounsaturated hydroxyl fatty acids with the double bond almost exclusively in the non-native ω9 position.

Furthermore, when the recombinant *E. coli* strain further expresses two heterologous dehydrogenases (a heterologous alcohol dehydrogenase and a heterologous aldehyde dehydrogenase) the recombinant *E. coli* strain produces 18 carbon monounsaturated diacids with the double bond almost exclusively in the non-native ω9 position.

The base strain for this experiment was sRF.048 (see Example 4 and Table 7). sRF.048 heterologously expresses FabA and FabZ from *Marinobacter aquaeolei*.

The Base Strain sRF.048 was Transformed with Plasmid pKM.104 to Provide Strain sKM.487 (Table 7).

Plasmid pKM.104 (Table 6) comprises a pCL1920-derivative vector (SC101 replicon, spectinomycin resistance marker) with a FatA thioesterase from *Arabidopsis thaliana* (UniProtKB—Q42561 (FATA1_ARATH) and a β-ketoacyl-ACP synthase, FabB, from *Marinobacter aquaeolei* (UniProtKB_U7P5T0) which together form an operon controlled by the IPTG-inducible Ptrc promoter. The plasmid pKM.104 further comprises a gene coding for a CYP153A-reductase hybrid fusion (cyp153A-RhF) enzyme (see, International Patent Application Publication WO 2017/106205; International Patent Application Publication WO 2014/201474) controlled by an IPTG-inducible PT5 promoter.

Thus, in addition to heterologously expressing FabA and FabZ from *Marinobacter aquaeolei*, strain sKM.487 also heterologously expresses a hybrid cyp153A-RhF fusion enzyme, a FatA from *Arabidopsis thaliana*, and a FabB from *Marinobacter aquaeolei*.

The Base Strain sRF.048 was Also ω-Transformed with Plasmid pKM.104 and Plasmid pKM. 057 to Provide Strain sKM. 484.

Plasmid pKM.057 (Table 6) comprises a pACYC-derivative vector (p15a replicon, kanamycin resistance marker) with a alcohol dehydrogenase from *Pseudomonas oleovorans* (UniProtKB—Q00593) and a aldehyde dehydrogenase from *Acinetobacter baylyi* (UniProtKB_Q6FAS2) which together form an operon controlled by the IPTG-inducible Ptrc promoter.

Thus, in addition to heterologously expressing FabA and FabZ from *Marinobacter aquaeolei*, strain sKM.484 also heterologously expresses a hybrid cyp153A-RhF fusion enzyme, a FatA from *Arabidopsis thaliana*, FabB, from *Marinobacter aquaeolei*, an alcohol dehydrogenase from *Pseudomonas oleovorans* and an aldehyde dehydrogenase from *Acinetobacter baylyi*.

Strain sKM.487 and sKM. 484 were Subjected to Small Scale Fermentation and Product Analysis as Described Above in Example 1.

Strain sKM.487 produced 620 mg/L fatty acids and 1420 mg/L ω-hydroxy fatty acids of which 390 mg/L was (z9) 18-hydroxyoctadecenoic acid.

Strain sKM.484 produced 390 mg/L fatty acids, 110 mg/L ω-hydroxy fatty acids and 1800 mg/L α/ω-diacids of which 390 mg/L was (z9)1,18-hydroxyoctadecenedioic acid.

Thus, this example shows that *E. coli* strains with the native FabA and fabZ genes replaced by the fabA and fabZ genes from *M. aquaeolei* are viable and when a thioesterase and ω-hydroxylase are expressed produce significant amounts of monounsaturated hydroxyl fatty acids with the double bond almost exclusively in the non-native ω9 position, e.g. ω9 (z9)-18-hydroxyoctadecenoic acid, or produce significant amounts of monounsaturated diacids with the double bond almost exclusively in the non-native ω9 position, e.g. ω9 (z9)-1,18-hydroxyoctadecenedioic acid.

(z9)-1,18-octadecenedioic acid can be chemically converted to (z9)-cycloheptadecen-1-one (see e.g., International Patent Application Publication WO 2015/157719 A9) also known as civettone, a musk fragrance that naturally occurs in civets.

Example 8

The following Example illustrates production of ω5-monounsaturated fatty acids by recombinant *E. coli* strains that heterologously express FabZ from *Zavarzinella formosa*.

This example describes recombinant *E. coli* strains heterologously expressing fabZ genes from *Zavarzinella formosa*. The cells further express a heterologous thioesterase and produce non-native ω5-monounsaturated fatty acids. In a preliminary, non-optimized test, the level of ω5-monounsaturated fatty acids could not be determined when FabZ gene from *Zavarzinella formosa* on a plasmid was introduced into *E. coli* without additional genetic modifications.

To achieve ω5-monounsaturated fatty acids productions, the genome of the recombinant *E. coli* strains can be engineered as follows: At least one of the fabZ genes from *Zavarzinella formosa* (accession numbers WP_020473045, WP_020473048, WP_020469995) (see Table 1) are cloned under the control of a constitutive promoter. However, in some embodiments, two of the fabZ genes from *Zavarzinella formosa* (accession numbers WP_020473045, WP_020473048, WP_020469995) (see Table 1) can be cloned under the control of a constitutive promoter. The cloned fabZ gene(s) can be integrated into the *E. coli* chromosome by techniques well known in the art (see e.g., Current Protocols in olecular Biology, supra). The *Zavarzinella formosa* fabZ genes may be integrated in place of the native *E. coli* fabA and/or fabZ genes. Alternatively, the *Zavarzinella formosa* fabZ genes may be integrated at neutral sites of the chromosome and the native *E. coli* fabA and/or fabZ genes may be attenuated or deleted. In addition, the *E. coli* trans-2-enoyl-ACP reductase gene, fabI, may be replaced with a trans-2-enoyl-ACP reductase gene from *Zavarzinella formosa*, e.g. accession number WP_020471657. In addition, other *E. coli* genes coding for enzymes or proteins involved in fatty acid biosynthesis, e.g. fabB, fabF, fabG or acp, may be replaced with the corresponding genes from *Zavarzinella formosa*.

Plasmid pLKW.072 (pCL-Ptrc-fatA3_Atal_fabB) or pXC.008 (pCL-Ptrc-A3DJY9_CLOTH) (see Table 6 and Example 4) can be transformed into the recombinant *E. coli* strains and the resulting strains produce non-native ω5-monounsaturated fatty acids when cultured as described in Example 1.

Example 9

The following Example illustrates production of ω5-monounsaturated fatty acids by recombinant *E. coli* strains expressing heterologous FabZ from *Mucilaginibacter paludis*. The cells further express a heterologous thioesterase and produce non-native ω5-monounsaturated fatty acids. In a preliminary, non-optimized test, the level of ω5-monounsaturated fatty acids could not be determined when FabZ gene from *Mucilaginibacter paludis* on a plasmid was introduced into *E. coli* without additional genetic modifications.

To achieve ω5-monounsaturated fatty acids productions, the genome of the recombinant *E. coli* strains can be engineered as follows: At least one or two of the fabZ genes from *Mucilaginibacter paludis* (accession numbers WP_040625927, WP_008512849, WP_008512862) (see Table 1) can be cloned under the control of a constitutive promoter and can be integrated into the *E. coli* chromosome. The *Mucilaginibacter paludis* fabZ genes may be integrated in place of the native *E. coli* fabA and/or fabZ genes. Alternatively, the *Mucilaginibacter paludis* fabZ genes may be integrated at neutral sites of the chromosome and the native *E. coli* fabA and/or fabZ genes may be attenuated or deleted. In addition, the *E. coli* trans-2-enoyl-ACP reductase gene, fabI, may be replaced with a trans-2-enoyl-ACP reductase gene from *Mucilaginibacter paludis*, e.g. accession number WP_008508657. In addition, other *E. coli* genes coding for enzymes or proteins involved in fatty acid biosynthesis, e.g. fabB, fabF, fabG or acp, may be replaced with the corresponding genes from *Mucilaginibacter paludis*.

Plasmid pLKW.072 (pCL-Ptrc-fatA3_Atal_fabB) or pXC.008 (pCL-Ptrc-A3DJY9_CLOTH) (see Table 6 and example 4) can be transformed into the recombinant *E. coli* strains and some of the resulting strains produce non-native ω5-monounsaturated fatty acids when cultured as described in Example 1.

Example 10

The following Example illustrates production of ω3-monounsaturated fatty acids by recombinant *E. coli* strains that heterologously express FabA-like domains from polyketide synthases. The cells further express a heterologous thioesterase and produce ω3-monounsaturated fatty acids. In a preliminary, non-optimized tests, the level of ω3-monounsaturated fatty acids could not be determined when plasmids encoding fabA-like domain were introduced into *E. coli* without additional genetic modifications.

To achieve ω3-monounsaturated fatty acids productions, the genome of the recombinant *E. coli* strains can be engineered as follows: At least one of the fabA-like domain genes or the fabA-like didomain genes from polyketide synthase genes orfC from *Thraustochytrium*, orf7 from *Shewanella* or pfaC from *Photobacterium* (see Table 2 for accession numbers and additional examples of such genes) may be cloned under the control of a constitutive promoter and may be integrated into the *E. coli* chromosome. The fabA-like genes or didomain genes may be integrated in place of the native *E. coli* fabA gene. Alternatively, the fabA-like genes or didomain genes may be integrated at neutral sites of the chromosome and the native *E. coli* fabA genes may be attenuated or deleted. In addition, the *E. coli* gene fabZ gene may be replaced with a heterologous fabZ gene, e.g. from an organism in table 3 or from a related polyketide biosynthesis cluster.

In addition, the *E. coli* trans-2-enoyl-ACP reductase gene, fabI, may be replaced with a trans-2-enoyl-ACP reductase domain gene from a related polyketide synthase gene cluster, e.g. orfB (accession AOG21005) or orfC (accession AOG21006) from *Thraustochytrium*, or PfaD from *Shewanella* (accession AAB81126). In addition, other *E. coli* genes coding for enzymes or proteins involved in fatty acid biosynthesis, e.g. fabB, fabF, fabG or acp, may be replaced with the corresponding domain genes from a related polyketide synthase gene cluster.

Plasmid pLKW.072 (pCL-Ptrc-fatA3_Atal_fabB) or pXC.008 (pCL-Ptrc-A3DJY9_CLOTH) (see Table 6 and example 4) can be transformed into the recombinant *E. coli* strains and some of the resulting strains produce non-native ω3-monounsaturated fatty acids when cultured as described in Example 1.

Example 11

The following Example illustrates production of ω9-monounsaturated fatty acids by recombinant *E. coli* strains that heterologously express FabA from the gamma-proteobacteria *Alcanivorax borkumensis*.

This example describes recombinant *E. coli* strains that heterologously express fabA genes from *Alcanivorax borkumensis*. The cells further express a heterologous thioesterase and produce non-native ω9-monounsaturated fatty acids.

The fabA gene from *Alcanivorax borkumensis* (WP_011588119) may be cloned into a pACYC-derivative vector (p15A replicon, kanamycin resistance marker) such that its expression is controlled by the IPTG-inducible Ptrc promoter.

The resulting fabA-containing plasmid may be cotransformed with a plasmid such as pKM.022 which comprises a thioesterase (see Table 6 and Example 4) into an *E. coli* base strain such as PAM155, sLKW.186, sZR.409 (see Table 7 and Examples 2 & 4) or a similar *E. coli* strain, and the resulting strains produce non-native ω9-monounsaturated fatty acids when cultured as described in Example 1.

As is apparent to one of skill in the art, various modifications and variations of the above aspects and embodiments can be made without departing from the spirit and scope of this disclosure. Such modifications and variations are thus within the scope of this disclosure.

We claim:

1. A viable recombinant bacterium comprising a heterologous dual 3-hydroxy-acyl-ACP dehydratase/isomerase, wherein:
   the viable recombinant bacterium produces a non-native monounsaturated fatty acid derivative when cultured;
   the non-native monounsaturated fatty acid derivative has a double bond in a position characteristic of the heterologous dual 3-hydroxy-acyl-ACP dehydratase/isomerase;
   the viable recombinant bacterium is a bacterium of taxonomic classification: Class gamma-proteobacteria;
   the heterologous dual 3-hydroxy-acyl-ACP dehydratase/isomerase is derived from a bacterium of taxonomic classification: Class gamma-proteobacteria;

the heterologous dual 3-hydroxy-acyl-ACP dehydratase/
isomerase is a Fab A homolog or a FabA-type dual
3-hydroxy-acyl-ACP dehydratase/isomerase; and the heterologous dual 3-hydroxy-acyl-ACP dehydratase/
isomerase replaces the native dual 3-hydroxy-acyl-
ACP dehydratase/isomerase.

2. The viable recombinant bacterium of claim 1, further comprising a heterologous thioesterase.

3. The viable recombinant bacterium of claim 1, wherein the non-native monounsaturated fatty acid derivative comprises at least 30% of total monounsaturated fatty acid derivatives.

4. The viable recombinant bacterium of claim 1, wherein the viable recombinant bacterium comprises non-native monounsaturated acyl-thioesters.

5. The viable recombinant bacterium of claim 1, wherein the viable recombinant bacterium further comprises a heterologous 3-hydroxyacyl-ACP dehydratase (FabZ).

6. The viable recombinant bacterium of claim 5, further comprising a heterologous β-ketoacyl-ACP synthase I (FabB).

7. The viable recombinant bacterium of claim 5, further comprising a heterologous trans-2-enoyl-ACP reductase.

8. The viable recombinant bacterium of claim 5, further comprising a heterologous thioesterase and a heterologous omega-hydroxylase.

9. The viable recombinant bacterium of claim 1, wherein:
the viable recombinant bacterium produces omega-hydroxy (ω-hydroxy) fatty acid derivatives when cultured; and the ω-hydroxy fatty acid derivatives comprise non-native monounsaturated ω-hydroxy fatty acid derivatives.

10. The viable recombinant bacterium of claim 9, further comprising an alcohol dehydrogenase, an alcohol oxidase, or an aldehyde dehydrogenase, wherein the viable recombinant bacterium produces non-native monounsaturated fatty diacids when cultured.

11. The viable recombinant bacterium of claim 1, wherein the viable recombinant bacterium is a viable recombinant *E. coli*.

12. The viable recombinant bacterium of claim 1, wherein the heterologous dual 3-hydroxy-acyl-ACP dehydratase/isomerase is homologous to the *FabA* protein of *E. coli*.

13. The viable recombinant bacterium of claim 12, wherein the heterologous dual 3-hydroxy-acyl-ACP dehydratase/isomerase that is homologous to the *FabA* protein of *E. coli* is a *FabA* protein from a *Marinobacter* species.

14. The viable recombinant bacterium of claim 13, wherein the non-native monounsaturated fatty acid derivative has the double bond in the omega-9 (ω-9) position.

15. The viable recombinant bacterium of claim 14, wherein the viable recombinant bacterium further comprises a heterologous 3-hydroxyacyl-ACP dehydratase (FabZ) from a *Marinobacter* species and a heterologous thioesterase, and wherein the non-native monounsaturated fatty acid derivative with the double bond in the ω-9 position comprises greater than 50% of the total monounsaturated fatty acid derivatives.

16. The viable recombinant bacterium of claim 1, wherein the non-native monounsaturated fatty acid derivative has the double bond in the omega-3 (ω-3) position, omega-4 (ω-4) position, omega-5 (ω-5) position, omega-6 (ω-6) position, omega-8 (ω-8) position, omega-9 (ω-9) position, omega-10 (ω-10) position, omega-11 (ω-11) position, or omega-12 (ω-12) position.

17. The viable recombinant bacterium of claim 5, further comprising:
a thioesterase, a carboxylic acid reductase, and an alcohol dehydrogenase; or
an acyl-ACP reductase and an alcohol dehydrogenase; or
an acyl-CoA synthetase, an acyl-CoA reductase, and an alcohol dehydrogenase;
wherein the viable recombinant bacterium produces a non-native monounsaturated fatty acid derivative that is a fatty alcohol when cultured.

18. The viable recombinant bacterium of claim 17, wherein the non-native monounsaturated fatty alcohol has a double bond in the omega-5 (ω-5) position.

19. A method for producing a non-native monounsaturated fatty acid derivative, the method comprising culturing the viable recombinant bacterium of claim 1, and optionally isolating the non-native monounsaturated fatty acid derivative.

20. The method of claim 19, wherein:
the viable recombinant bacterium further comprises a heterologous 3-hydroxyacyl-ACP dehydratase;
the non-native monounsaturated fatty acid derivative is a fatty acid, a fatty ester, a fatty alcohol acetate ester, a fatty alcohol, a fatty aldehyde, a fatty amine, an omega-hydroxy fatty acid, a bifunctional fatty acid derivative, a 3-hydroxy fatty acid derivative, a hydrocarbon, a ketone, a terminal olefin, or an internal olefin; and
the non-native monounsaturated fatty acid derivative has a double bond in the omega-3 (ω-3) position, omega-4 (ω-4) position, omega-5 (ω-5) position, omega-6 (ω-6) position, omega-8 (ω-8) position, omega-9 (ω-9) position, omega-10 (ω-10) position, omega-11 (ω-11) position, or omega-12 (ω-12) position.

* * * * *